US011245079B2

(12) United States Patent
Jatsch et al.

(10) Patent No.: US 11,245,079 B2
(45) Date of Patent: Feb. 8, 2022

(54) MATERIALS FOR ORGANIC ELECTROLUMINESCENT DEVICES

(71) Applicant: Merck Patent GmbH, Darmstadt (DE)

(72) Inventors: Anja Jatsch, Frankfurt am Main (DE); Tobias Grossmann, Darmstadt (DE); Amir Hossain Parham, Frankfurt am Main (DE); Thomas Eberle, Landau (DE); Christof Pflumm, Darmstadt (DE); Jonas Kroeber, Frankfurt am Main (DE); Philipp Stoessel, Frankfurt am Main (DE); Elvira Montenegro, Weinheim (DE); Rouven Linge, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 192 days.

(21) Appl. No.: 16/390,675

(22) Filed: Apr. 22, 2019

(65) Prior Publication Data

US 2019/0280217 A1   Sep. 12, 2019

Related U.S. Application Data

(62) Division of application No. 15/120,336, filed as application No. PCT/EP2015/000146 on Jan. 27, 2015, now abandoned.

(30) Foreign Application Priority Data

Feb. 21, 2014  (EP) .................................... 14000624

(51) Int. Cl.
| | | |
|---|---|---|
| *H01L 51/00* | (2006.01) | |
| *C09K 11/06* | (2006.01) | |
| *C07D 405/04* | (2006.01) | |
| *C07D 417/10* | (2006.01) | |
| *C07D 209/96* | (2006.01) | |
| *C07D 401/04* | (2006.01) | |
| *C07D 405/10* | (2006.01) | |
| *C07D 409/04* | (2006.01) | |
| *C07D 413/04* | (2006.01) | |
| *C07D 413/10* | (2006.01) | |
| *C07D 487/10* | (2006.01) | |
| *C07D 491/20* | (2006.01) | |
| *C07D 491/22* | (2006.01) | |
| *C09B 11/00* | (2006.01) | |
| *C09B 21/00* | (2006.01) | |
| *C09B 57/00* | (2006.01) | |
| *H05B 33/20* | (2006.01) | |
| *C07D 209/94* | (2006.01) | |
| *C07D 491/107* | (2006.01) | |
| *H01L 51/50* | (2006.01) | |

(52) U.S. Cl.
CPC ........ *H01L 51/0072* (2013.01); *C07D 209/94* (2013.01); *C07D 209/96* (2013.01); *C07D 401/04* (2013.01); *C07D 405/04* (2013.01); *C07D 405/10* (2013.01); *C07D 409/04* (2013.01); *C07D 413/04* (2013.01); *C07D 413/10* (2013.01); *C07D 417/10* (2013.01); *C07D 487/10* (2013.01); *C07D 491/107* (2013.01); *C07D 491/20* (2013.01); *C07D 491/22* (2013.01); *C09B 11/00* (2013.01); *C09B 21/00* (2013.01); *C09B 57/00* (2013.01); *C09B 57/008* (2013.01); *C09K 11/06* (2013.01); *H01L 51/0052* (2013.01); *H01L 51/0059* (2013.01); *H01L 51/0061* (2013.01); *H01L 51/0071* (2013.01); *H01L 51/0073* (2013.01); *H01L 51/0074* (2013.01); *H05B 33/20* (2013.01); *C09K 2211/185* (2013.01); *H01L 51/5016* (2013.01); *Y02E 10/549* (2013.01)

(58) Field of Classification Search
CPC .. C07D 209/96; C07D 487/10; C07D 491/20; C09K 11/06; H01L 51/0071; H01L 51/0072

See application file for complete search history.

(56) References Cited

U.S. PATENT DOCUMENTS

| | | | |
|---|---|---|---|
| 9,040,172 B2 | 5/2015 | Parham et al. | |
| 9,199,972 B2 | 12/2015 | Parham et al. | |
| 9,324,954 B2 | 4/2016 | Parham et al. | |
| 2013/0256645 A1 | 10/2013 | Min et al. | |
| 2014/0225040 A1 | 8/2014 | Parham et al. | |
| 2014/0225046 A1 | 8/2014 | Jatsch et al. | |
| 2014/0275530 A1 | 9/2014 | Jatsch et al. | |

FOREIGN PATENT DOCUMENTS

| | | |
|---|---|---|
| DE | 102009031021 A1 | 1/2011 |
| DE | 102009053645 A1 | 5/2011 |
| KR | 20110002156 A | 1/2011 |
| KR | 20120081539 A * | 7/2012 |
| TW | 201348236 A | 12/2013 |
| WO | WO-2012069121 A1 | 5/2012 |
| WO | WO-2012074210 A2 | 6/2012 |
| WO | WO-2013017189 A1 | 2/2013 |

(Continued)

OTHER PUBLICATIONS

International Search Report for PCT/EP2015/000146 dated Apr. 2, 2015.

*Primary Examiner* — Jennifer A Boyd
*Assistant Examiner* — Sean M DeGuire

(57) ABSTRACT

The invention relates to compounds which are suitable for use in electronic devices, and electronic devices, in particular organic electroluminescent devices, containing said compounds.

18 Claims, No Drawings

(56) References Cited

FOREIGN PATENT DOCUMENTS

| WO | WO-2013041176 A1 | 3/2013 |
| WO | WO-2013056776 A1 | 4/2013 |
| WO | WO-2013109045 A1 | 7/2013 |
| WO | WO-2013151297 A1 | 10/2013 |
| WO | WO-2014010910 A1 | 1/2014 |
| WO | WO-2014129869 A1 | 8/2014 |

* cited by examiner

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2015/000146, filed Jan. 27, 2015, which claims benefit of European Application No. 14000624.8, filed Feb. 21, 2014, both of which are incorporated herein by reference in their entirety.

The present invention relates to materials for use in electronic devices, especially in organic electroluminescent devices, and to electronic devices, especially organic electroluminescent devices, comprising these materials.

In organic electroluminescent devices (OLEDs), emitting materials used are frequently organometallic complexes which exhibit phosphorescence rather than fluorescence, since this enables a significantly higher energy and power efficiency than is possible with fluorescent emitters. The properties of phosphorescent OLEDs are not just determined by the triplet emitters used. Also of particular significance here are especially the other materials used, such as matrix materials, hole blocker materials, electron transport materials, hole transport materials and electron or exciton blocker materials. Improvements to these materials can thus also lead to distinct improvements in the OLED properties. In general terms, however, there is still a need for improvement in OLEDs, especially also in OLEDs which exhibit triplet emission (phosphorescence), for example with regard to efficiency, operating voltage and lifetime.

According to the prior art, indenocarbazole derivatives, for example according to WO 2010/136109, WO 2011/000455 or KR 20120081539, or fluorene or spirobifluorene derivatives, for example according to WO 2012/074210, are among the matrix materials used for phosphorescent emitters in organic electroluminescent devices. Further improvements are desirable here, especially in relation to the efficiency, lifetime and thermal stability of the materials.

It is an object of the present invention to provide compounds suitable for use in an OLED, especially as matrix material for phosphorescent emitters, but also as hole transport and/or electron blocker material or, if appropriate, as hole blocker and/or electron transport material. It is a further object of the present invention to provide further organic semiconductors for organic electroluminescent devices, in order thus to enable the person skilled in the art to have a greater possible choice of materials for the production of OLEDs.

It has been found that, surprisingly, particular compounds described below achieve this object and are of good suitability for use in OLEDs and lead to improvements in the organic electroluminescent device. These improvements relate particularly to the lifetime and/or the operating voltage. The present invention therefore provides these compounds and electronic devices, especially organic electroluminescent devices, comprising such compounds.

The present invention provides a compound of formula (1), formula (2) or formula (3)

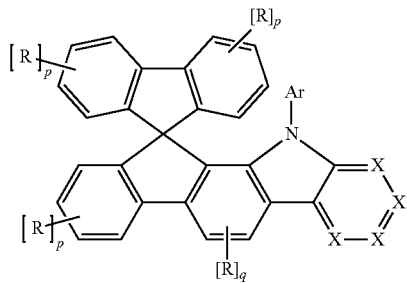

Formula (1)

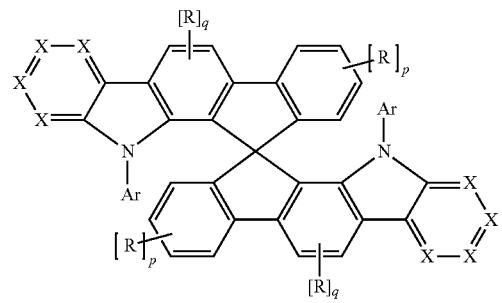

Formula (2)

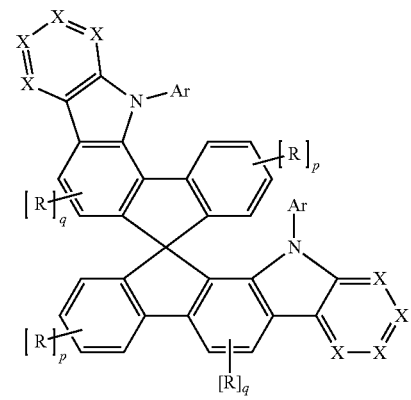

Formula (3)

where the symbols and indices used are as follows:

X is the same or different at each instance and is $CR^1$ or N; or two adjacent Xs are a group of the following formula (4), (5) or (6):

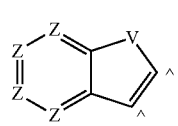

Formula (4)

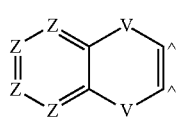

Formula (5)

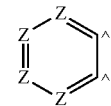

Formula (6)

27 where ˆ indicates the corresponding adjacent X groups in the formula (1) or (2) or (3), i.e. the group of the formula (4), (5) or (6) is fused to the compound of the formula (1), (2) or (3) at these positions;

V is the same or different at each instance and is $C(R^1)_2$, $NR^1$, O, S, $BR^1$, $Si(R^1)_2$ or C=O;

Z is the same or different at each instance and is $CR^1$ or N;

Ar is the same or different at each instance and is an aromatic ring system which has 6 to 40 aromatic ring atoms and may be substituted by one or more $R^2$ radicals, or a heteroaromatic ring system which has 5 to 40 aromatic ring atoms, does not contain any electron-deficient heteroaryl groups and may be substituted by one or more $R^2$ radicals;

R, $R^1$ is the same or different at each instance and is selected from the group consisting of H, D, F, Cl, Br, I, CN, $NO_2$, $N(Ar^1)_2$, $N(R^3)_2$, C(=O)$Ar^1$, C(=O)$R^3$, P(=O)$(Ar^1)_2$, $P(Ar^1)_2$, $B(Ar^1)_2$, $Si(Ar^1)_3$, $Si(R^3)_3$, a straight-chain alkyl, alkoxy or thioalkyl group having 1 to 20 carbon atoms or a branched or cyclic alkyl, alkoxy or thioalkyl group having 3 to 20 carbon atoms or an alkenyl group having 2 to 20 carbon atoms, each of which may be substituted by one or more $R^3$ radicals, where one or more nonadjacent $CH_2$ groups may be replaced by $R^3C$=$CR^3$, $Si(R^3)_2$, C=O, C=S, C=$NR^3$, P(=O)$(R^3)$, SO, $SO_2$, $NR^3$, O, S or $CONR^3$ and where one or more hydrogen atoms may be replaced by D, F, Cl, Br, I, CN or $NO_2$, an aromatic or heteroaromatic ring system which has 5 to 40 aromatic ring atoms and may be substituted in each case by one or more $R^3$ radicals, an aryloxy or heteroaryloxy group which has 5 to 40 aromatic ring atoms and may be substituted by one or more $R^3$ radicals, or an aralkyl or heteroaralkyl group which has 5 to 40 aromatic ring atoms and may be substituted by one or more $R^3$ radicals; at the same time, it is optionally possible for two $R^1$ substituents bonded to the same carbon atom to form a monocyclic or polycyclic, aliphatic, aromatic or heteroaromatic ring system which may be substituted by one or more $R^3$ radicals;

$R^2$ is the same or different at each instance and is selected from the group consisting of H, D, F, Cl, Br, I, CN, $NO_2$, $N(Ar^1)_2$, $N(R^3)_2$, C(=O)$Ar^1$, C(=O)$R^3$, P(=O)$(Ar^1)_2$, $P(Ar^1)_2$, $B(Ar^1)_2$, $Si(Ar^1)_3$, $Si(R^3)_3$, a straight-chain alkyl, alkoxy or thioalkyl group having 1 to 20 carbon atoms or a branched or cyclic alkyl, alkoxy or thioalkyl group having 3 to 20 carbon atoms or an alkenyl group having 2 to 20 carbon atoms, each of which may be substituted by one or more $R^3$ radicals, where one or more nonadjacent $CH_2$ groups may be replaced by $R^3C$=$CR^3$, $Si(R^3)_2$, C=O, C=S, C=$NR^3$, P(=O)$(R^3)$, SO, $SO_2$, $NR^3$, O, S or $CONR^3$ and where one or more hydrogen atoms may be replaced by D, F, Cl, Br, I, CN or $NO_2$, an aromatic or heteroaromatic ring system which has 5 to 40 aromatic ring atoms, does not contain any electron-deficient heteroaryl groups and may be substituted in each case by one or more $R^3$ radicals, an aryloxy or heteroaryloxy group which has 5 to 40 aromatic ring atoms, does not contain any electron-deficient heteroaryl groups and may be substituted by one or more $R^3$ radicals, or an aralkyl or heteroaralkyl group which has 5 to 40 aromatic ring atoms, does not contain any electron-deficient heteroaryl groups and may be substituted by one or more $R^3$ radicals; at the same time, it is possible for two or more adjacent $R^3$ substituents together to form a mono- or polycyclic aliphatic ring system;

$Ar^1$ is the same or different at each instance and is an aromatic or heteroaromatic ring system which has 5-30 aromatic ring atoms and may be substituted by one or more nonaromatic $R^3$ radicals; at the same time, two $Ar^1$ radicals bonded to the same nitrogen atom, phosphorus atom or boron atom may also be bridged to one another by a single bond or a bridge selected from $N(R^3)$, $C(R^3)_2$, O and S;

$R^3$ is the same or different at each instance and is selected from the group consisting of H, D, F, CN, an aliphatic hydrocarbyl radical having 1 to 20 carbon atoms and an aromatic or heteroaromatic ring system having 5 to 30 aromatic ring atoms in which one or more hydrogen atoms may be replaced by D, F, Cl, Br, I or CN, where two or more adjacent $R^3$ substituents together may form a mono- or polycyclic, aliphatic ring system;

p is the same or different at each instance and is 0, 1, 2, 3 or 4;

q is 0, 1 or 2;

where the two following compounds are excluded from the invention:

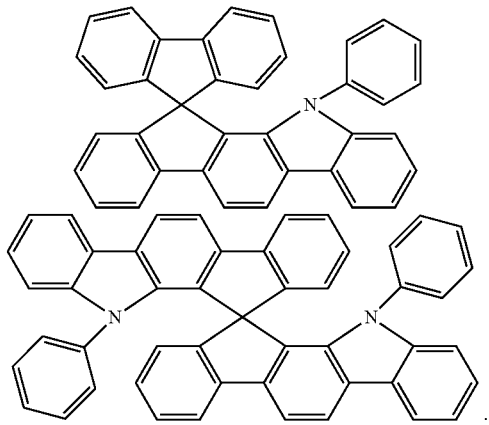

An aryl group in the context of this invention contains 6 to 60 carbon atoms; a heteroaryl group in the context of this invention contains 2 to 60 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused (annelated) aryl or heteroaryl group, for example naphthalene, anthracene, phenanthrene, quinoline, isoquinoline, etc. Aromatic systems joined to one another by a single bond, for example biphenyl, by contrast, are not referred to as an aryl or heteroaryl group but as an aromatic ring system.

An electron-deficient heteroaryl group in the context of the present invention is a heteroaryl group which has 5 aromatic ring atoms and at least two heteroatoms, or a heteroaryl group which has 6 aromatic ring atoms and at least one heteroatom, and also fused heteroaryl groups containing a five-membered ring having at least two heteroatoms and/or a six-membered ring having at least one heteroatom. A fused heteroaryl group is a heteroaryl group in which at least one heteroaryl group and at least one further aryl or heteroaryl group are fused directly to one another via a common edge. For example, imidazole, oxazole, benzimidazole, pyridine, pyrimidine, triazine, quinoline, quinoxaline, phenanthroline, etc. are to be regarded as electron-deficient heteroaryl groups, whereas, for example, pyrrole, furan, thiophene, indole, benzofuran, benzothiophene, carbazole, dibenzofuran and dibenzothiophene are not be regarded as electron-deficient heteroaryl groups in the context of the present invention, since these contain neither heteroaromatic five-membered rings having two or more heteroatoms nor heteroaromatic six-membered rings having at least one heteroatom.

An aromatic ring system in the context of this invention contains 6 to 60 carbon atoms in the ring system. A heteroaromatic ring system in the context of this invention contains 2 to 60 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be joined by a nonaromatic unit, for example a carbon, nitrogen or oxygen atom. For example, systems such as fluorene, 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are joined, for example, by a short alkyl group.

In the context of the present invention, an aliphatic hydrocarbyl radical or an alkyl group or an alkenyl or alkynyl group which may contain 1 to 40 carbon atoms and in which individual hydrogen atoms or $CH_2$ groups may also be replaced by the abovementioned groups are preferably understood to mean the methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups according to the present invention may be straight-chain, branched or cyclic, where one or more nonadjacent $CH_2$ groups may be replaced by the abovementioned groups; in addition, it is also possible for one or more hydrogen atoms to be replaced by D, F, Cl, Br, I, CN or $NO_2$, preferably F, Cl or CN, further preferably F or CN, especially preferably CN.

An aromatic or heteroaromatic ring system which has 5-60 aromatic ring atoms and may also be substituted in each case by the abovementioned $R^2$ radicals or a hydrocarbyl radical and which may be joined to the aromatic or heteroaromatic system via any desired positions is especially understood to mean groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from a combination of these systems.

Adjacent radicals or adjacent substituents in the context of the present application are understood to mean substituents which are bonded to carbon atoms that are in turn bonded directly to one another.

In a preferred embodiment of the invention, X is the same or different at each instance and is $CR^1$ or N, where not more than one X group per cycle is N; or two adjacent X groups are a group of the formula (4), where Z is the same or different at each instance and is $CR^1$ and V is the same or different at each instance and is $NR^1$, $C(R^1)_2$, O or S. More preferably, X is the same or different at each instance and is $CR^1$. When adjacent X groups are a group of the formula (4), it is preferable that the rest of the X groups in this cycle are $CR^1$.

Preferred embodiments of the compounds of formula (1) are the compounds of the following formulae (7) to (13), preferred embodiments of the compounds of formula (2) are the compounds of the following formula (14), and preferred embodiments of the compounds of formula (3) are the compounds of the following formula (15):

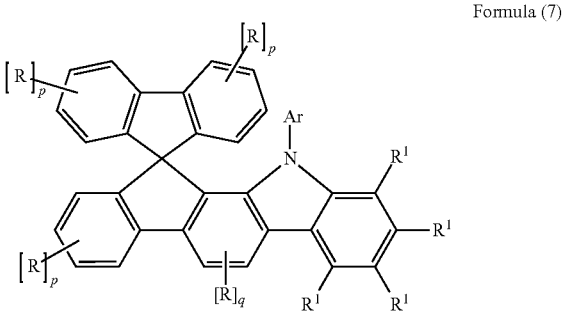

Formula (7)

Formula (8)
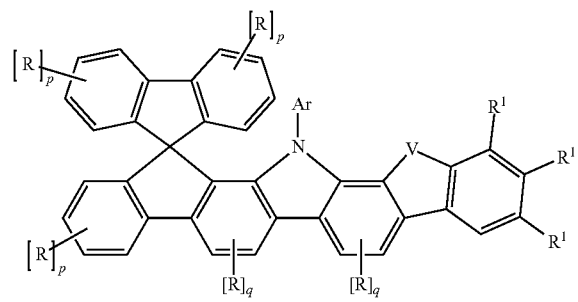
Formula (9)
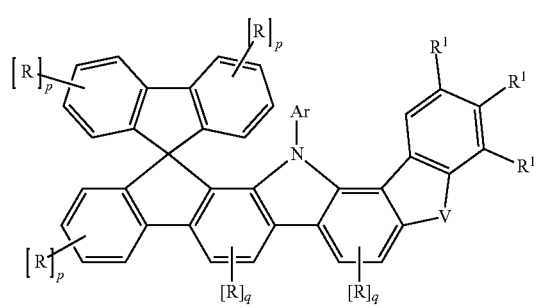
Formula (10)
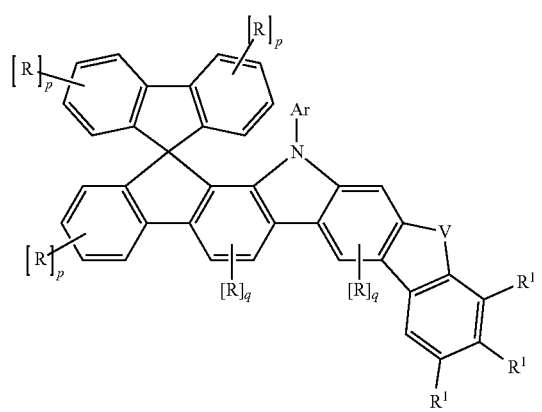
Formel (11)
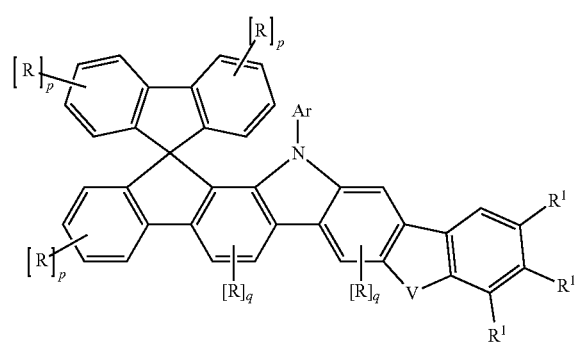
Formel (12)
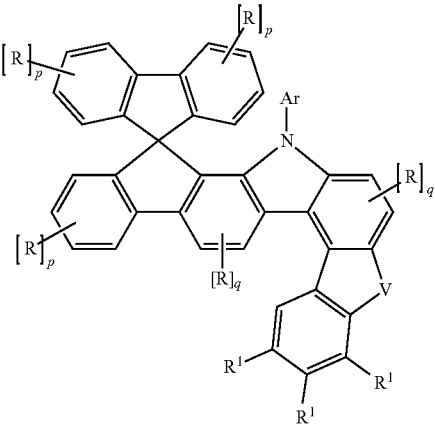
Formula (13)
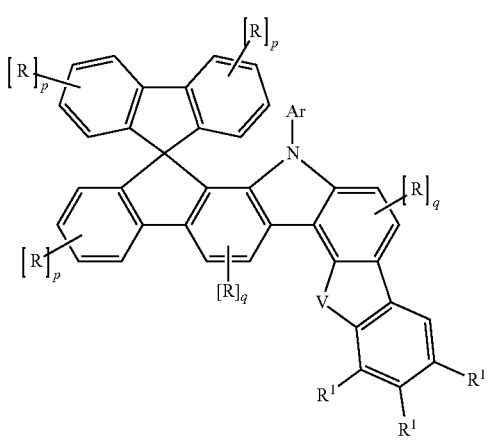
Formula (14)
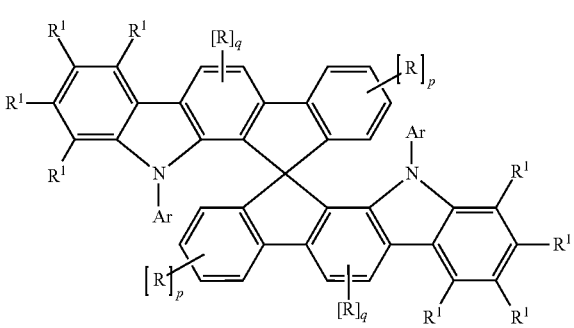

Formula (15)

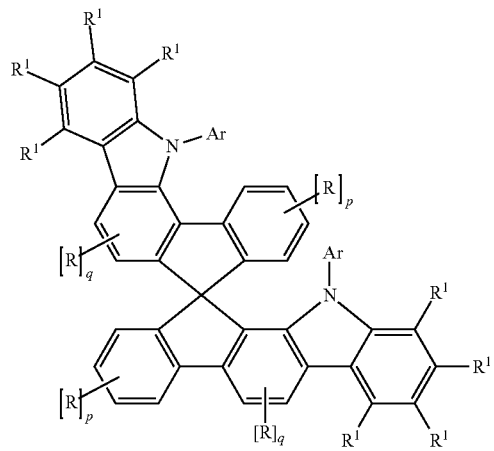

where the symbols and indices used have the definitions given above. In these formulae, V is preferably $NR^1$, $C(R')_2$, O or S. It may be preferable, when $V=C(R')_2$, for the two $R^1$ radicals together to form a ring and hence form a spiro system.

In a preferred embodiment of the invention, p is the same or different at each instance and is 0, 1 or 2, more preferably 0 or 1, and most preferably 0.

In addition, q is the same or different at each instance and is 0 or 1, more preferably 0.

Particularly preferred embodiments of the structures of formula (7) to (15) are the structures of the formula (7a) to (15a)

Formula (7a)

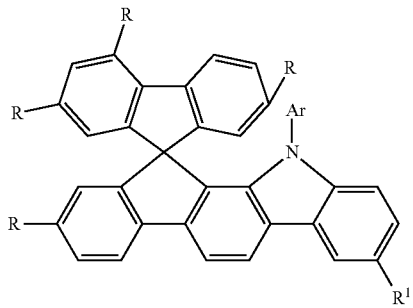

Formula (8a)

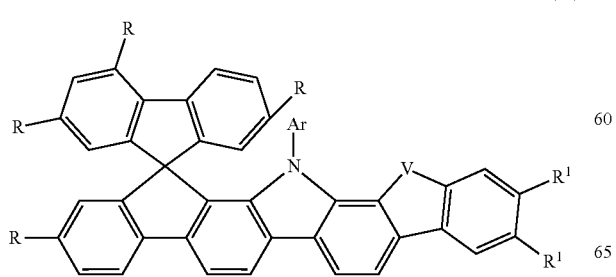

Formula (9a)

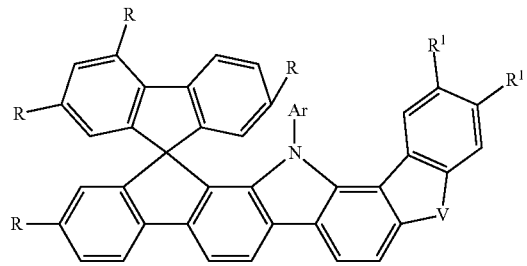

Formula (10a)

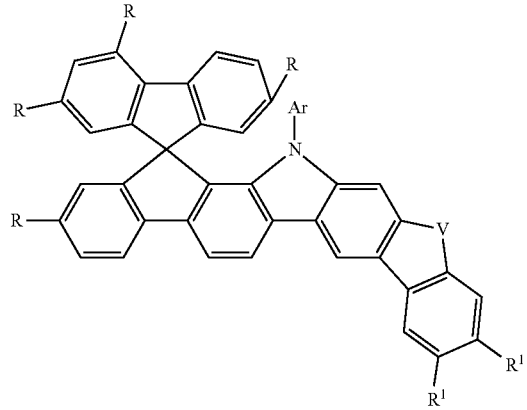

Formula (11a)

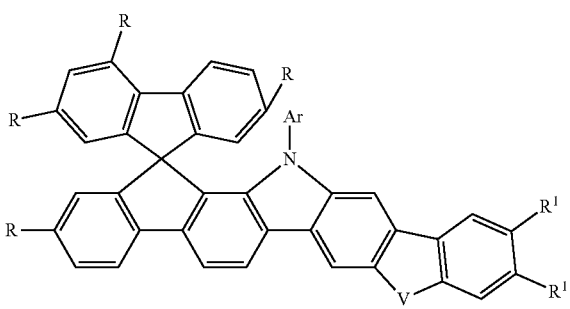

Formula (12a)

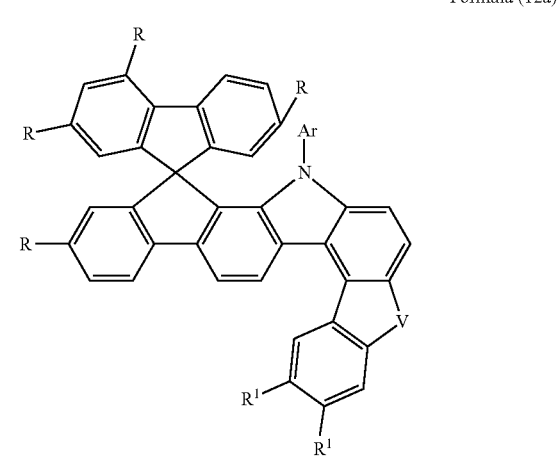

-continued

Formula (13a)

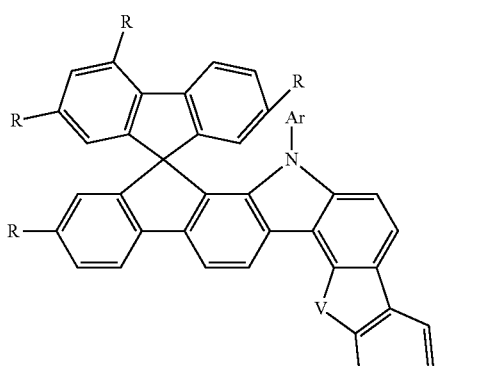

Formula (14a)

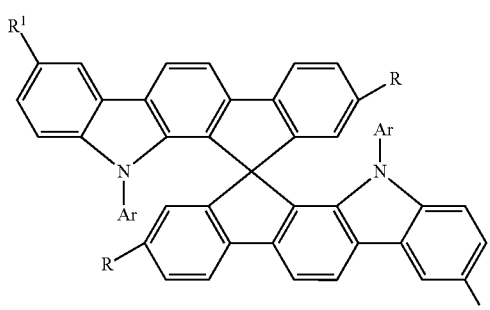

Formula (15a)

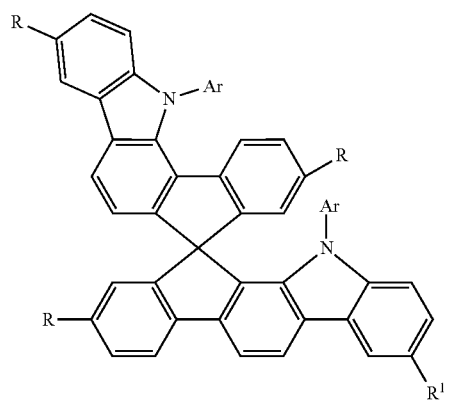

where the symbols and indices used have the definitions given above.

In a preferred embodiment of the invention, R is the same or different at each instance and is selected from the group consisting of H, F, CN, $N(Ar^1)_2$, a straight-chain alkyl group having 1 to 10 carbon atoms and a branched or cyclic alkyl group having 3 to 10 carbon atoms and an aromatic ring system which has 6 to 30 aromatic ring atoms and may be substituted by one or more nonaromatic $R^3$ radicals. In a particularly preferred embodiment of the invention, R is the same or different at each instance and is selected from the group consisting of H, a straight-chain alkyl group having 1 to 4 carbon atoms or a branched or cyclic alkyl group having 3 to 8 carbon atoms, most preferably H.

Very particular preference is thus given to the compounds of the following formulae (7b) to (15b):

Formula (7b)

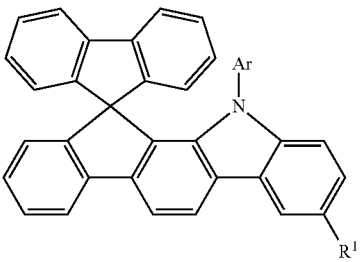

Formula (8b)

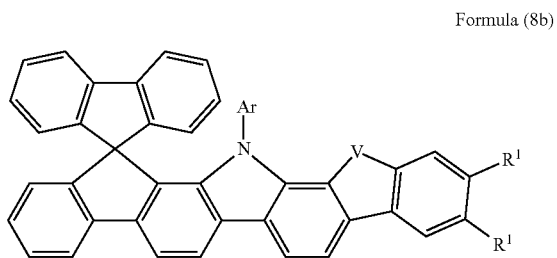

Formula 9b)

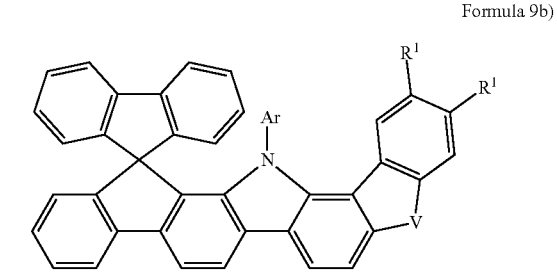

Formula (10b)

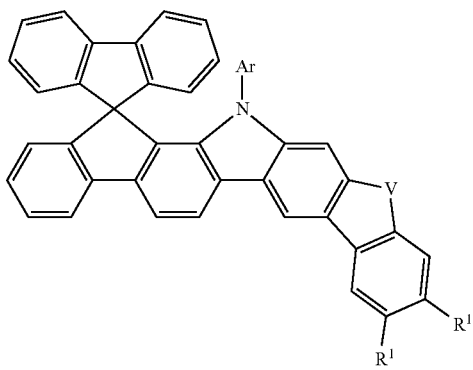

Formula (11b)

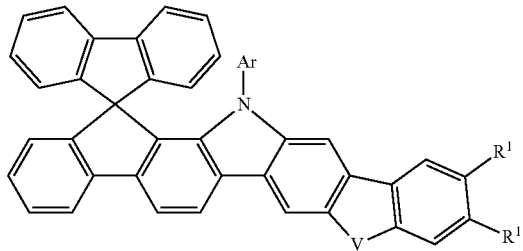

Formula (12b)

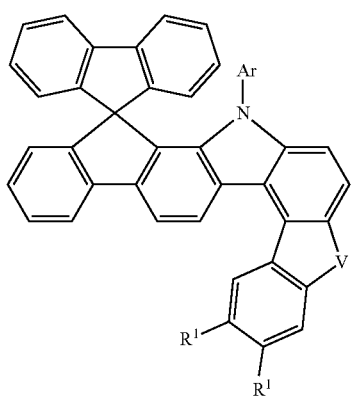

Formula (13b)

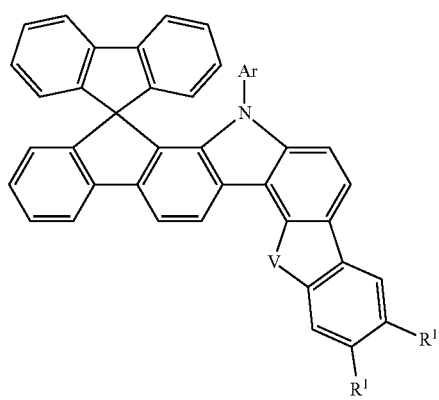

Formula (14b)

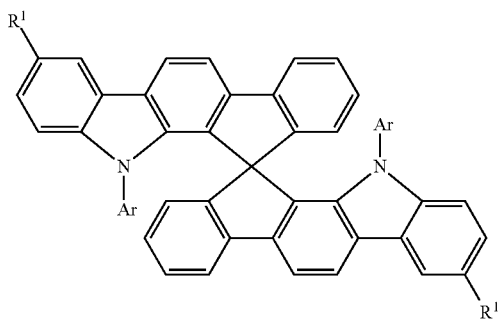

Formula (15b)

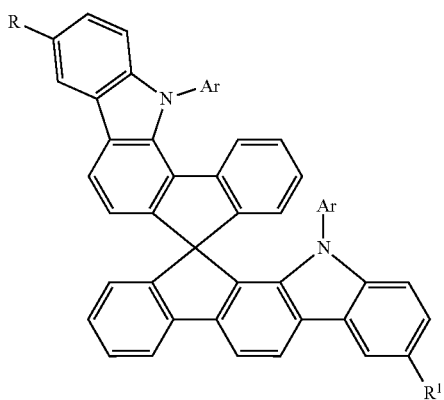

where the symbols used have the definitions given above.

There follows a description of the preferred substituents Ar and $R^1$ in the compounds of the formula (1), (2) and (3) and the preferred embodiments detailed above.

It is preferable when the compounds of the formula (1) and (3) or the preferred embodiments contain a total of at least 12 aromatic ring atoms in the Ar, $R^1$ and $R^2$ substituents, and the compounds of the formula (2) or the preferred embodiments contain a total of at least 24 aromatic ring atoms in the Ar, $R^1$ and $R^2$ substituents. This can be accomplished in different ways. Firstly, it is possible that Ar, or Ar together with the $R^2$ substituent bonded to Ar, is an aromatic or heteroaromatic ring system having at least 12 aromatic ring atoms. In this case, it is also possible for all $R^1$ groups to be H, or not to be an aromatic or heteroaromatic ring system. It is additionally possible that at least one $R^1$ radical is an aromatic or heteroaromatic ring system having at least 6 aromatic ring atoms or an $N(Ar^1)_2$ group. In this case, the Ar group may, for example, also preferably be a phenyl group, since the Ar, $R^1$ and $R^2$ substituents in the compound of the invention then nevertheless contain a total of 12 or more aromatic ring atoms.

In a preferred embodiment of the invention, Ar is the same or different at each instance and is an aromatic or heteroaromatic ring system which has 12 to 30 aromatic ring atoms, each of which may be substituted by one or more $R^2$ radicals. In this case, as defined above, the heteroaromatic ring system does not contain any electron-deficient heteroaryl groups.

Particularly preferred aromatic or heteroaromatic ring systems contain 12 to 24 aromatic ring atoms and may be substituted by one or more $R^2$ radicals. At the same time, the aromatic or heteroaromatic ring systems preferably do not contain any fused aryl or heteroaryl groups in which more than two aromatic six-membered rings are fused directly to one another, apart from any triphenylene groups. More preferably, they do not contain any aryl or heteroaryl groups in which aromatic six-membered rings are fused directly to one another at all. This preference applies particularly when the compound of the invention is being used as matrix material for a phosphorescent emitter or in a layer directly adjoining a phosphorescent emitting layer, and can be explained by the higher triplet energy of nonfused substituents. Thus, it is particularly preferable when Ar does not, for example, have any naphthyl groups or higher fused aryl groups and likewise does not have any quinoline groups, acridine groups, etc. In contrast, it is possible that Ar includes, for example, carbazole groups, dibenzofuran groups, fluorene groups, etc., since there are no 6-membered aromatic or heteroaromatic rings fused directly to one another, i.e. having a common edge, in these structures.

Preferred Ar groups are the same or different at each instance and are selected from the group consisting of phenyl, ortho-, meta- or para-biphenyl, ortho-terphenyl, meta-terphenyl, para-terphenyl or branched terphenyl, ortho-quaterphenyl, meta-quaterphenyl, para-quaterphenyl or branched quaterphenyl, 1-, 2-, 3- or 4-fluorenyl, 1-, 2-, 3- or 4-spirobifluorenyl, 1- or 2-naphthyl, pyrrole, furan, thiophene, indole, benzofuran, benzothiophene, 1-, 2- or 3-carbazole, 1-, 2- or 3-dibenzofuran, 1-, 2- or 3-dibenzothiophene, indenocarbazole, indolocarbazole or combinations of two or three of these groups, each of which may be substituted by one or more $R^2$ radicals. Further suitable Ar groups are anthracene, phenanthrene, triphenylene, pyrene or benzanthracene, each of which may be substituted by one or more $R^2$ radicals, or combinations of two or three of these groups with one another and/or with the abovementioned groups. These groups are suitable especially when the triplet energy of the compound of the invention is unimportant.
Preferred aromatic and heteroaromatic ring systems Ar are the groups of the following formulae Ar-1 to Ar-57:
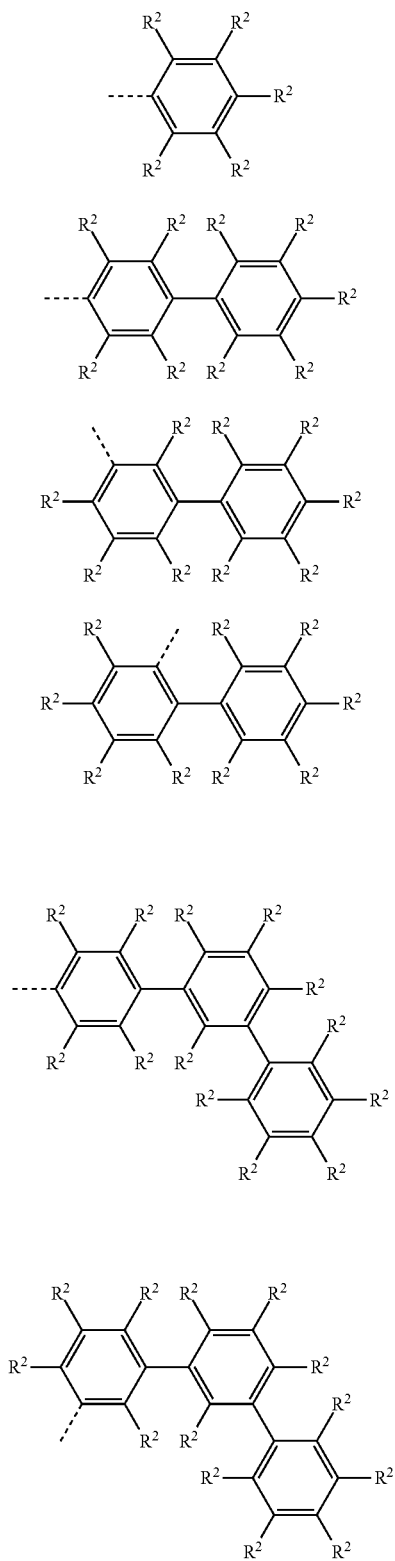
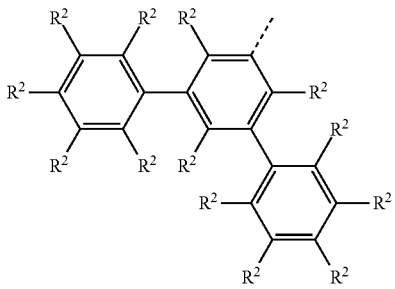
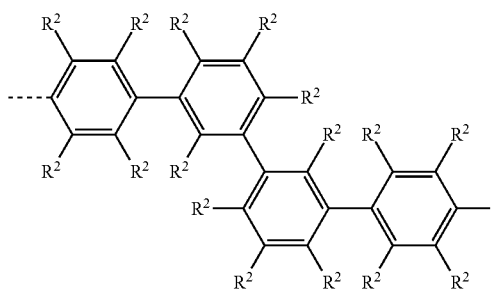
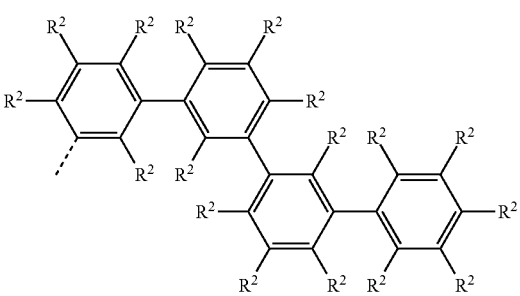
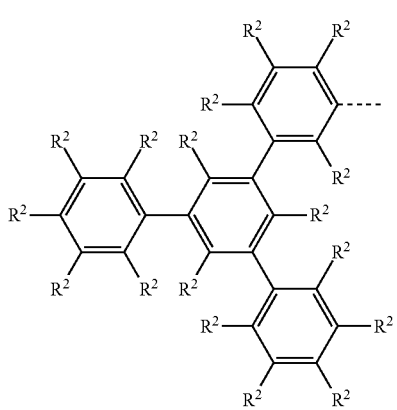

-continued
Ar-11
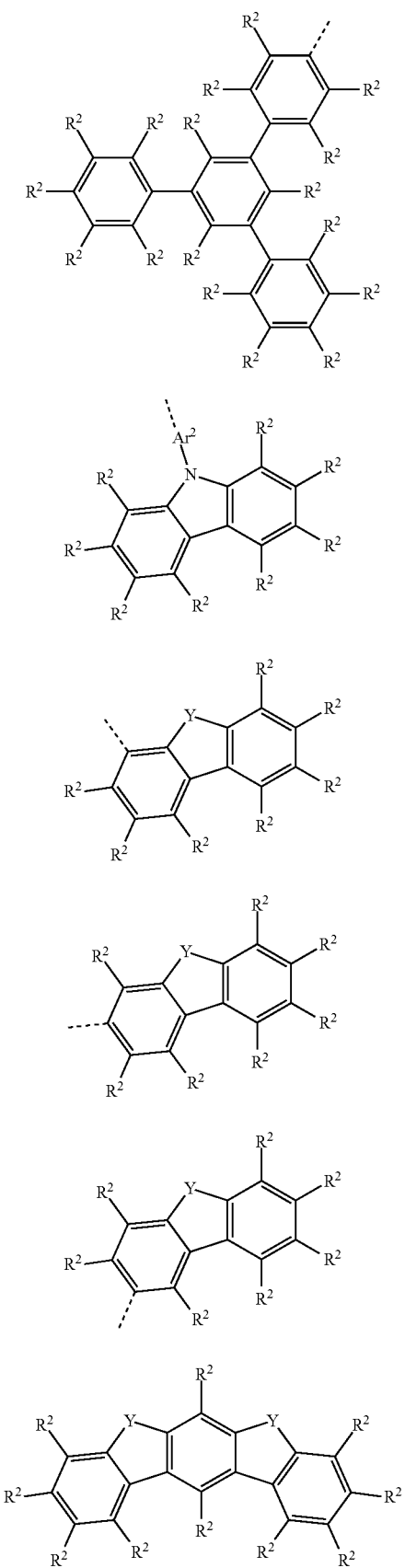
Ar-12
Ar-13
Ar-14
Ar-15
Ar-16
-continued
Ar-17
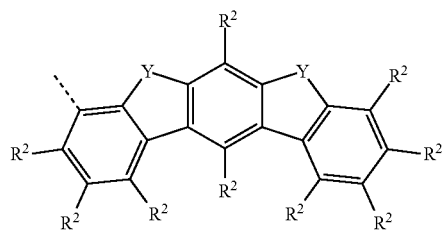
Ar-18
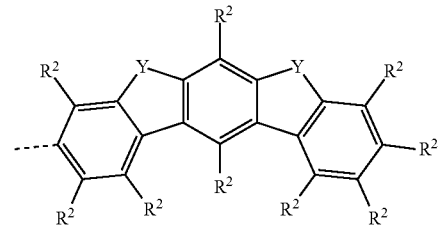
Ar-19
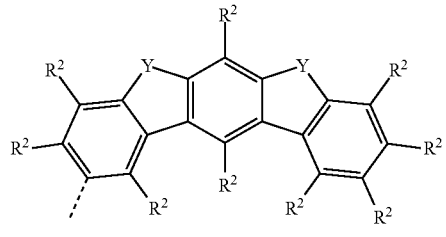
Ar-20
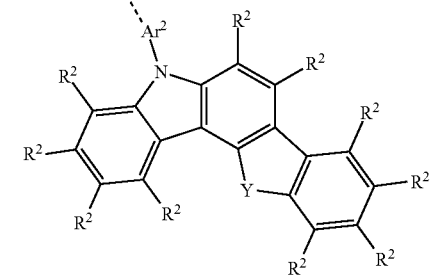
Ar-21
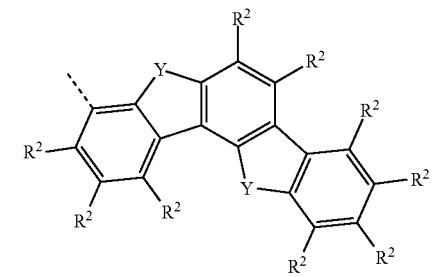
Ar-22
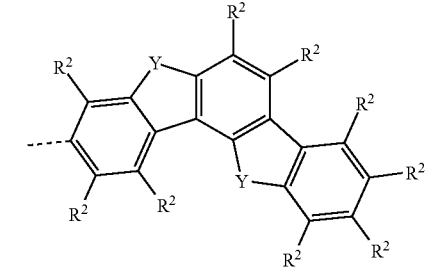

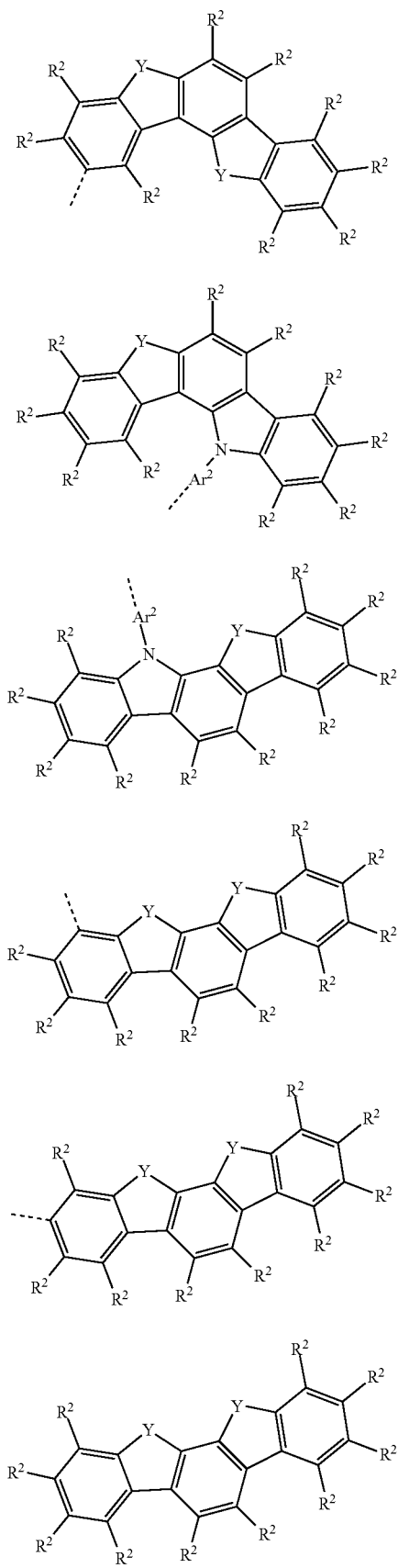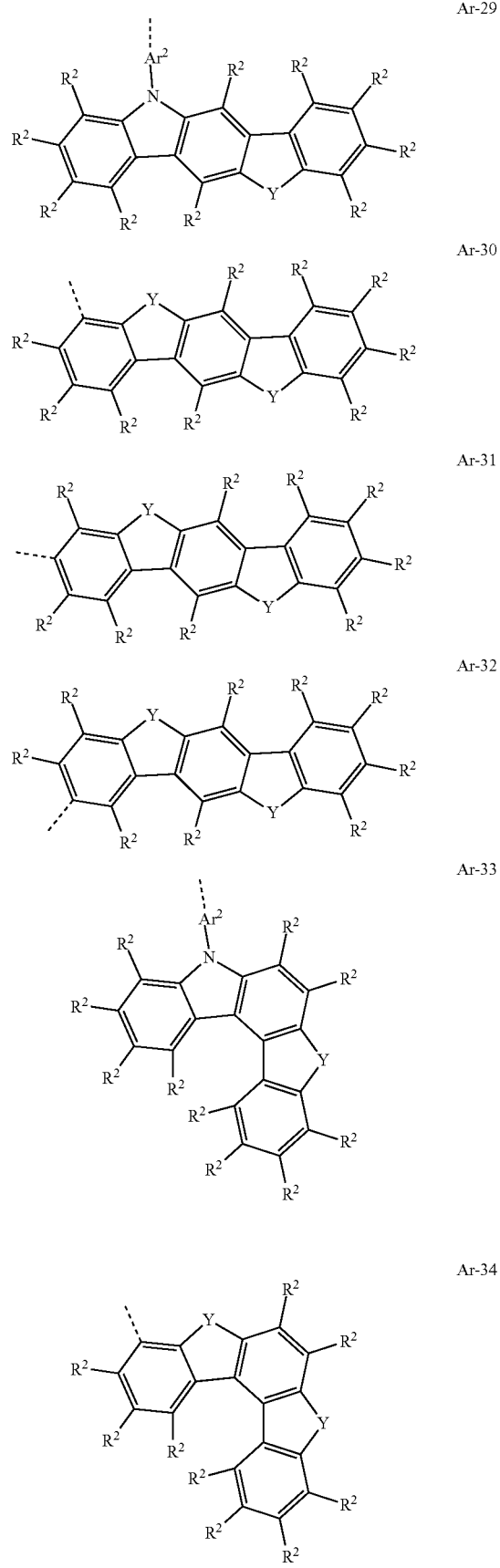

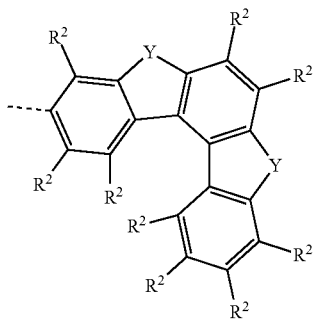
Ar-35
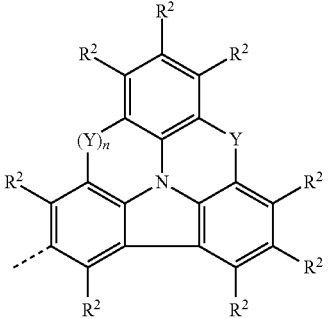
Ar-39
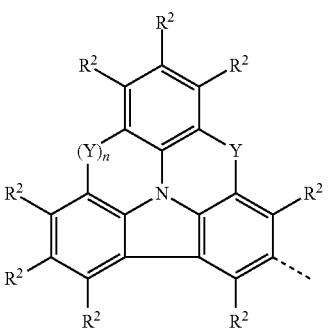
Ar-40
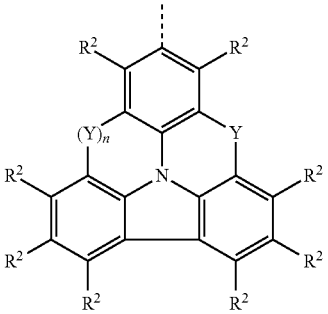
Ar-41
Ar-36
Ar-37
Ar-38
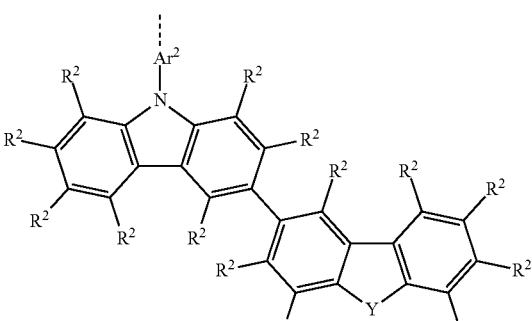
Ar-42
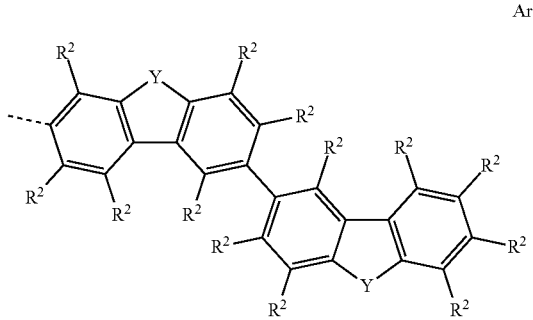
Ar-43

Ar-44
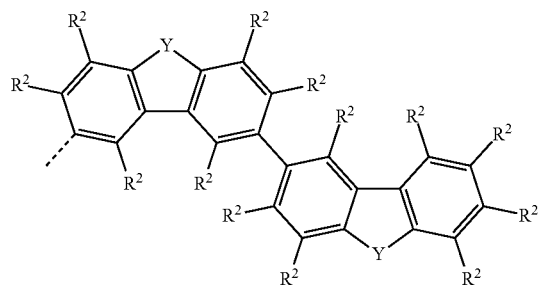
Ar-47
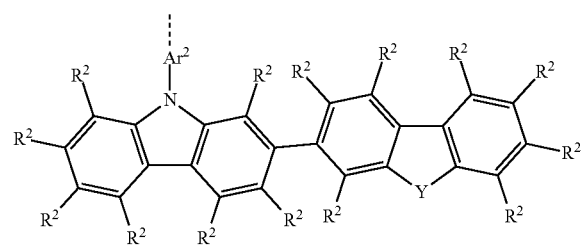
Ar-48
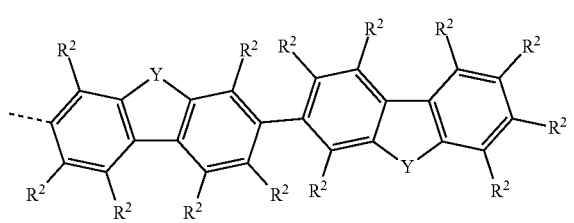
Ar-49
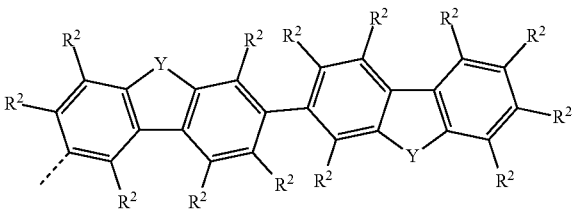
Ar-50
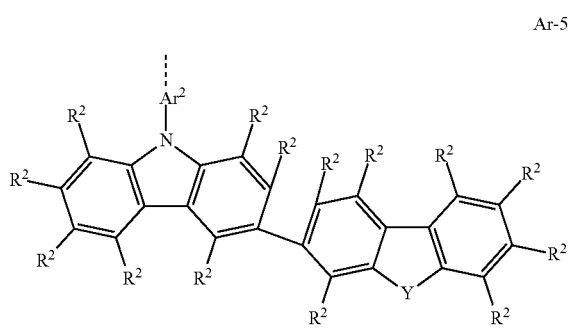
Ar-51
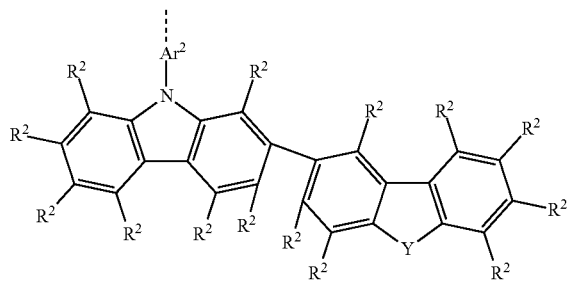
Ar-52
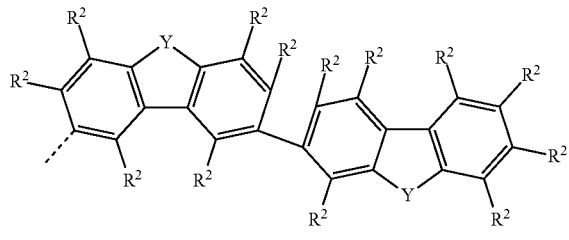
Ar-53
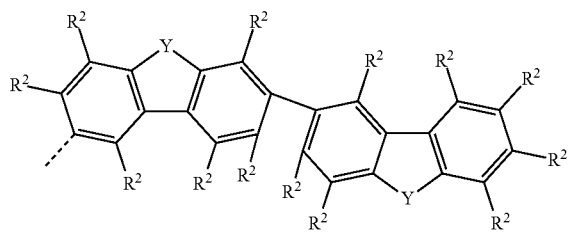
Ar-54
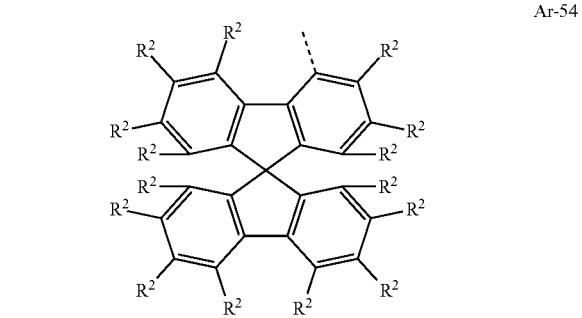
Ar-55
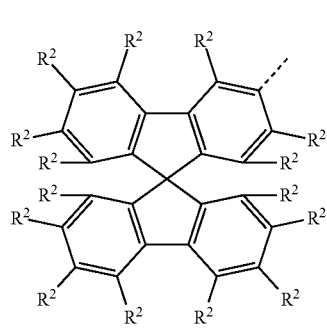

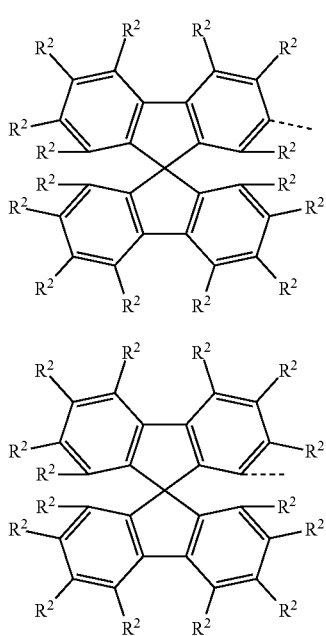

Ar-56

Ar-57 where $R^2$ has the definitions given above, the dotted bond represents the bond to the group of the formula (1) or (2) or (3) and, in addition:

$Ar^2$ is the same or different at each instance and is a bivalent aromatic or heteroaromatic ring system which has 6 to 18 aromatic ring atoms, does not contain any electron-deficient heteroaryl groups and may be substituted in each case by one or more $R^2$ radicals;

Y is the same or different at each instance and is $C(R^2)_2$, $NR^2$, O or S;

n is 0 or 1, where n=0 means that no Y group is bonded at this position and $R^2$ radicals thereof are bonded to the corresponding carbon atoms 35 instead.

When the abovementioned groups for Ar have two or more Y groups, possible options for these include all combinations from the definition of Y. Preference is given to groups in which one Y group is $NR^2$ and the other Y group is $C(R^2)_2$ or in which both Y groups are $NR^2$ or in which both Y groups are O.

In a further preferred embodiment of the invention, at least one Y group is $C(R^2)_2$ or $NR^2$.

When Y is $NR^2$, the substituent $R^2$ bonded to the nitrogen atom is preferably an aromatic or heteroaromatic ring system which has 5 to 24 aromatic ring atoms and may also be substituted by one or more $R^3$ radicals. In a particularly preferred embodiment, this substituent $R^2$ is the same or different at each instance and is an aromatic or heteroaromatic ring system which has 6 to 24 aromatic ring atoms, which does not have any fused aryl groups and which does not have any fused heteroaryl groups in which two or more aromatic or heteroaromatic 6-membered ring groups are fused directly to one another, and which may also be substituted in each case by one or more $R^3$ radicals. Particular preference is given to phenyl, biphenyl, terphenyl and quaterphenyl having linkage patterns as listed above for Ar-1 to Ar-11, these structures preferably being unsubstituted.

When Y is $C(R^2)_2$, $R^2$ is preferably the same or different at each instance is a linear alkyl group having 1 to 10 carbon atoms or a branched or cyclic alkyl group having 3 to 10 carbon atoms or an aromatic or heteroaromatic ring system having 5 to 24 aromatic ring atoms, which may also be substituted by one or more $R^3$ radicals. Most preferably, $R^2$ is a methyl group or a phenyl group. In this case, the $R^2$ radicals together may also form a ring system, which leads to a spiro system.

In a preferred embodiment of the invention, $Ar^2$ is ortho-, meta- or para-phenylene or a biphenyl group, each of which may be substituted by one or more $R^2$ radicals, but are preferably unsubstituted.

It may further be preferable when the Ar-1 to Ar-57 groups are bonded not directly to the nitrogen atom in formula (1) or formula (2) or formula (3), but via a bridging group. Preferred bridging groups are ortho-, meta- or para-phenylene or a biphenyl group, each of which may be substituted by one or more $R^2$ radicals, but are preferably unsubstituted.

In a preferred embodiment of the invention, $R^2$ is selected from the group consisting of H, D and an alkyl group having 1 to 10 carbon atoms, preferably 1 to 4 carbon atoms. More preferably, $R^2$ is H.

In a further preferred embodiment of the invention, Ar is a triarylamine group which may be substituted by one or more $R^1$ radicals. The latter is preferably selected from the structures of the following formula Ar-58:

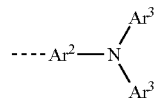

Ar-58 where the dotted bond indicates the linkage to the nitrogen atom, $Ar^2$ has the definition given above and $Ar^3$ is the same or different at each instance and is an aromatic or heteroaromatic ring system, preferably having 6 to 18 aromatic ring atoms, which does not contain any electron-deficient heteroaryl groups and may be substituted in each case by one or more $R^2$ radicals.

In a preferred embodiment of the invention, $R^1$ is the same or different at each instance and is selected from the group consisting of H, D, $N(Ar^1)_2$, a straight-chain alkyl group having 1 to 10 carbon atoms or a branched or cyclic alkyl group having 3 to 10 carbon atoms, each of which may be substituted by one or more $R^3$ radicals, where one or more hydrogen atoms may be replaced by D or F, or an aromatic or heteroaromatic ring system which has 5 to 30 aromatic ring atoms and may be substituted in each case by one or more $R^3$ radicals. More preferably, $R^1$ is the same or different at each instance and is selected from the group consisting of H, $N(Ar^1)_2$, a straight-chain alkyl group having 1 to 4 carbon atoms or a branched or cyclic alkyl group having 3 or 4 carbon atoms, each of which may be substituted by one or more $R^3$ radicals, or an aromatic or heteroaromatic ring system which has 5 to 18 aromatic ring atoms and may be substituted in each case by one or more $R^3$ radicals.

It is preferable here, when the Ar and $R^2$ groups together have fewer than 12 aromatic ring atoms, when at least one $R^1$ group, preferably exactly one $R^1$ group, is an $N(Ar^1)_2$ group or an aromatic or heteroaromatic ring system.

At the same time, in compounds of the formula (1) or the preferred embodiments (7) to (13), (7a) to (13a) and (7b) to (13b), preferably not more than one of the $R^1$ groups in each case is not H and the other $R^1$ groups are each H. In addition, in compounds of the formula (2) or (3) or the preferred embodiments (14), (15), (14a), (14b), (15a) and (15b), preferably not more than one of the R¹ groups bonded to the same cycle is not H and the other R¹ groups bonded to the same cycle are each H. It may also be preferable when all R¹ groups are H.

In a preferred embodiment of the formula (1) or the preferred embodiments, exactly one of the R¹ substituents is an N(Ar¹)₂ group or an aromatic or heteroaromatic ring system which has 5 to 24 aromatic ring atoms and may be substituted in each case by one or more R² radicals, and the other R¹ substituents are each H. In a preferred embodiment of the formulae (2) and (3) or the preferred embodiments, exactly one of the R¹ substituents that are bonded to the same cycle is an N(Ar¹)₂ group or an aromatic or heteroaromatic ring system which has 5 to 24 aromatic ring atoms and may be substituted in each case by one or more R² radicals, and the other R¹ substituents are each H.

When all R¹ radicals are H or D or alkyl, it is preferable when the Ar group is an aromatic or heteroaromatic ring system having at least 12 aromatic ring atoms.

When R¹ is an aromatic or heteroaromatic ring system, the R¹ groups are preferably selected from the R¹-1 to R¹-42 groups

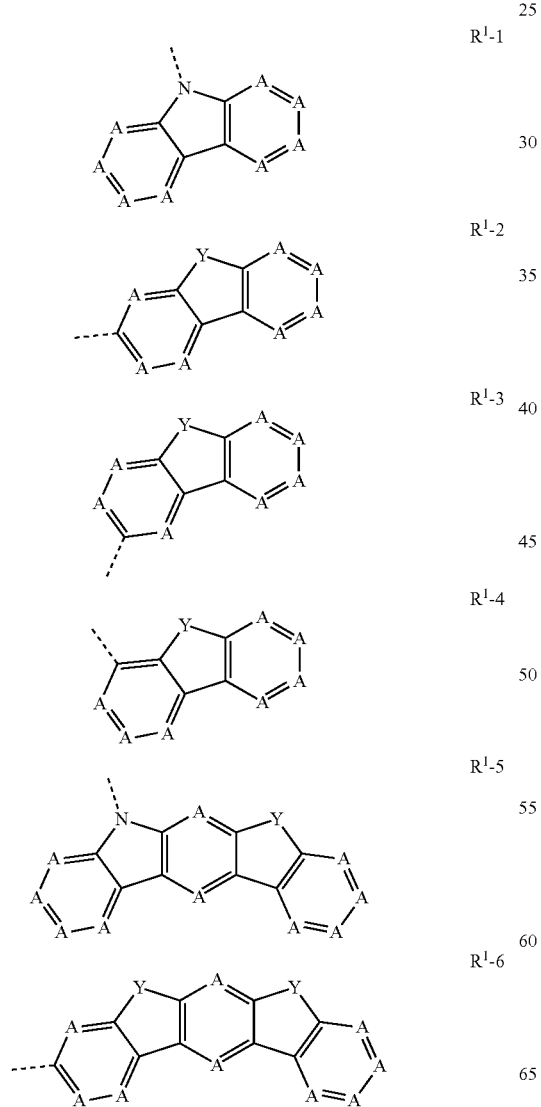

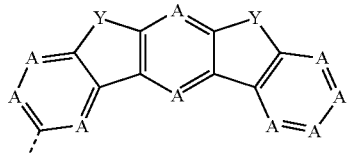

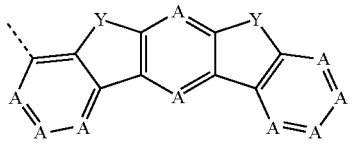

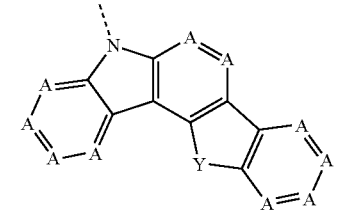

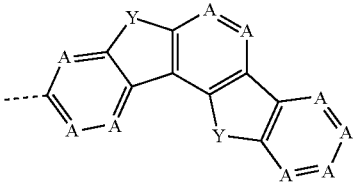

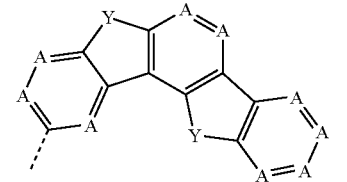

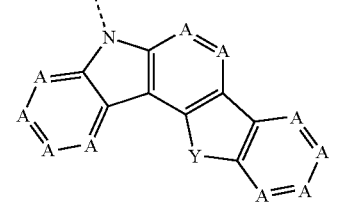

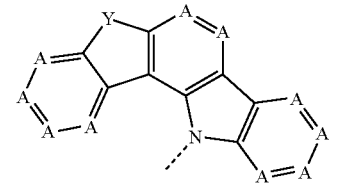

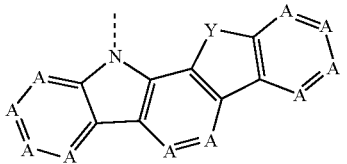

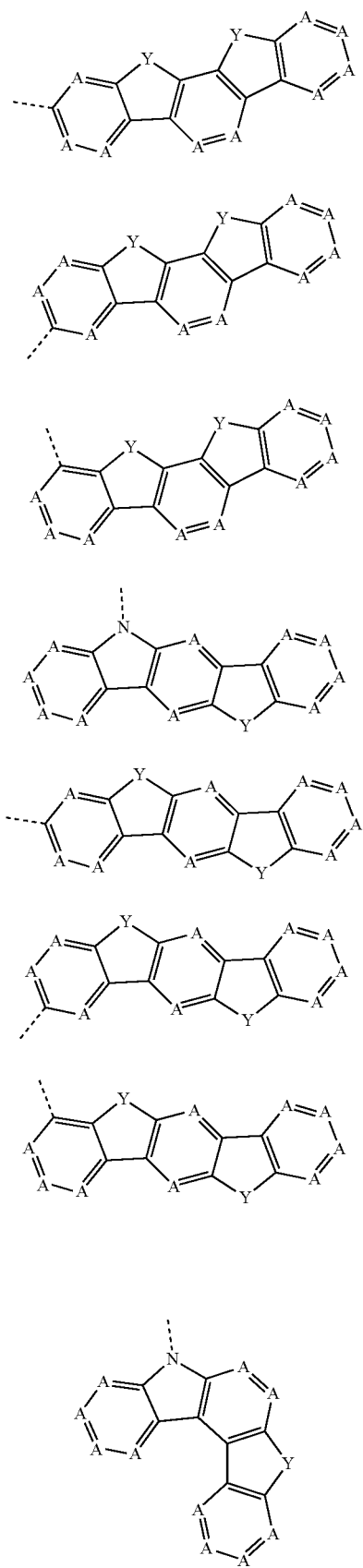
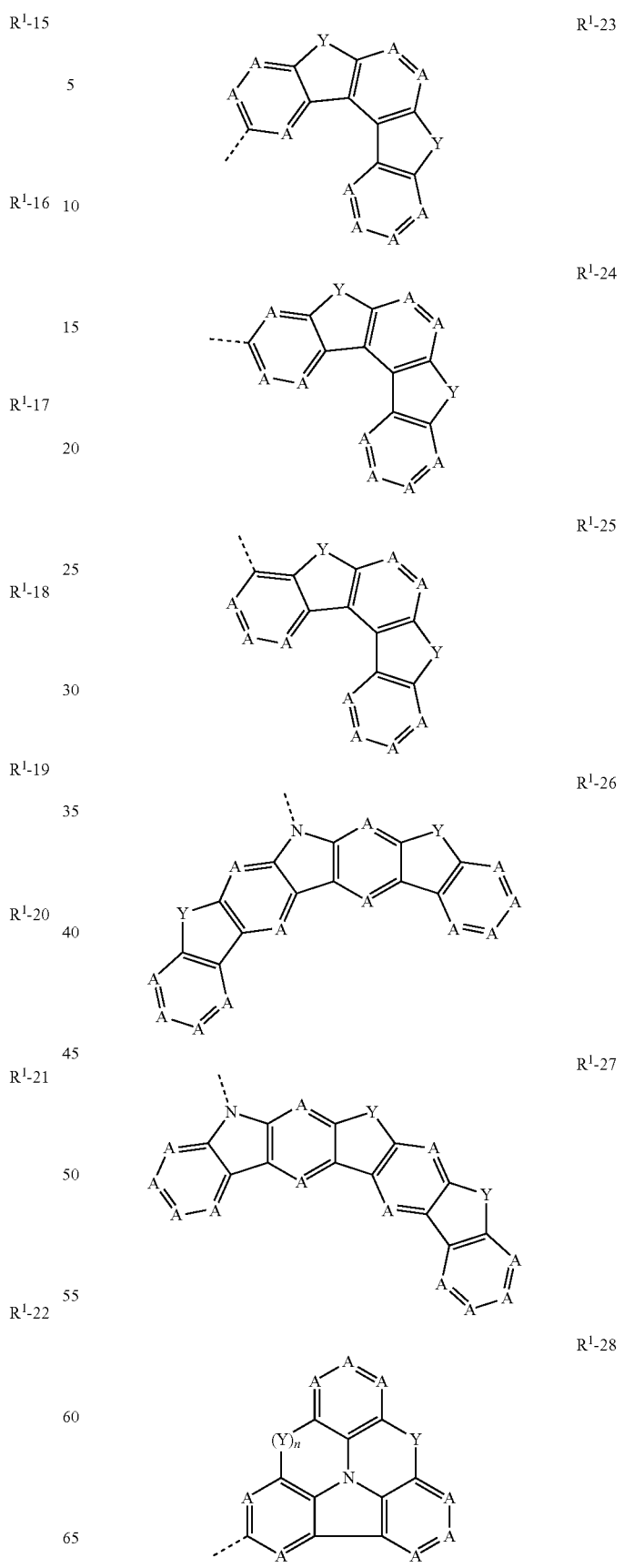

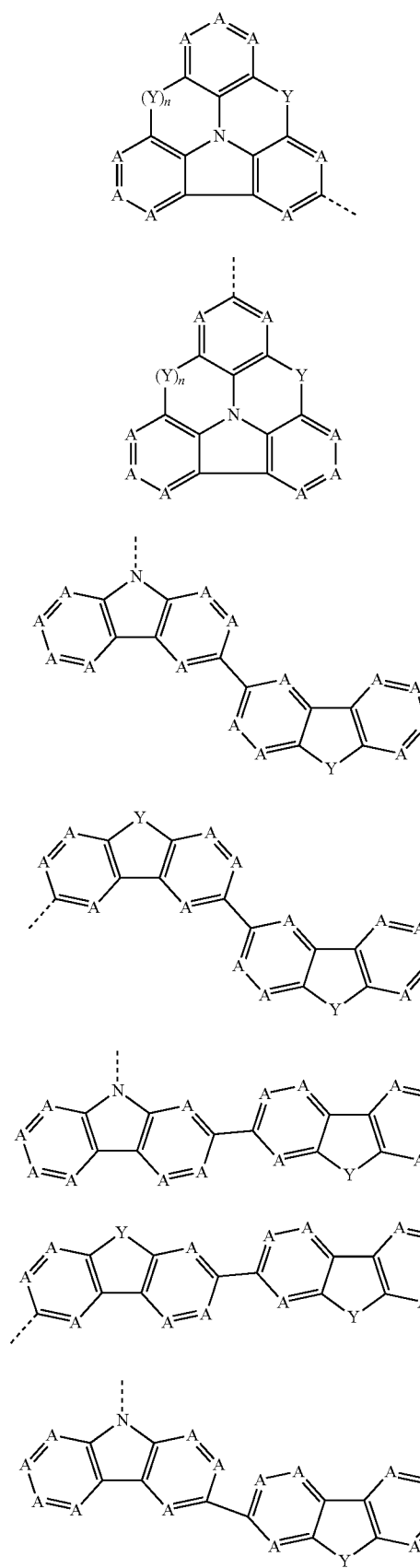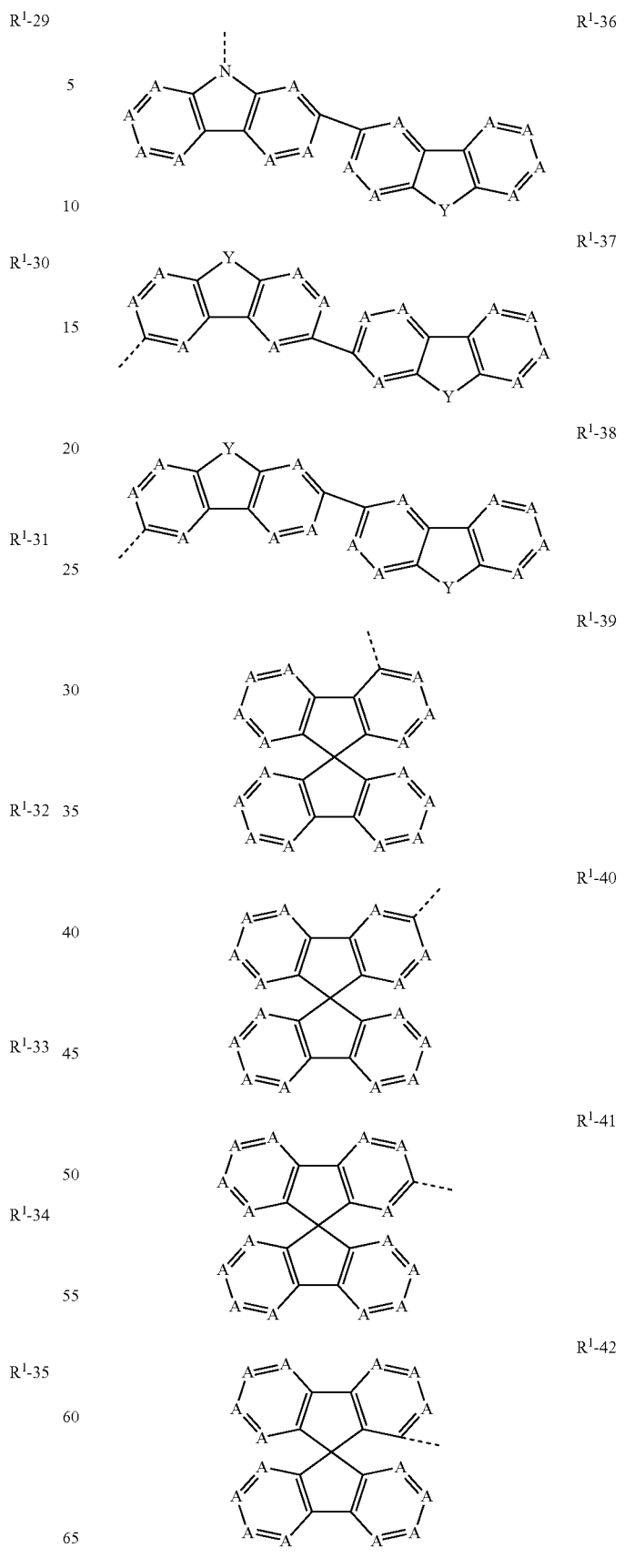

where $R^3$ has the definitions given above, the dotted bond represents the bond to the group of the formula (1) or (2) or (3) and, in addition:

A is the same or different at each instance and is $CR^3$ or N, where not more than 3 X symbols per cycle are N;

Y is the same or different at each instance and is $C(R^3)_2$, $NR^3$, O or S;

n is 0 or 1, where n=0 means that no Y group is bonded at this position and $R^3$ radicals thereof are bonded to the corresponding carbon atoms instead.

The expression "per cycle" mentioned above and also used hereinafter relates in the context of the present application to each individual ring present in the compound, i.e. to each individual 5- or 6-membered ring.

In preferred groups of the abovementioned formulae $R^1$-1 to $R^1$-42, not more than one A symbol per cycle is N. More preferably, the A symbol is the same or different at each instance and is $CR^3$, especially CH.

When the groups of the formulae $R^1$-1 to $R^1$-42 have two or more Y groups, possible options for these include all combinations from the definition of Y. Preference is given to groups in which one Y group is $NR^3$ and the other Y group is $C(R^3)_2$ or in which both Y groups are $NR^3$ or in which both Y groups are O.

When Y in the formulae $R^1$-1 to $R^1$-42 is $NR^3$, the $R^3$ substituent bonded to the nitrogen atom is preferably an aromatic or heteroaromatic ring system having 5 to 24 aromatic ring atoms. In a particularly preferred embodiment, this substituent $R^3$ is the same or different at each instance and is an aromatic or heteroaromatic ring system which has 6 to 24 aromatic ring atoms, which does not have any fused aryl groups and which does not have any fused heteroaryl groups in which two or more aromatic or heteroaromatic 6-membered ring groups are fused directly to one another. Particular preference is given to phenyl, biphenyl, terphenyl and quaterphenyl having linkage patterns as listed above for Ar-1 to Ar-11, these structures preferably being unsubstituted.

When Y in the formulae $R^1$-1 to $R^1$-42 is $C(R^3)_2$, $R^3$ is preferably the same or different at each instance and is a linear alkyl group having 1 to 10 carbon atoms or a branched or cyclic alkyl group having 3 to 10 carbon atoms or an aromatic or heteroaromatic ring system having 5 to 24 aromatic ring atoms. Most preferably, $R^3$ is a methyl group or a phenyl group. In this case, the $R^3$ radicals together may also form a ring system, which leads to a spiro system.

It may further be preferable when the $R^1$-1 to $R^1$-42 groups are bonded not directly to the nitrogen atom in formula (1) or formula (2) or formula (3), but via a bridging group. Preferred bridging groups are ortho-, meta- or para-phenylene or a biphenyl group, each of which may be substituted by one or more $R^3$ radicals, but are preferably unsubstituted.

In a further preferred embodiment of the invention, $R^1$ is a triarylamine group which may be substituted by one or more $R^1$ radicals. The latter is preferably selected from the structures of the following formula $R^1$-43:

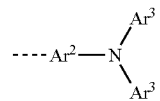

$R^1$-43 where the dotted bond indicates the linkage to the carbon atom in the base skeleton and $Ar^2$ and $Ar^3$ are an aromatic or heteroaromatic ring system which has 5 to 14 aromatic ring atoms and may be substituted in each case by one or more $R^3$ radicals.

At the same time, in compounds which are processed by vacuum evaporation, the alkyl groups preferably have not more than five carbon atoms, more preferably not more than 4 carbon atoms, most preferably not more than 1 carbon atom. For compounds which are processed from solution, suitable compounds are also those substituted by alkyl groups, especially branched alkyl groups, having up to 10 carbon atoms or those substituted by oligoarylene groups, for example ortho-, meta-, para- or branched terphenyl or quaterphenyl groups.

The abovementioned preferred embodiments may be combined with one another as desired. In a particularly preferred embodiment of the invention, the abovementioned preferences occur simultaneously.

When the compounds of the formula (1) or formula (2) or formula (3) or the preferred embodiments are used as matrix material for a phosphorescent emitter or in a layer directly adjoining a phosphorescent layer, it is further preferable when the compound does not contain any fused aryl or heteroaryl groups in which more than two six-membered rings are fused directly to one another. It is especially preferable when the R, $R^1$, $R^2$ and Ar radicals do not contain any fused aryl or heteroaryl group in which two or more six-membered rings are fused directly to one another.

Examples of suitable compounds according to the above-detailed embodiments are the compounds detailed in the following table:

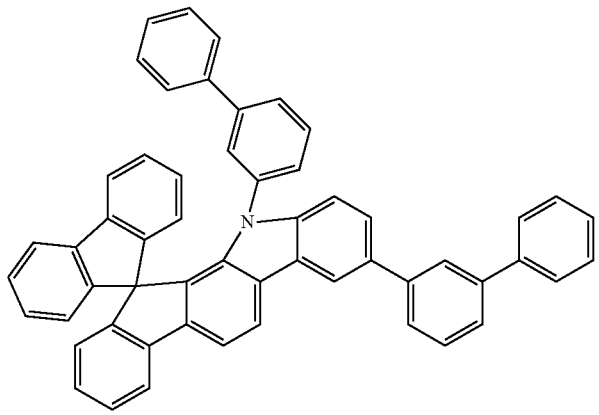 [SMILES: c1ccc(-c2cccc(-c3ccc4c(c3)c3ccc5c(c3n4-c3cccc(-c4ccccc4)c3)C3(c4ccccc4-c4ccccc43)c3ccccc3-5)c2)cc1]

-continued
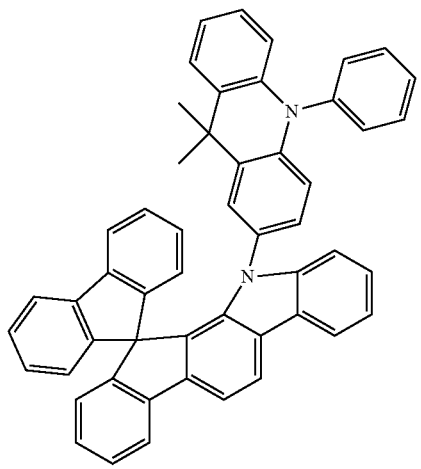 [SMILES: CC1(C)c2ccccc2N(c2ccccc2)c2ccc(-n3c4ccccc4c4ccc5c(c43)C3(c4ccccc4-c4ccccc43)c3ccccc3-5)cc21]
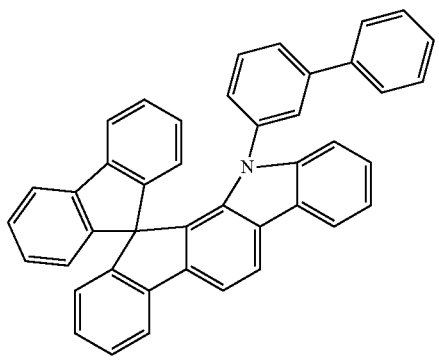 [SMILES: c1ccc(-c2cccc(-n3c4ccccc4c4ccc5c(c43)C3(c4ccccc4-c4ccccc43)c3ccccc3-5)c2)cc1]
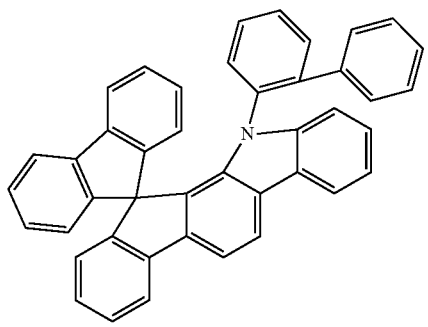 [SMILES: c1ccc(-c2ccccc2-n2c3ccccc3c3ccc4c(c32)C2(c3ccccc3-c3ccccc32)c2ccccc2-4)cc1]
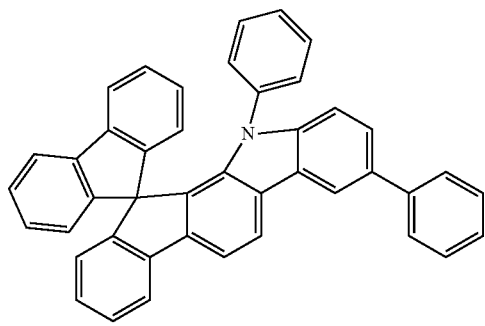 [SMILES: c1ccc(-c2ccc3c(c2)c2ccc4c(c2n3-c2ccccc2)C2(c3ccccc3-c3ccccc32)c2ccccc2-4)cc1]

-continued
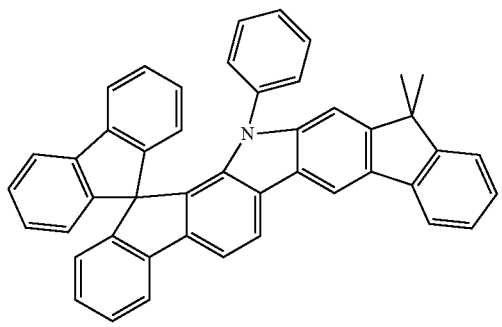 [SMILES: CC1(C)c2ccccc2-c2cc3c4ccc5c(c4n(-c4ccccc4)c3cc21)C1(c2ccccc2-c2ccccc21)c1ccccc1-5]
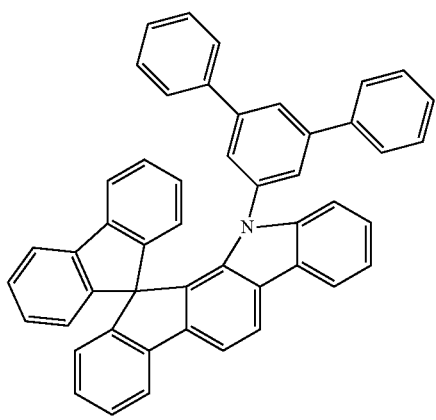 [SMILES: c1ccc(-c2cc(-c3ccccc3)cc(-n3c4ccccc4c4ccc5c(c43)C3(c4ccccc4-c4ccccc43)c3ccccc3-5)c2)cc1]
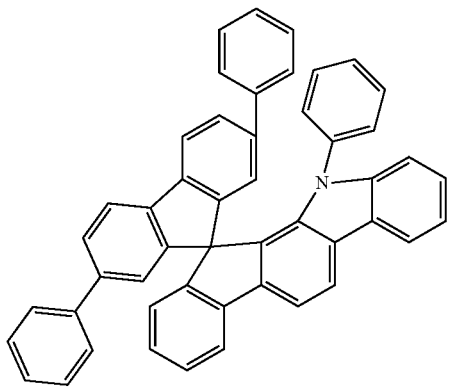 [SMILES: c1ccc(-c2ccc3c(c2)C2(c4cc(-c5ccccc5)ccc4-3)c3ccccc3-c3ccc4c5ccccc5n(-c5ccccc5)c4c32)cc1]
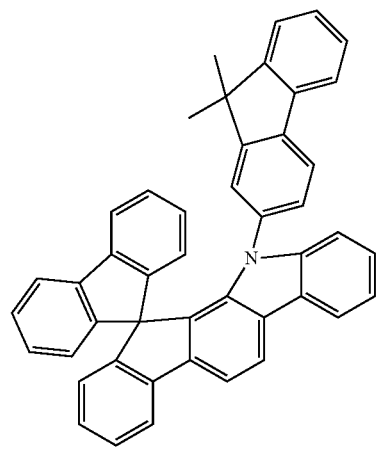 [SMILES: CC1(C)c2ccccc2-c2ccc(-n3c4ccccc4c4ccc5c(c43)C3(c4ccccc4-c4ccccc43)c3ccccc3-5)cc21]

-continued
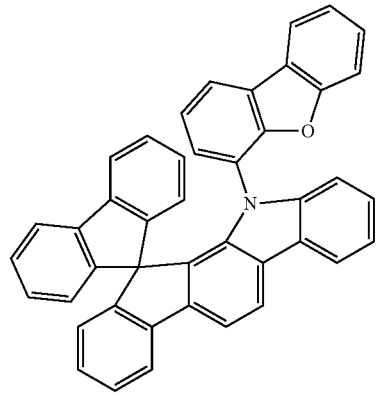 [SMILES: c1ccc2c(c1)-c1ccccc1C21c2ccccc2-c2ccc3c4ccccc4n(-c4cccc5c4oc4ccccc45)c3c21]
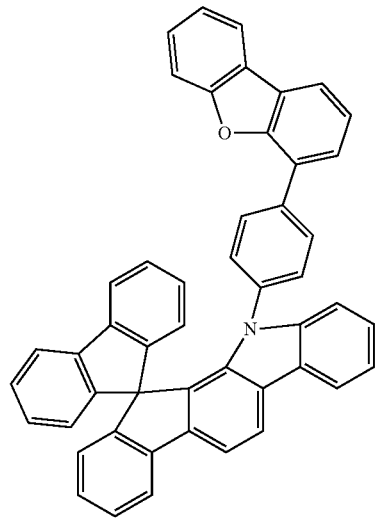 [SMILES: c1ccc2c(c1)-c1ccccc1C21c2ccccc2-c2ccc3c4ccccc4n(-c4ccc(-c5cccc6c5oc5ccccc56)cc4)c3c21]
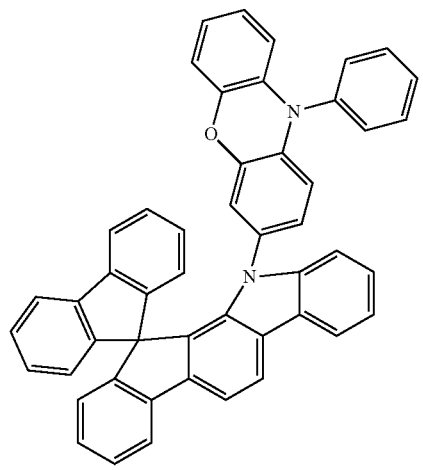 [SMILES: c1ccc(N2c3ccccc3Oc3cc(-n4c5ccccc5c5ccc6c(c54)C4(c5ccccc5-c5ccccc54)c4ccccc4-6)ccc32)cc1]

-continued
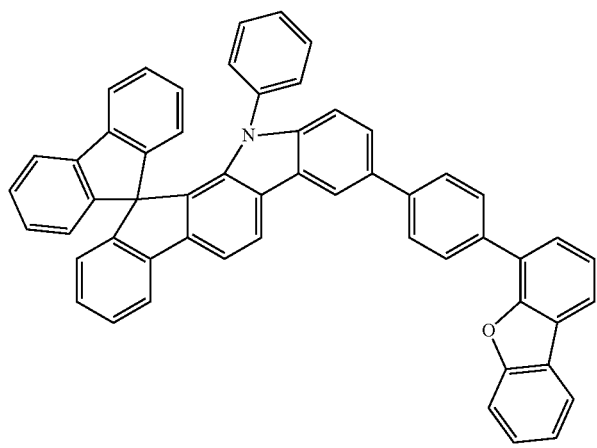 [SMILES: c1ccc(-n2c3ccc(-c4ccc(-c5cccc6c5oc5ccccc56)cc4)cc3c3ccc4c(c32)C2(c3ccccc3-c3ccccc32)c2ccccc2-4)cc1]
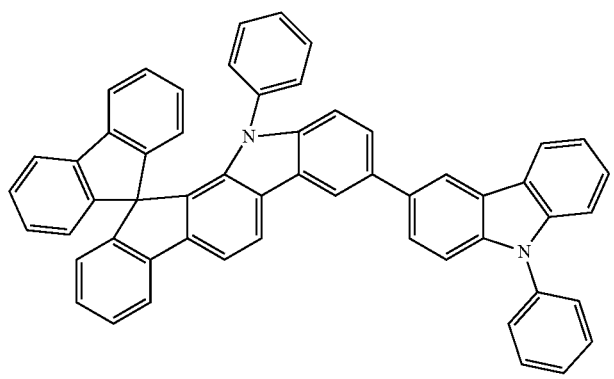 [SMILES: c1ccc(-n2c3ccccc3c3cc(-c4ccc5c(c4)c4ccc6c(c4n5-c4ccccc4)C4(c5ccccc5-c5ccccc54)c4ccccc4-6)ccc32)cc1]
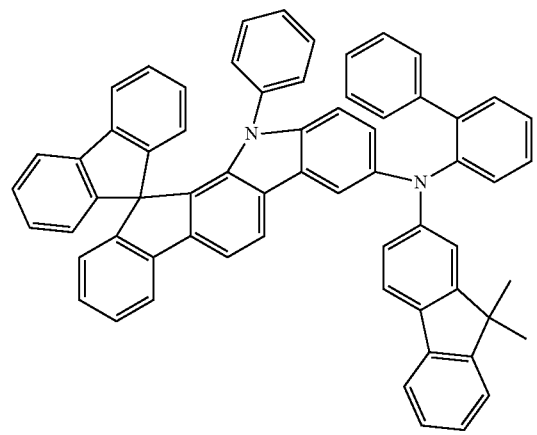 [SMILES: CC1(C)c2ccccc2-c2ccc(N(c3ccc4c(c3)c3ccc5c(c3n4-c3ccccc3)C3(c4ccccc4-c4ccccc43)c3ccccc3-5)c3ccccc3-c3ccccc3)cc21]
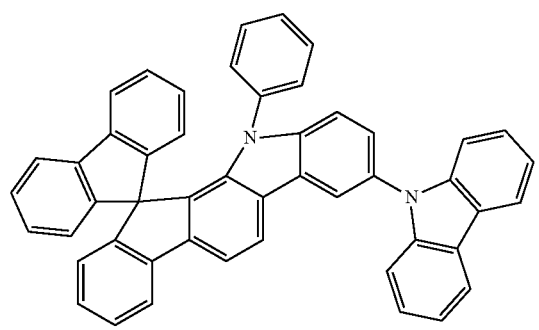 [SMILES: c1ccc(-n2c3ccc(-n4c5ccccc5c5ccccc54)cc3c3ccc4c(c32)C2(c3ccccc3-c3ccccc32)c2ccccc2-4)cc1]

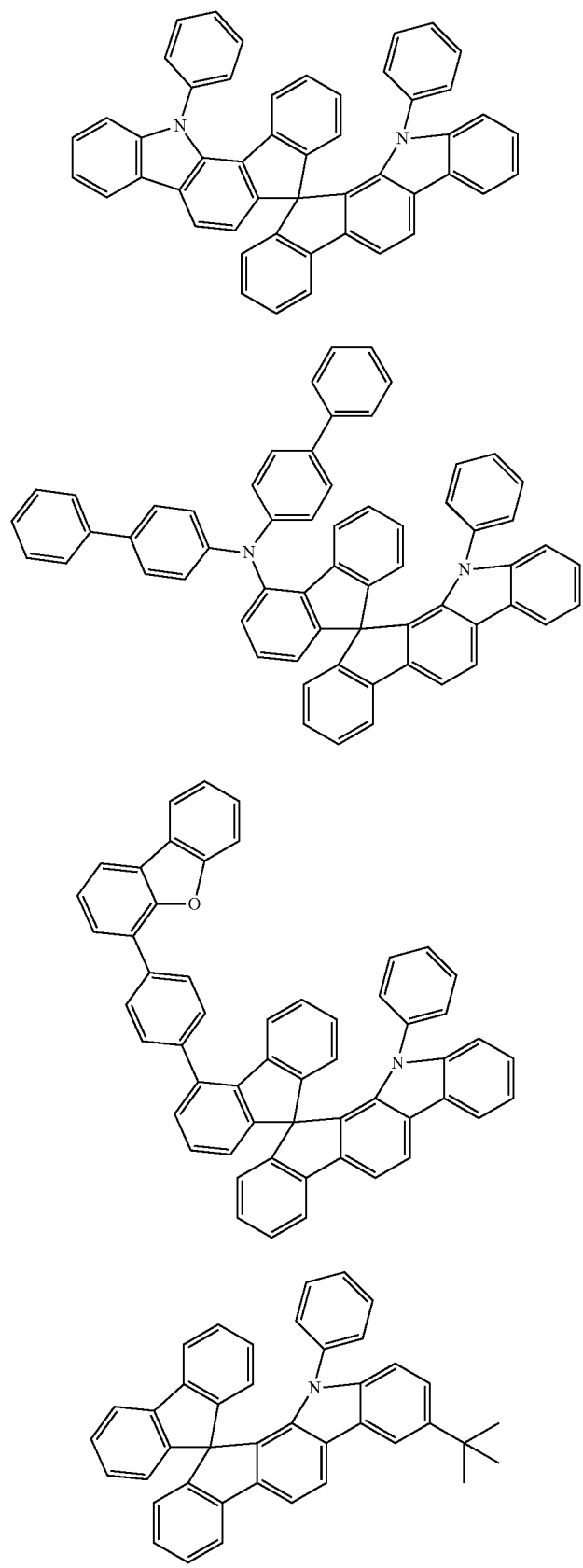

-continued
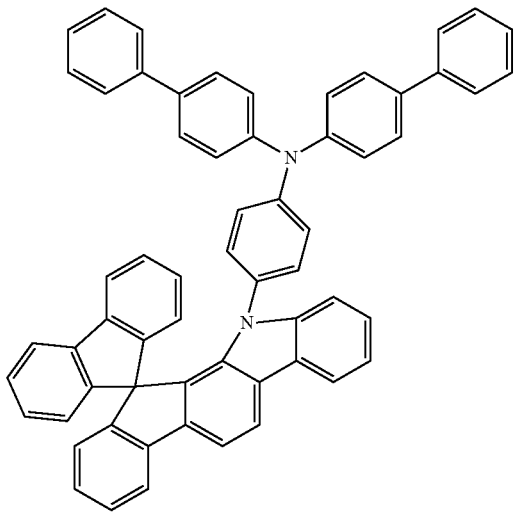 [SMILES: c1ccc(-c2ccc(N(c3ccc(-c4ccccc4)cc3)c3ccc(-n4c5ccccc5c5ccc6c(c54)C4(c5ccccc5-c5ccccc54)c4ccccc4-6)cc3)cc2)cc1]
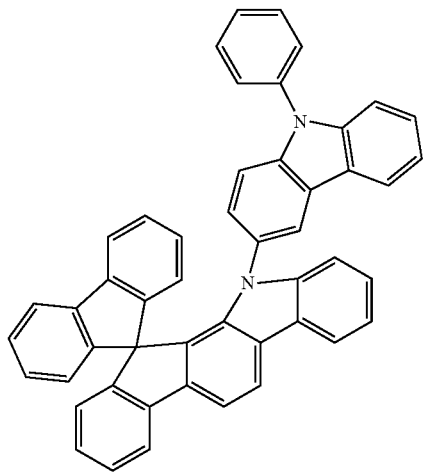 [SMILES: c1ccc(-n2c3ccccc3c3cc(-n4c5ccccc5c5ccc6c(c54)C4(c5ccccc5-c5ccccc54)c4ccccc4-6)ccc32)cc1]
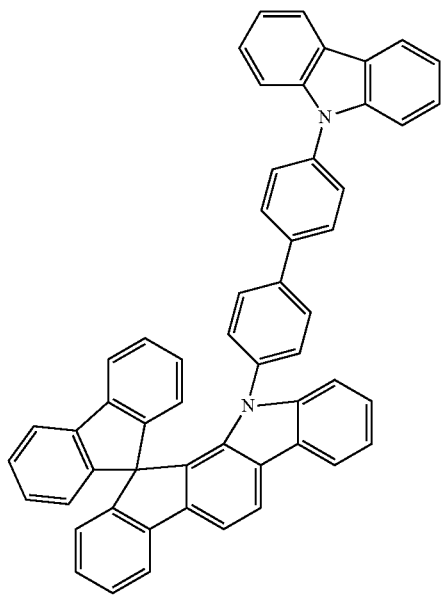 [SMILES: c1ccc2c(c1)-c1ccccc1C21c2ccccc2-c2ccc3c4ccccc4n(-c4ccc(-c5ccc(-n6c7ccccc7c7ccccc76)cc5)cc4)c3c21]

-continued
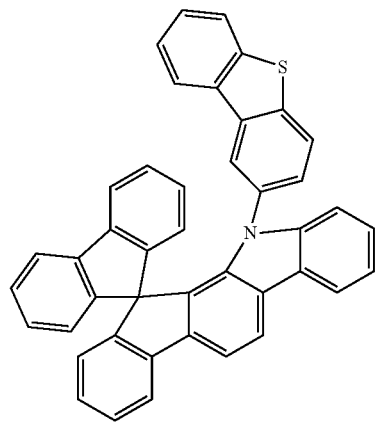 [SMILES: c1ccc2c(c1)-c1ccccc1C21c2ccccc2-c2ccc3c4ccccc4n(-c4ccc5sc6ccccc6c5c4)c3c21]
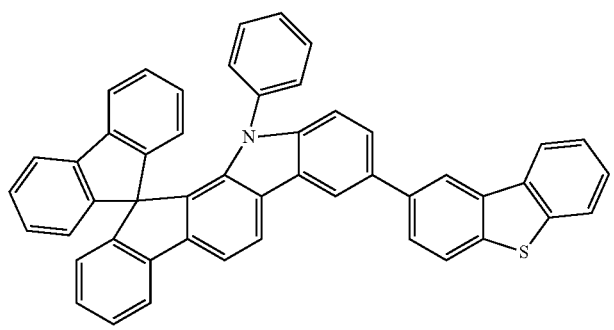 [SMILES: c1ccc(-n2c3ccc(-c4ccc5sc6ccccc6c5c4)cc3c3ccc4c(c32)C2(c3ccccc3-c3ccccc32)c2ccccc2-4)cc1]
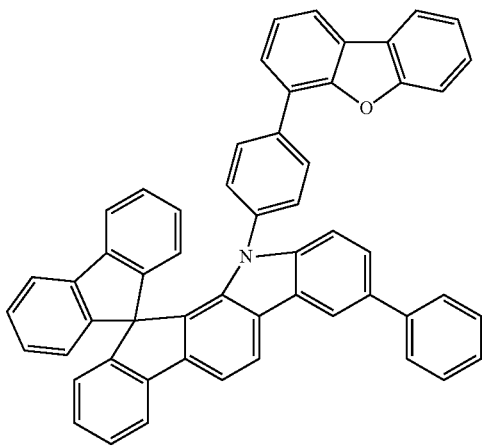 [SMILES: c1ccc(-c2ccc3c(c2)c2ccc4c(c2n3-c2ccc(-c3cccc5c3oc3ccccc35)cc2)C2(c3ccccc3-c3ccccc32)c2ccccc2-4)cc1]

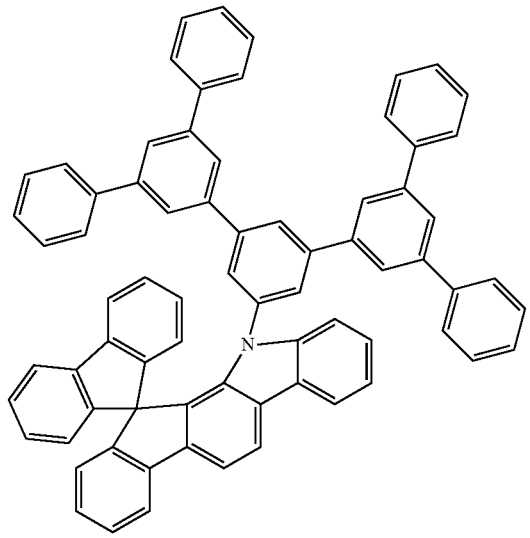 [SMILES: c1ccc(-c2cc(-c3ccccc3)cc(-c3cc(-c4cc(-c5ccccc5)cc(-c5ccccc5)c4)cc(-n4c5ccccc5c5ccc6c(c54)C4(c5ccccc5-c5ccccc54)c4ccccc4-6)c3)c2)cc1]
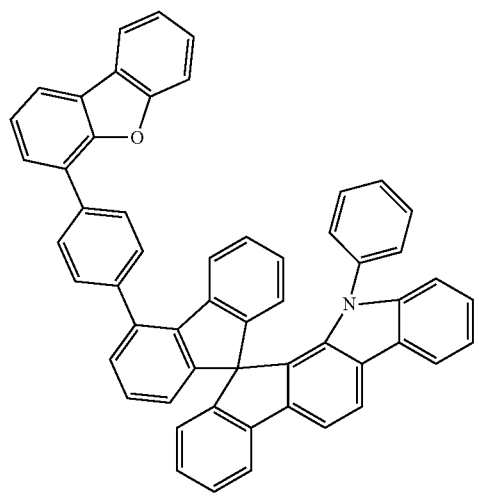 [SMILES: c1ccc(-n2c3ccccc3c3ccc4c(c32)C2(c3ccccc3-4)c3ccccc3-c3c(-c4ccc(-c5cccc6c5oc5ccccc56)cc4)cccc32)cc1]
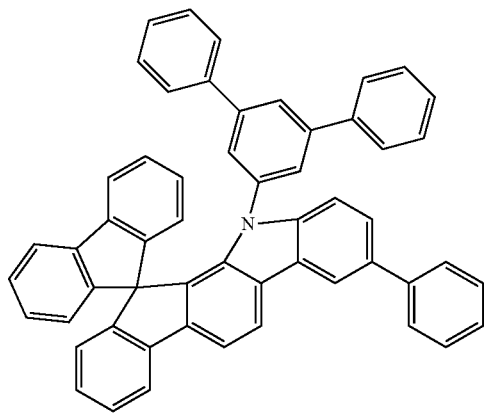 [SMILES: c1ccc(-c2cc(-c3ccccc3)cc(-n3c4ccc(-c5ccccc5)cc4c4ccc5c(c43)C3(c4ccccc4-c4ccccc43)c3ccccc3-5)c2)cc1]

-continued
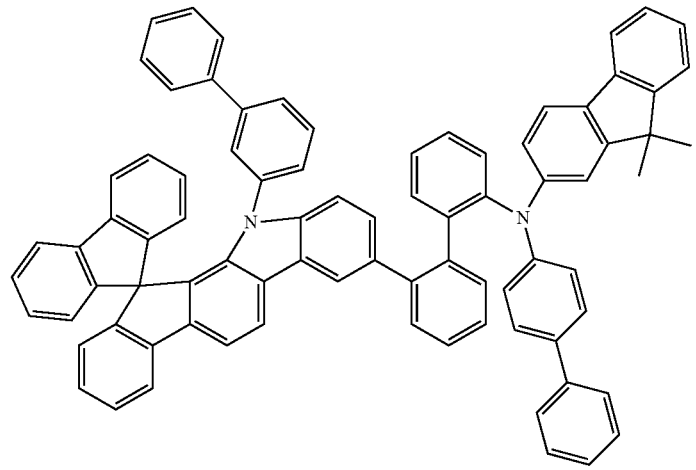 [SMILES: CC1(C)c2ccccc2-c2ccc(N(c3ccc(-c4ccccc4)cc3)c3ccccc3-c3ccccc3-c3ccc4c(c3)c3ccc5c(c3n4-c3cccc(-c4ccccc4)c3)C3(c4ccccc4-c4ccccc43)c3ccccc3-5)cc21]
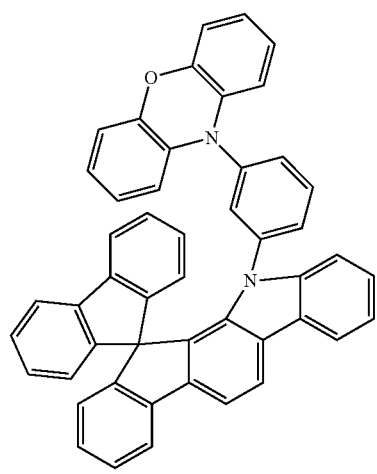 [SMILES: c1cc(N2c3ccccc3Oc3ccccc32)cc(-n2c3ccccc3c3ccc4c(c32)C2(c3ccccc3-c3ccccc32)c2ccccc2-4)c1]
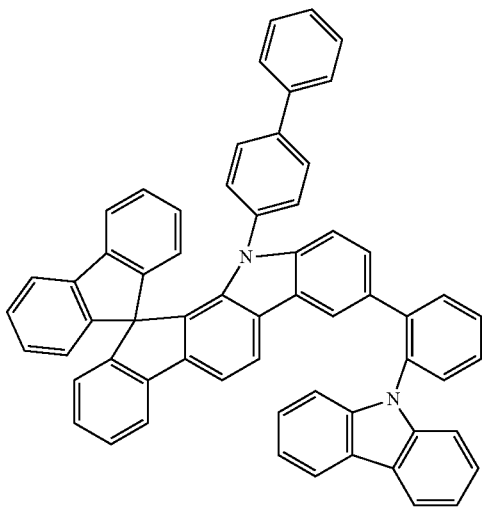 [SMILES: c1ccc(-c2ccc(-n3c4ccc(-c5ccccc5-n5c6ccccc6c6ccccc65)cc4c4ccc5c(c43)C3(c4ccccc4-c4ccccc43)c3ccccc3-5)cc2)cc1]

-continued
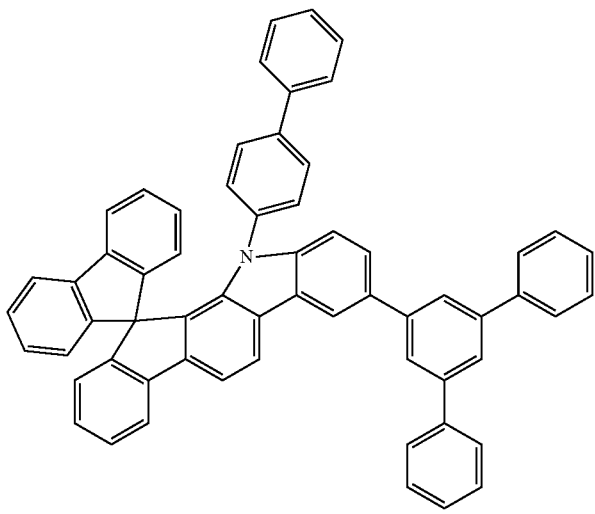 [SMILES: c1ccc(-c2ccc(-n3c4ccc(-c5cc(-c6ccccc6)cc(-c6ccccc6)c5)cc4c4ccc5c(c43)C3(c4ccccc4-c4ccccc43)c3ccccc3-5)cc2)cc1]
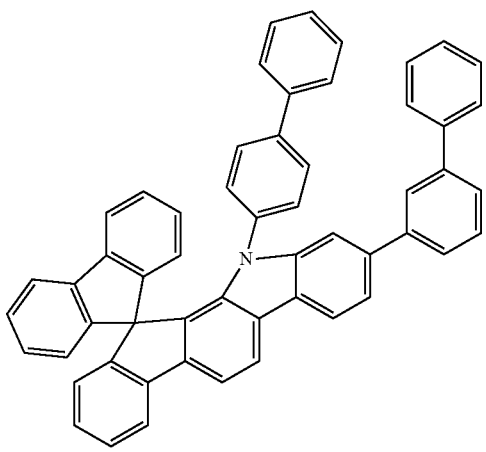 [SMILES: c1ccc(-c2ccc(-n3c4cc(-c5cccc(-c6ccccc6)c5)ccc4c4ccc5c(c43)C3(c4ccccc4-c4ccccc43)c3ccccc3-5)cc2)cc1]
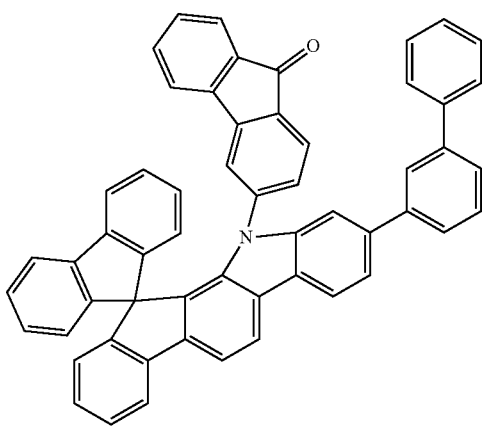 [SMILES: O=C1c2ccccc2-c2cc(-n3c4cc(-c5cccc(-c6ccccc6)c5)ccc4c4ccc5c(c43)C3(c4ccccc4-c4ccccc43)c3ccccc3-5)ccc21]

-continued
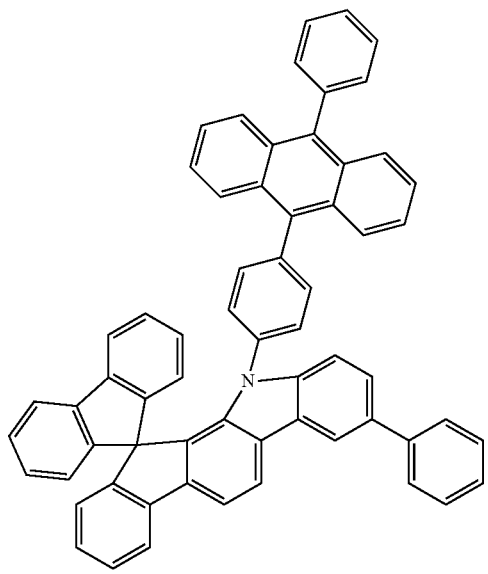 [SMILES: c1ccc(-c2ccc3c(c2)c2ccc4c(c2n3-c2ccc(-c3c5ccccc5c(-c5ccccc5)c5ccccc35)cc2)C2(c3ccccc3-c3ccccc32)c2ccccc2-4)cc1]
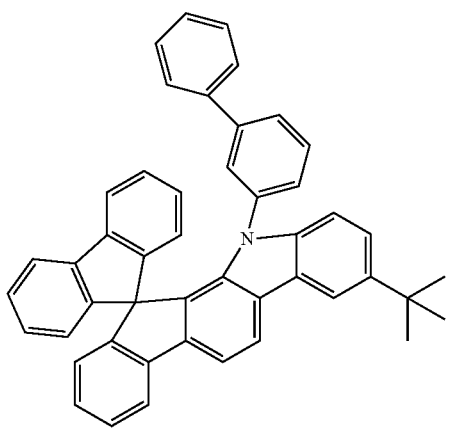 [SMILES: CC(C)(C)c1ccc2c(c1)c1ccc3c(c1n2-c1cccc(-c2ccccc2)c1)C1(c2ccccc2-c2ccccc21)c1ccccc1-3]
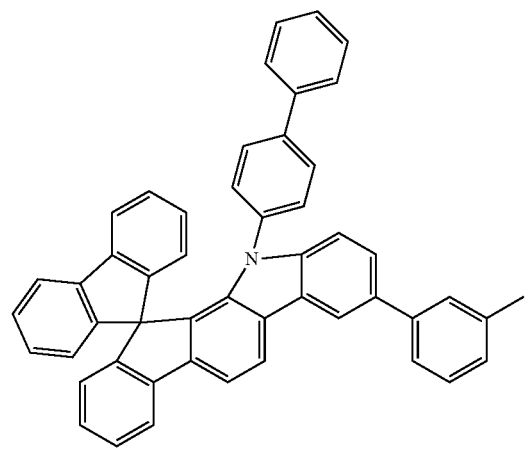 [SMILES: Cc1cccc(-c2ccc3c(c2)c2ccc4c(c2n3-c2ccc(-c3ccccc3)cc2)C2(c3ccccc3-c3ccccc32)c2ccccc2-4)c1]

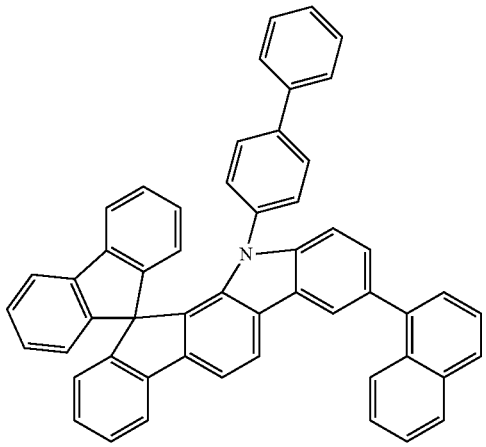 [SMILES: c1ccc(-c2ccc(-n3c4ccc(-c5cccc6ccccc56)cc4c4ccc5c(c43)C3(c4ccccc4-c4ccccc43)c3ccccc3-5)cc2)cc1]
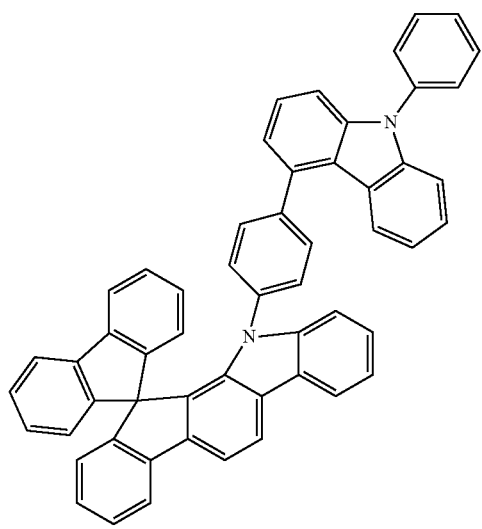 [SMILES: c1ccc(-n2c3ccccc3c3c(-c4ccc(-n5c6ccccc6c6ccc7c(c65)C5(c6ccccc6-c6ccccc65)c5ccccc5-7)cc4)cccc32)cc1]
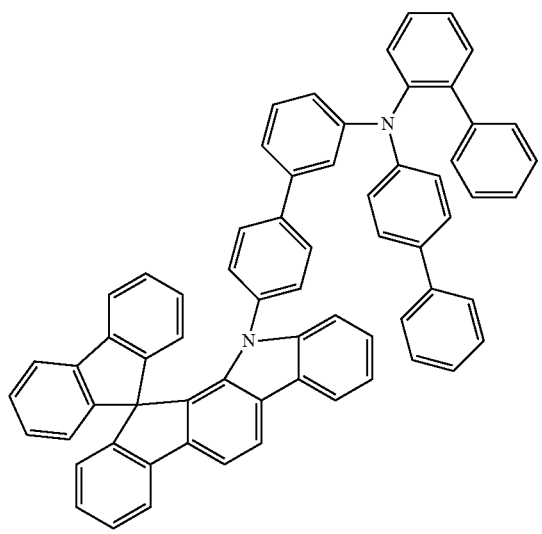 [SMILES: c1ccc(-c2ccc(N(c3cccc(-c4ccc(-n5c6ccccc6c6ccc7c(c65)C5(c6ccccc6-c6ccccc65)c5ccccc5-7)cc4)c3)c3ccccc3-c3ccccc3)cc2)cc1]

-continued
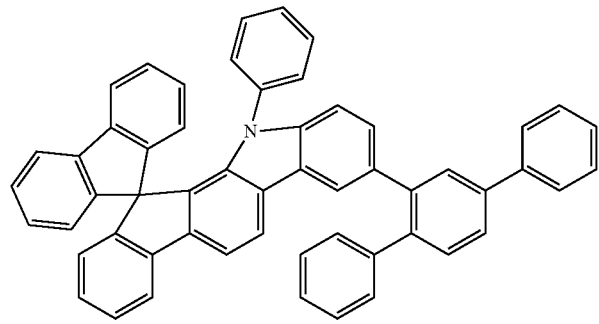 [SMILES: c1ccc(-c2ccc(-c3ccccc3)c(-c3ccc4c(c3)c3ccc5c(c3n4-c3ccccc3)C3(c4ccccc4-c4ccccc43)c3ccccc3-5)c2)cc1]
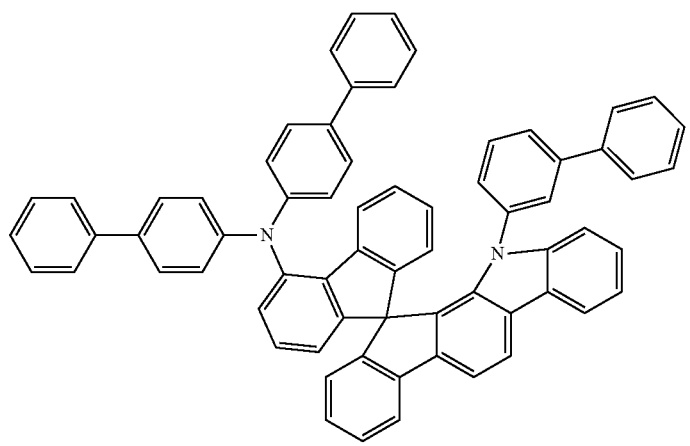 [SMILES: c1ccc(-c2ccc(N(c3ccc(-c4ccccc4)cc3)c3cccc4c3-c3ccccc3C43c4ccccc4-c4ccc5c6ccccc6n(-c6cccc(-c7ccccc7)c6)c5c43)cc2)cc1]
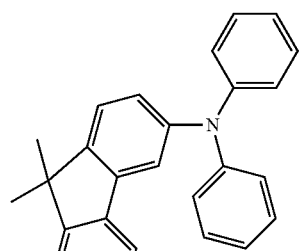
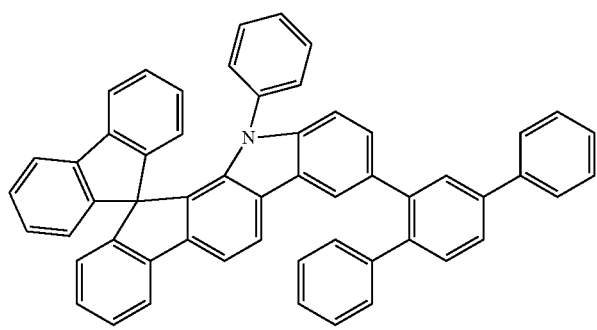 [SMILES: c1ccc(-c2ccc(-c3ccccc3)c(-c3ccc4c(c3)c3ccc5c(c3n4-c3ccccc3)C3(c4ccccc4-c4ccccc43)c3ccccc3-5)c2)cc1]

-continued
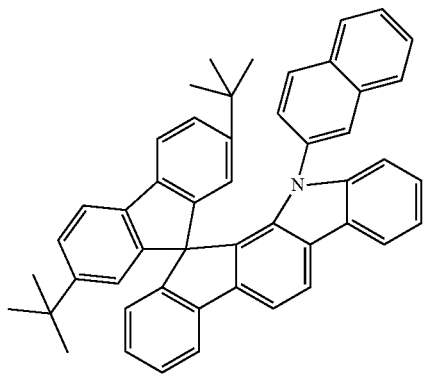 [SMILES: CC(C)(C)c1ccc2c(c1)C1(c3cc(C(C)(C)C)ccc3-2)c2ccccc2-c2ccc3c4ccccc4n(-c4ccc5ccccc5c4)c3c21]
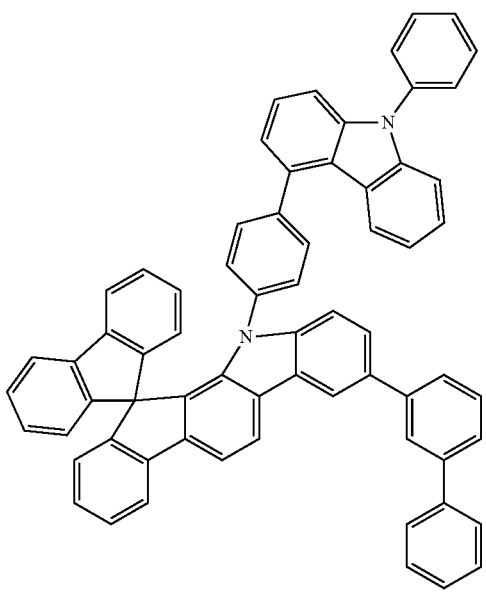 [SMILES: c1ccc(-c2cccc(-c3ccc4c(c3)c3ccc5c(c3n4-c3ccc(-c4cccc6c4c4ccccc4n6-c4ccccc4)cc3)C3(c4ccccc4-c4ccccc43)c3ccccc3-5)c2)cc1]
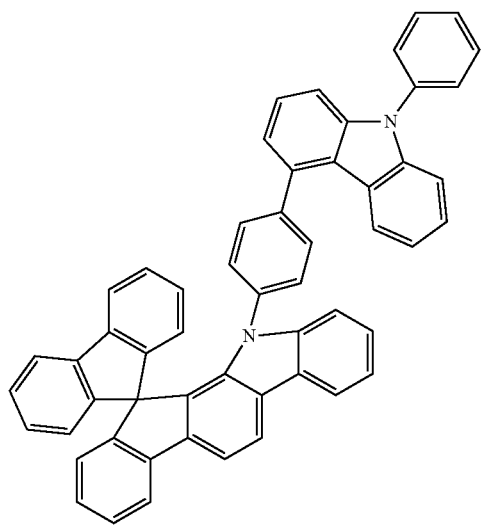 [SMILES: c1ccc(-n2c3ccccc3c3c(-c4ccc(-n5c6ccccc6c6ccc7c(c65)C5(c6ccccc6-c6ccccc65)c5ccccc5-7)cc4)cccc32)cc1]

-continued
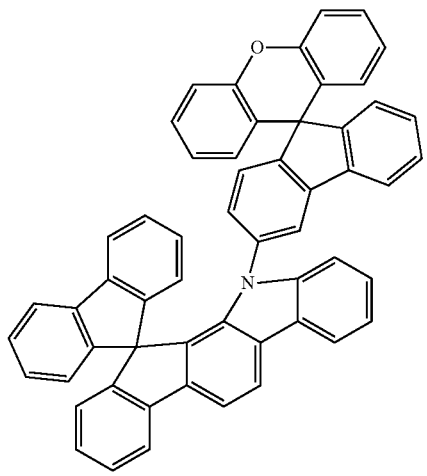 [SMILES: c1ccc2c(c1)Oc1ccccc1C21c2ccccc2-c2cc(-n3c4ccccc4c4ccc5c(c43)C3(c4ccccc4-c4ccccc43)c3ccccc3-5)ccc21]
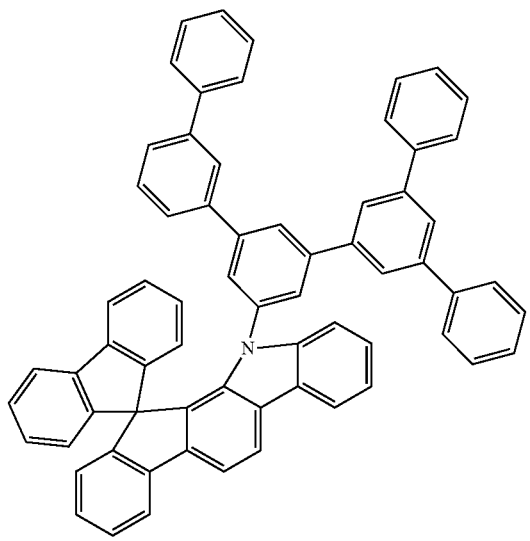 [SMILES: c1ccc(-c2cccc(-c3cc(-c4cc(-c5ccccc5)cc(-c5ccccc5)c4)cc(-n4c5ccccc5c5ccc6c(c54)C4(c5ccccc5-c5ccccc54)c4ccccc4-6)c3)c2)cc1]
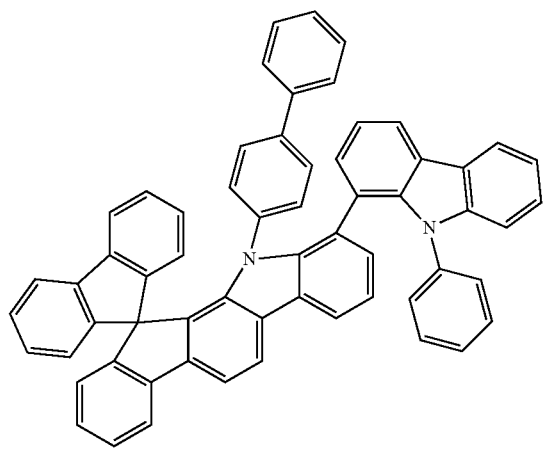 [SMILES: c1ccc(-c2ccc(-n3c4c(-c5cccc6c7ccccc7n(-c7ccccc7)c56)cccc4c4ccc5c(c43)C3(c4ccccc4-c4ccccc43)c3ccccc3-5)cc2)cc1]

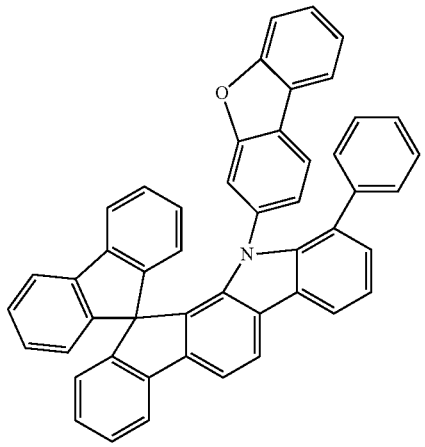 [SMILES: c1ccc(-c2cccc3c4ccc5c(c4n(-c4ccc6c(c4)oc4ccccc46)c23)C2(c3ccccc3-c3ccccc32)c2ccccc2-5)cc1]
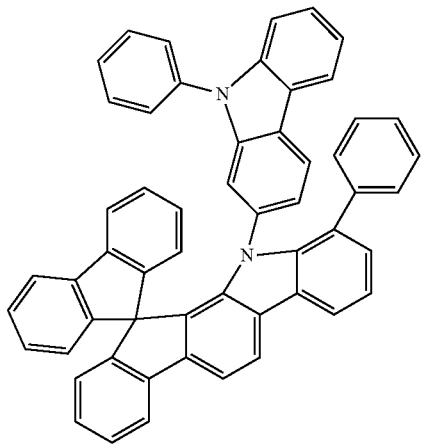 [SMILES: c1ccc(-c2cccc3c4ccc5c(c4n(-c4ccc6c7ccccc7n(-c7ccccc7)c6c4)c23)C2(c3ccccc3-c3ccccc32)c2ccccc2-5)cc1]
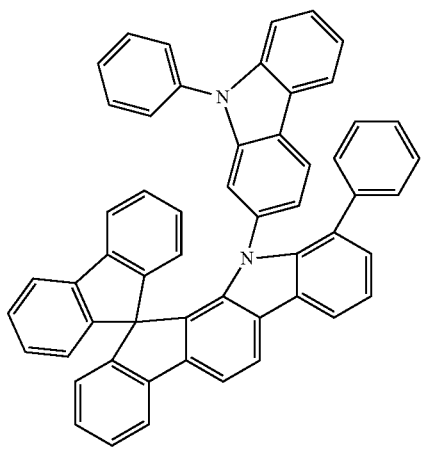 [SMILES: c1ccc(-c2cccc3c4ccc5c(c4n(-c4ccc6c7ccccc7n(-c7ccccc7)c6c4)c23)C2(c3ccccc3-c3ccccc32)c2ccccc2-5)cc1]

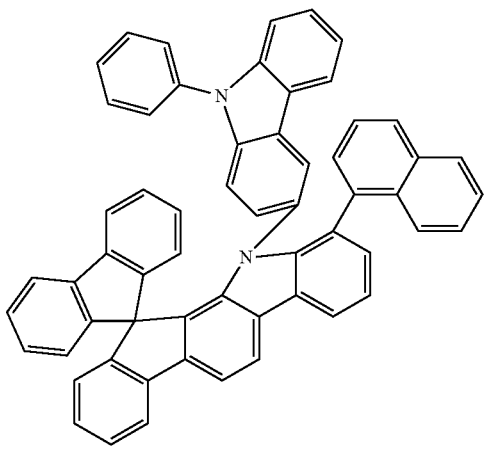 [SMILES: c1ccc(-n2c3ccccc3c3cc(-n4c5c(-c6cccc7ccccc67)cccc5c5ccc6c(c54)C4(c5ccccc5-c5ccccc54)c4ccccc4-6)ccc32)cc1]
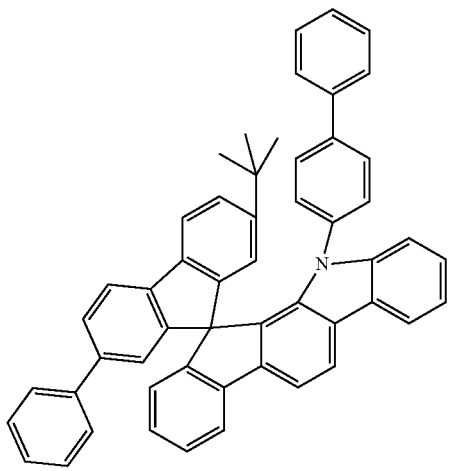 [SMILES: CC(C)(C)c1ccc2c(c1)C1(c3cc(-c4ccccc4)ccc3-2)c2ccccc2-c2ccc3c4ccccc4n(-c4ccc(-c5ccccc5)cc4)c3c21]
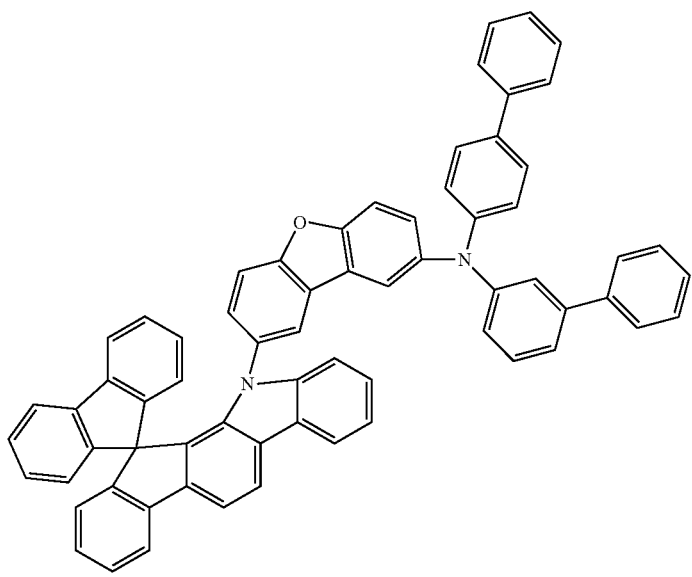 [SMILES: c1ccc(-c2ccc(N(c3cccc(-c4ccccc4)c3)c3ccc4oc5ccc(-n6c7ccccc7c7ccc8c(c76)C6(c7ccccc7-c7ccccc76)c6ccccc6-8)cc5c4c3)cc2)cc1]

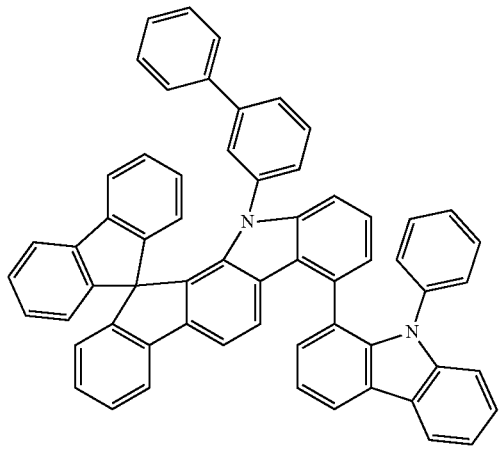 [SMILES: c1ccc(-c2cccc(-n3c4cccc(-c5cccc6c7ccccc7n(-c7ccccc7)c56)c4c4ccc5c(c43)C3(c4ccccc4-c4ccccc43)c3ccccc3-5)c2)cc1]
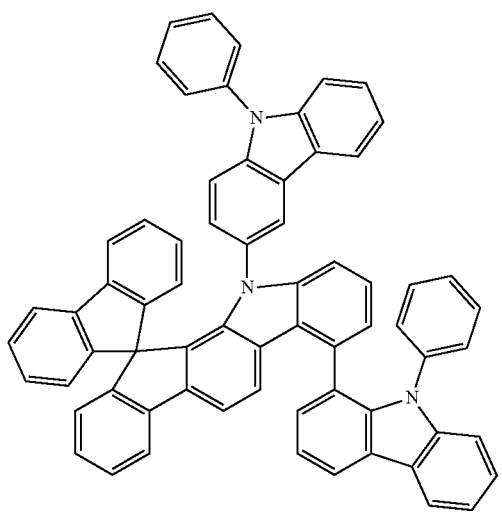 [SMILES: c1ccc(-n2c3ccccc3c3cc(-n4c5cccc(-c6cccc7c8ccccc8n(-c8ccccc8)c67)c5c5ccc6c(c54)C4(c5ccccc5-c5ccccc54)c4ccccc4-6)ccc32)cc1]
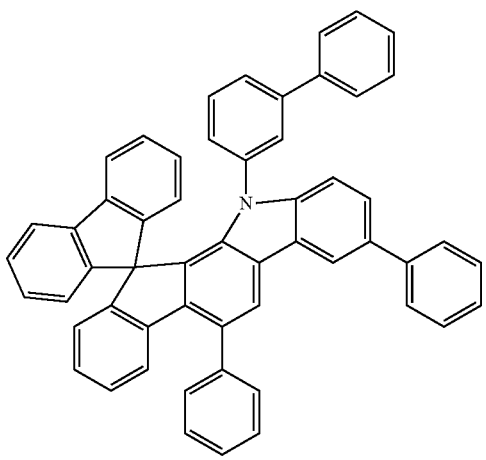 [SMILES: c1ccc(-c2cccc(-n3c4ccc(-c5ccccc5)cc4c4cc(-c5ccccc5)c5c(c43)C3(c4ccccc4-c4ccccc43)c3ccccc3-5)c2)cc1]

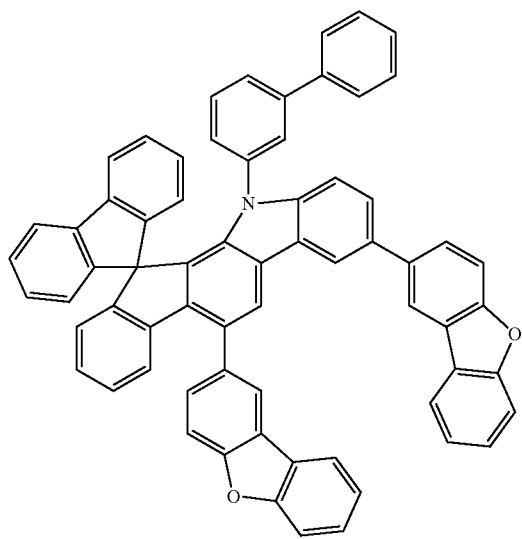 [SMILES: c1ccc(-c2cccc(-n3c4ccc(-c5ccc6oc7ccccc7c6c5)cc4c4cc(-c5ccc6oc7ccccc7c6c5)c5c(c43)C3(c4ccccc4-c4ccccc43)c3ccccc3-5)c2)cc1]
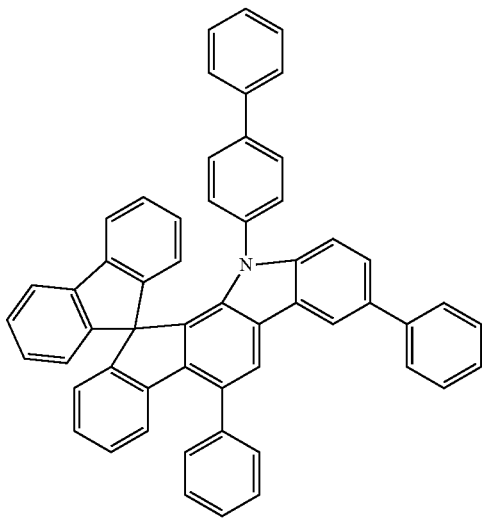 [SMILES: c1ccc(-c2ccc(-n3c4ccc(-c5ccccc5)cc4c4cc(-c5ccccc5)c5c(c43)C3(c4ccccc4-c4ccccc43)c3ccccc3-5)cc2)cc1]
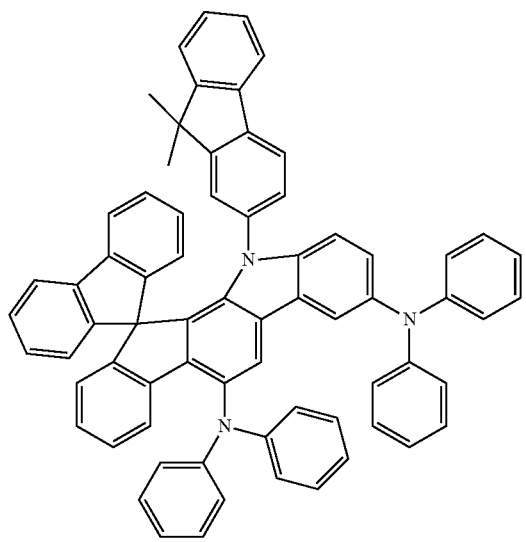 [SMILES: CC1(C)c2ccccc2-c2ccc(-n3c4ccc(N(c5ccccc5)c5ccccc5)cc4c4cc(N(c5ccccc5)c5ccccc5)c5c(c43)C3(c4ccccc4-c4ccccc43)c3ccccc3-5)cc21]

-continued
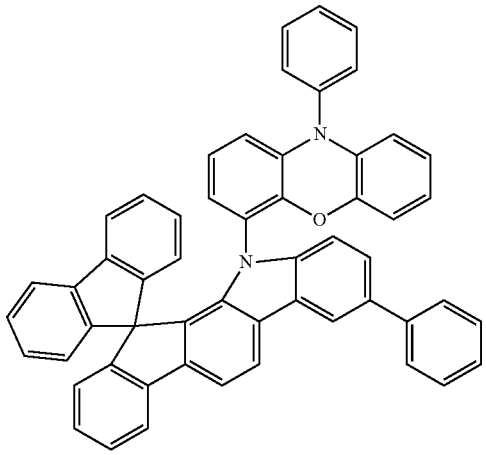 [SMILES: c1ccc(-c2ccc3c(c2)c2ccc4c(c2n3-c2cccc3c2Oc2ccccc2N3c2ccccc2)C2(c3ccccc3-c3ccccc32)c2ccccc2-4)cc1]
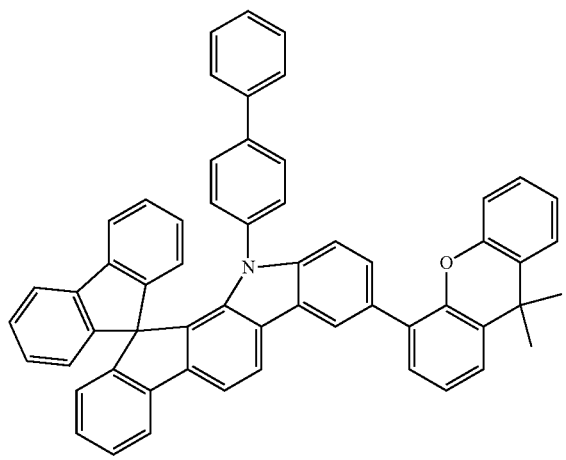 [SMILES: CC1(C)c2ccccc2Oc2c(-c3ccc4c(c3)c3ccc5c(c3n4-c3ccc(-c4ccccc4)cc3)C3(c4ccccc4-c4ccccc43)c3ccccc3-5)cccc21]
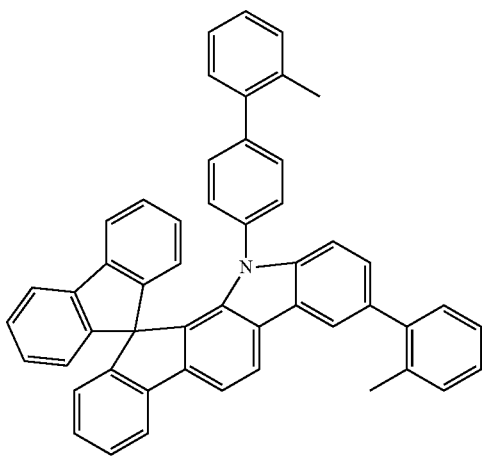 [SMILES: Cc1ccccc1-c1ccc(-n2c3ccc(-c4ccccc4C)cc3c3ccc4c(c32)C2(c3ccccc3-c3ccccc32)c2ccccc2-4)cc1]

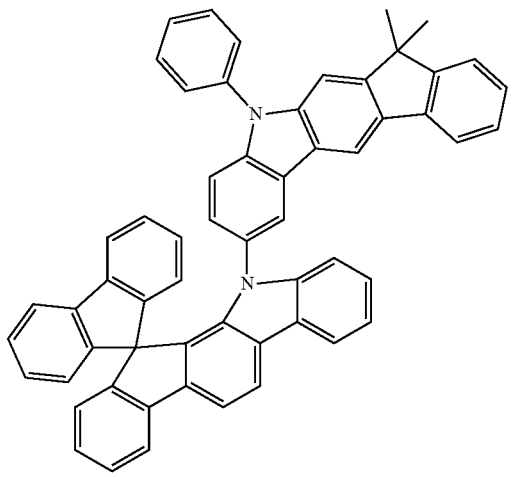 [SMILES: CC1(C)c2ccccc2-c2cc3c4cc(-n5c6ccccc6c6ccc7c(c65)C5(c6ccccc6-c6ccccc65)c5ccccc5-7)ccc4n(-c4ccccc4)c3cc21]
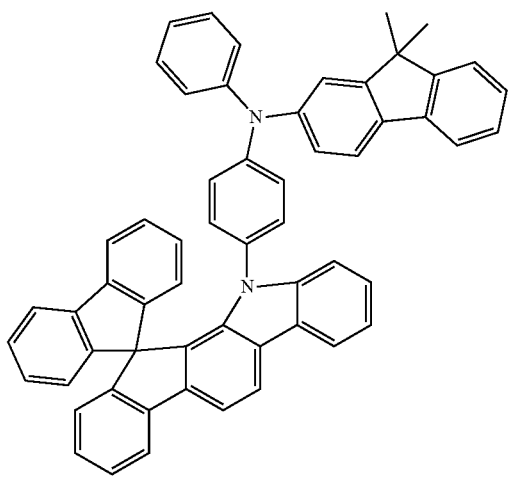 [SMILES: CC1(C)c2ccccc2-c2ccc(N(c3ccccc3)c3ccc(-n4c5ccccc5c5ccc6c(c54)C4(c5ccccc5-c5ccccc54)c4ccccc4-6)cc3)cc21]
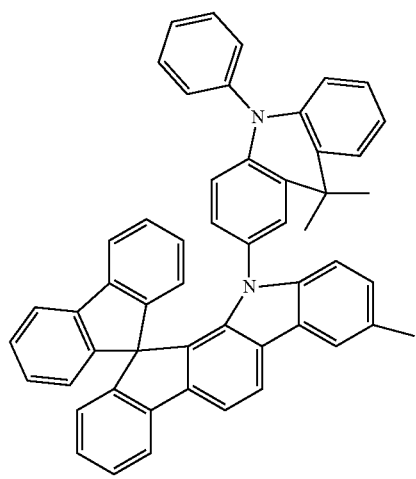 [SMILES: Cc1ccc2c(c1)c1ccc3c(c1n2-c1ccc2c(c1)C(C)(C)c1ccccc1N2c1ccccc1)C1(c2ccccc2-c2ccccc21)c1ccccc1-3]

-continued
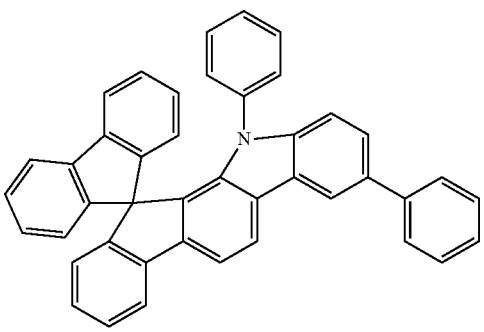 [SMILES: c1ccc(-c2ccc3c(c2)c2ccc4c(c2n3-c2ccccc2)C2(c3ccccc3-c3ccccc32)c2ccccc2-4)cc1]
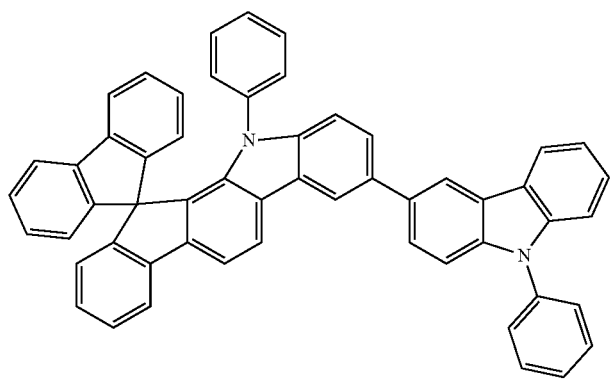 [SMILES: c1ccc(-n2c3ccccc3c3cc(-c4ccc5c(c4)c4ccc6c(c4n5-c4ccccc4)C4(c5ccccc5-c5ccccc54)c4ccccc4-6)ccc32)cc1]
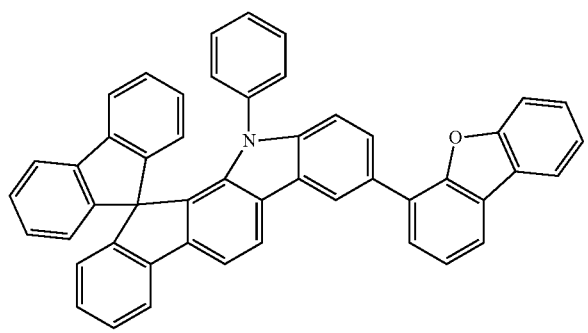 [SMILES: c1ccc(-n2c3ccc(-c4cccc5c4oc4ccccc45)cc3c3ccc4c(c32)C2(c3ccccc3-c3ccccc32)c2ccccc2-4)cc1]
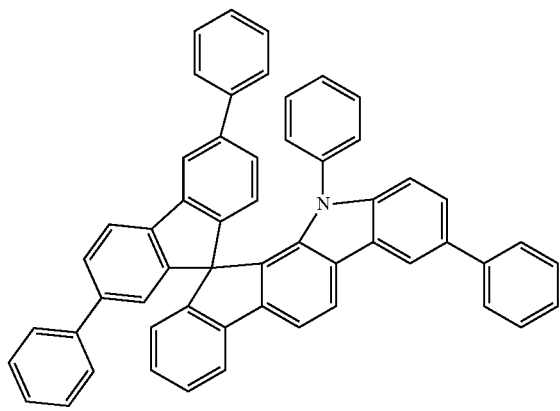 [SMILES: c1ccc(-c2ccc3c(c2)-c2ccc(-c4ccccc4)cc2C32c3ccccc3-c3ccc4c5cc(-c6ccccc6)ccc5n(-c5ccccc5)c4c32)cc1]

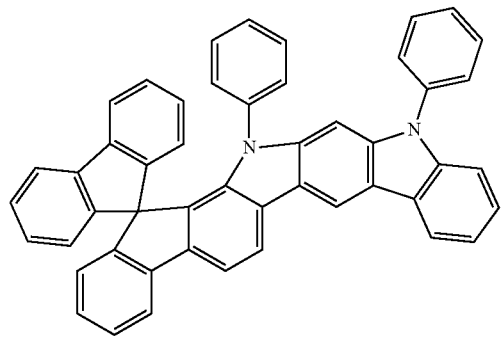 [SMILES: c1ccc(-n2c3ccccc3c3cc4c5ccc6c(c5n(-c5ccccc5)c4cc32)C2(c3ccccc3-c3ccccc32)c2ccccc2-6)cc1]
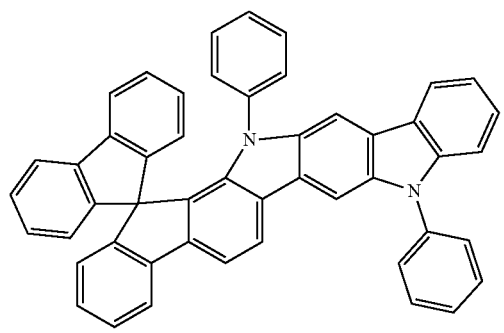 [SMILES: c1ccc(-n2c3ccccc3c3cc4c(cc32)c2ccc3c(c2n4-c2ccccc2)C2(c4ccccc4-c4ccccc42)c2ccccc2-3)cc1]
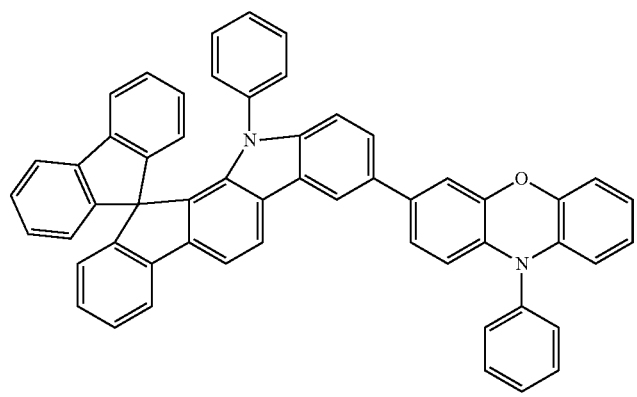 [SMILES: c1ccc(N2c3ccccc3Oc3cc(-c4ccc5c(c4)c4ccc6c(c4n5-c4ccccc4)C4(c5ccccc5-c5ccccc54)c4ccccc4-6)ccc32)cc1]
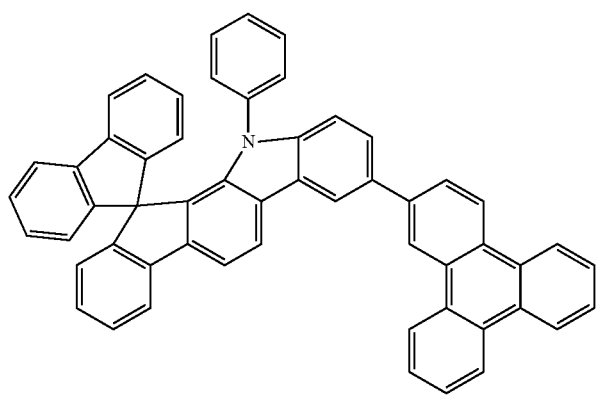 [SMILES: c1ccc(-n2c3ccc(-c4ccc5c6ccccc6c6ccccc6c5c4)cc3c3ccc4c(c32)C2(c3ccccc3-c3ccccc32)c2ccccc2-4)cc1]

-continued
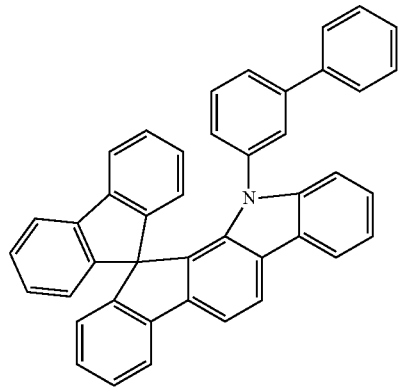 [SMILES: c1ccc(-c2cccc(-n3c4ccccc4c4ccc5c(c43)C3(c4ccccc4-c4ccccc43)c3ccccc3-5)c2)cc1]
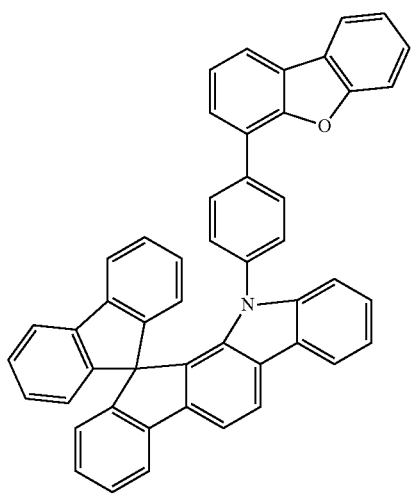 [SMILES: c1ccc2c(c1)-c1ccccc1C21c2ccccc2-c2ccc3c4ccccc4n(-c4ccc(-c5cccc6c5oc5ccccc56)cc4)c3c21]
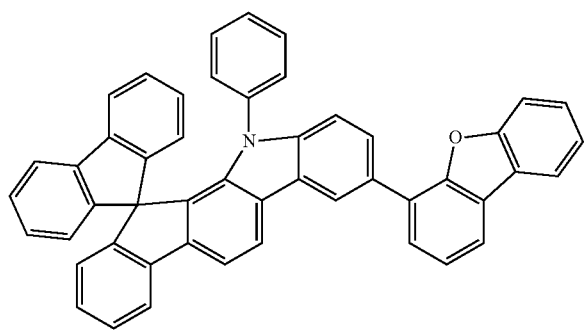 [SMILES: c1ccc(-n2c3ccc(-c4cccc5c4oc4ccccc45)cc3c3ccc4c(c32)C2(c3ccccc3-c3ccccc32)c2ccccc2-4)cc1]

-continued
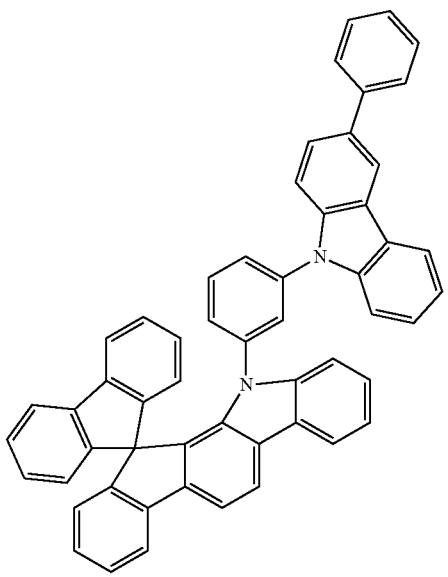 [SMILES: c1ccc(-c2ccc3c(c2)c2ccccc2n3-c2cccc(-n3c4ccccc4c4ccc5c(c43)C3(c4ccccc4-c4ccccc43)c3ccccc3-5)c2)cc1]
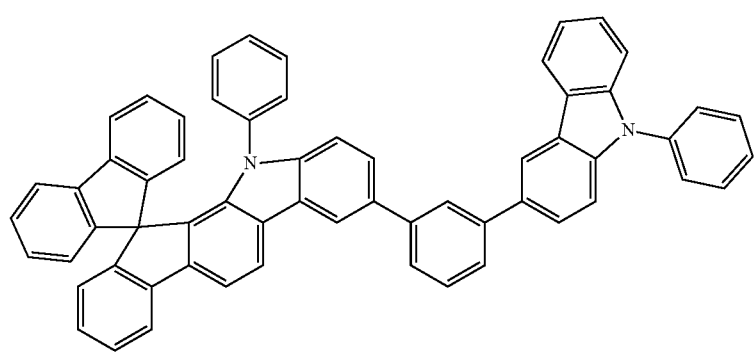 [SMILES: c1ccc(-n2c3ccccc3c3cc(-c4cccc(-c5ccc6c(c5)c5ccc7c(c5n6-c5ccccc5)C5(c6ccccc6-c6ccccc65)c5ccccc5-7)c4)ccc32)cc1]
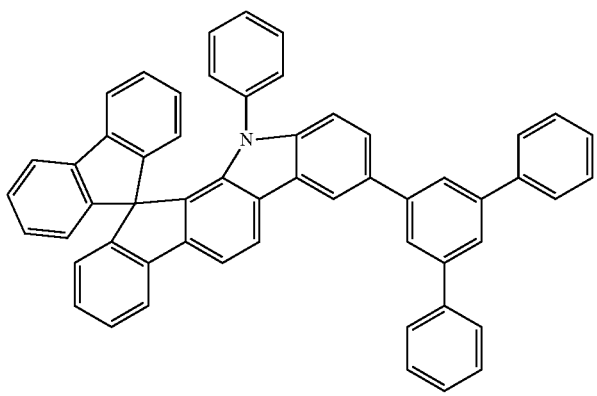 [SMILES: c1ccc(-c2cc(-c3ccccc3)cc(-c3ccc4c(c3)c3ccc5c(c3n4-c3ccccc3)C3(c4ccccc4-c4ccccc43)c3ccccc3-5)c2)cc1]

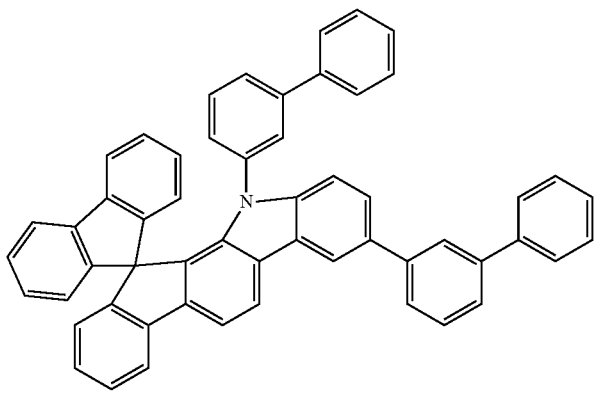 [SMILES: c1ccc(-c2cccc(-c3ccc4c(c3)c3ccc5c(c3n4-c3cccc(-c4ccccc4)c3)C3(c4ccccc4-c4ccccc43)c3ccccc3-5)c2)cc1]
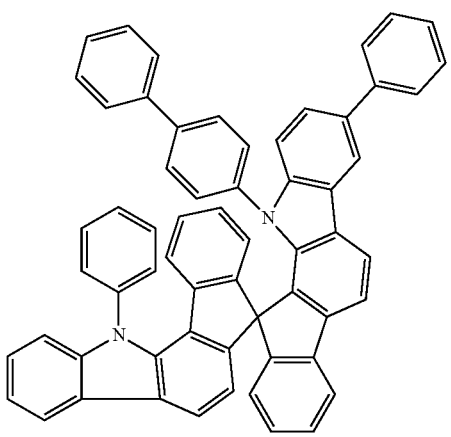 [SMILES: c1ccc(-c2ccc(-n3c4ccc(-c5ccccc5)cc4c4ccc5c(c43)C3(c4ccccc4-5)c4ccccc4-c4c3ccc3c5ccccc5n(-c5ccccc5)c43)cc2)cc1]
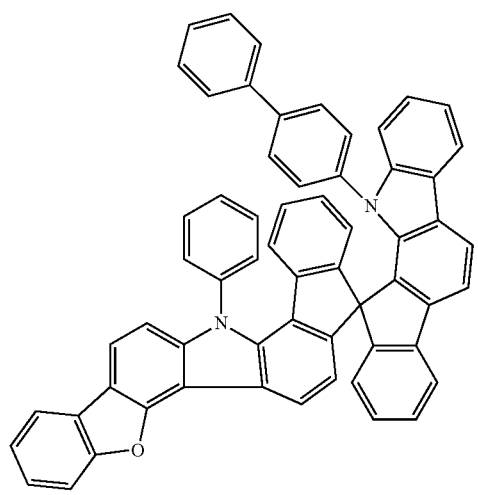 [SMILES: c1ccc(-c2ccc(-n3c4ccccc4c4ccc5c(c43)C3(c4ccccc4-5)c4ccccc4-c4c3ccc3c5c6oc7ccccc7c6ccc5n(-c5ccccc5)c43)cc2)cc1]

-continued
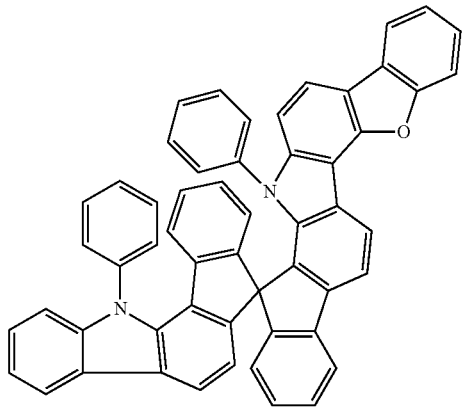 [SMILES: c1ccc(-n2c3ccccc3c3ccc4c(c32)-c2ccccc2C42c3ccccc3-c3ccc4c5c6oc7ccccc7c6ccc5n(-c5ccccc5)c4c32)cc1]
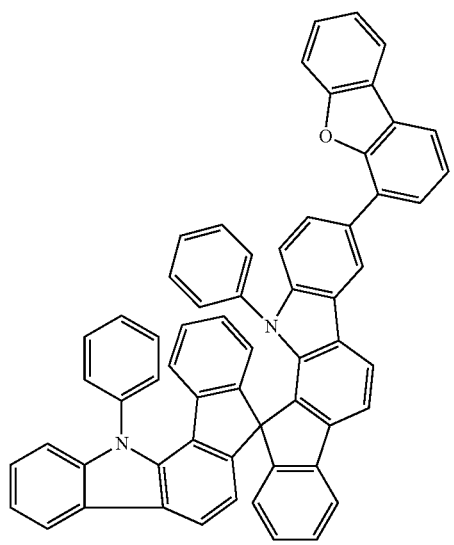 [SMILES: c1ccc(-n2c3ccccc3c3ccc4c(c32)-c2ccccc2C42c3ccccc3-c3ccc4c5cc(-c6cccc7c6oc6ccccc67)ccc5n(-c5ccccc5)c4c32)cc1]
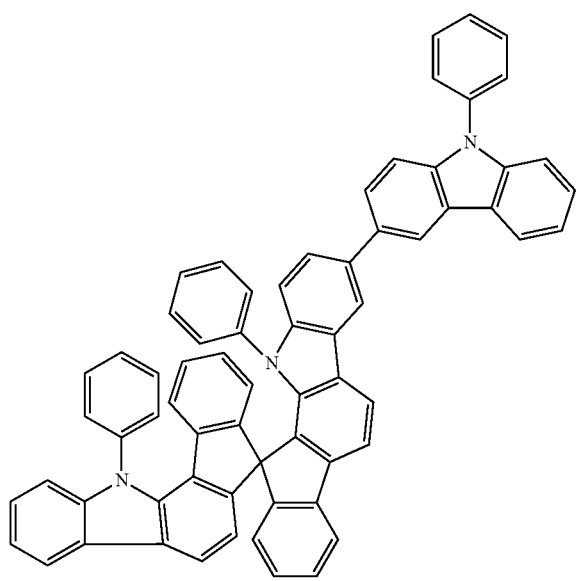 [SMILES: c1ccc(-n2c3ccccc3c3cc(-c4ccc5c(c4)c4ccc6c(c4n5-c4ccccc4)C4(c5ccccc5-6)c5ccccc5-c5c4ccc4c6ccccc6n(-c6ccccc6)c54)ccc32)cc1]

-continued
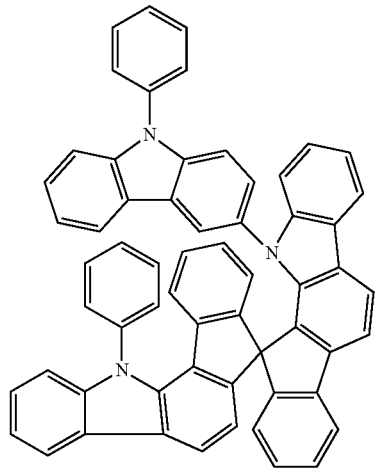 [SMILES: c1ccc(-n2c3ccccc3c3cc(-n4c5ccccc5c5ccc6c(c54)C4(c5ccccc5-6)c5ccccc5-c5c4ccc4c6ccccc6n(-c6ccccc6)c54)ccc32)cc1]
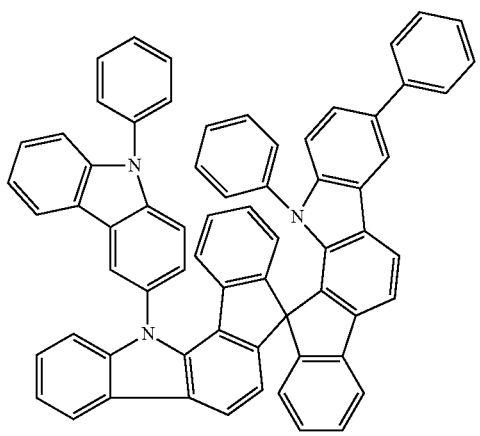 [SMILES: c1ccc(-c2ccc3c(c2)c2ccc4c(c2n3-c2ccccc2)C2(c3ccccc3-4)c3ccccc3-c3c2ccc2c4ccccc4n(-c4ccc5c(c4)c4ccccc4n5-c4ccccc4)c32)cc1]
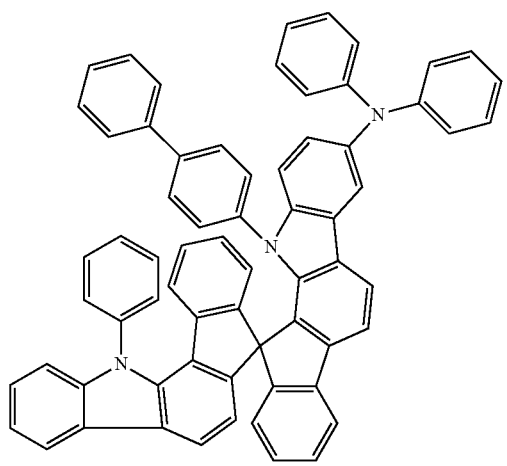 [SMILES: c1ccc(-c2ccc(-n3c4ccc(N(c5ccccc5)c5ccccc5)cc4c4ccc5c(c43)C3(c4ccccc4-5)c4ccccc4-c4c3ccc3c5ccccc5n(-c5ccccc5)c43)cc2)cc1]

-continued
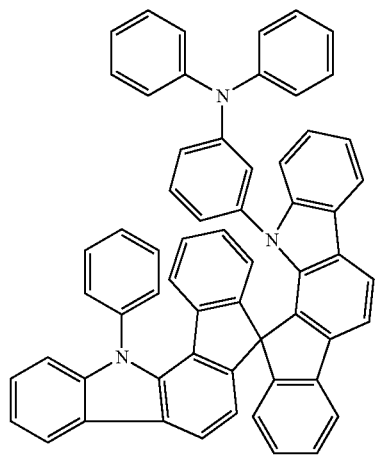 [SMILES: c1ccc(N(c2ccccc2)c2cccc(-n3c4ccccc4c4ccc5c(c43)C3(c4ccccc4-5)c4ccccc4-c4c3ccc3c5ccccc5n(-c5ccccc5)c43)c2)cc1]
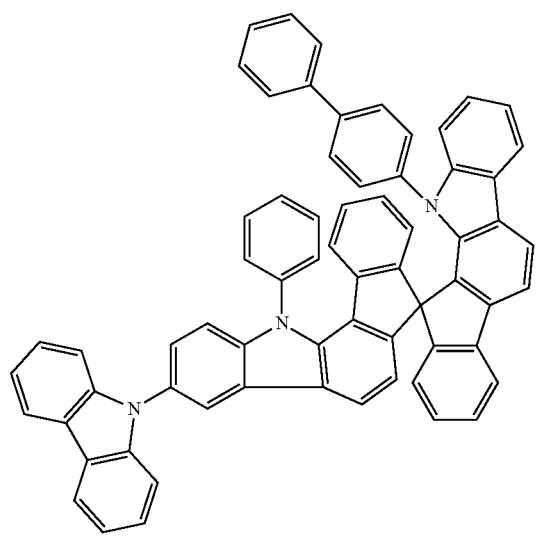 [SMILES: c1ccc(-c2ccc(-n3c4ccccc4c4ccc5c(c43)C3(c4ccccc4-5)c4ccccc4-c4c3ccc3c5cc(-n6c7ccccc7c7ccccc76)ccc5n(-c5ccccc5)c43)cc2)cc1]
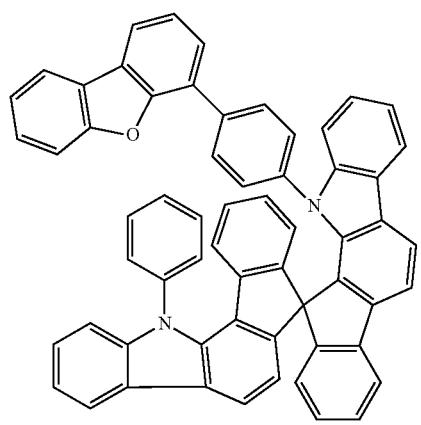 [SMILES: c1ccc(-n2c3ccccc3c3ccc4c(c32)-c2ccccc2C42c3ccccc3-c3ccc4c5ccccc5n(-c5ccc(-c6cccc7c6oc6ccccc67)cc5)c4c32)cc1]

-continued
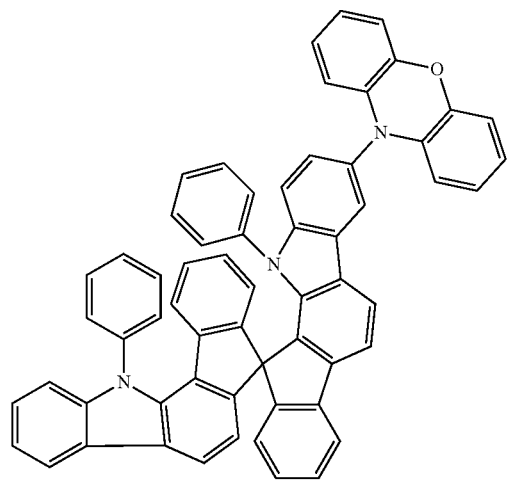 [SMILES: c1ccc(-n2c3ccccc3c3ccc4c(c32)-c2ccccc2C42c3ccccc3-c3ccc4c5cc(N6c7ccccc7Oc7ccccc76)ccc5n(-c5ccccc5)c4c32)cc1]
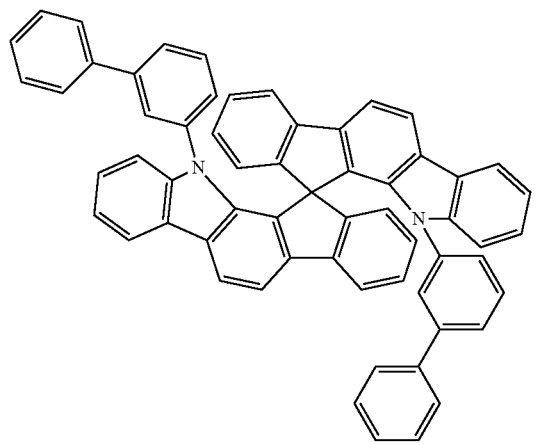 [SMILES: c1ccc(-c2cccc(-n3c4ccccc4c4ccc5c(c43)C3(c4ccccc4-5)c4ccccc4-c4ccc5c6ccccc6n(-c6cccc(-c7ccccc7)c6)c5c43)c2)cc1]
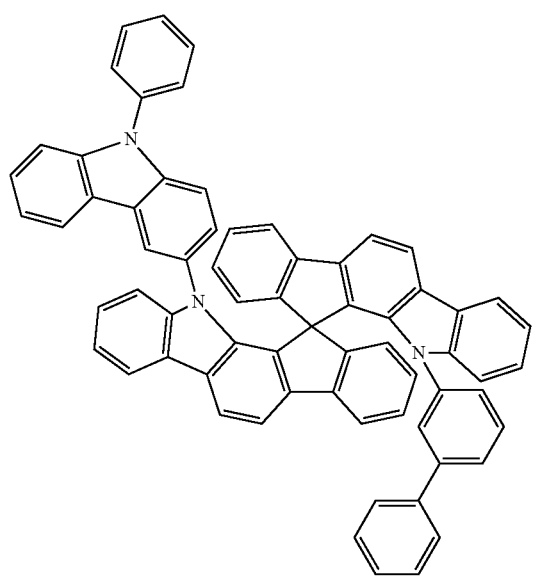 [SMILES: c1ccc(-c2cccc(-n3c4ccccc4c4ccc5c(c43)C3(c4ccccc4-5)c4ccccc4-c4ccc5c6ccccc6n(-c6ccc7c(c6)c6ccccc6n7-c6ccccc6)c5c43)c2)cc1]

-continued
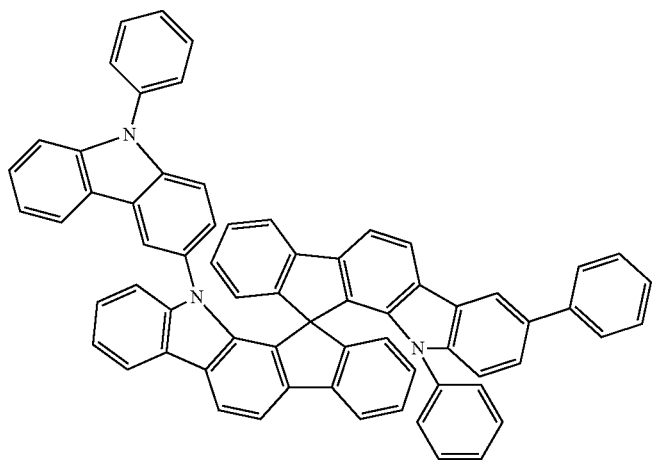 [SMILES: c1ccc(-c2ccc3c(c2)c2ccc4c(c2n3-c2ccccc2)C2(c3ccccc3-c3ccc5c6ccccc6n(-c6ccc7c(c6)c6ccccc6n7-c6ccccc6)c5c32)c2ccccc2-4)cc1]
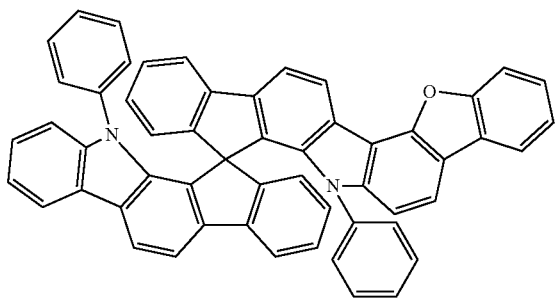 [SMILES: c1ccc(-n2c3ccccc3c3ccc4c(c32)C2(c3ccccc3-4)c3ccccc3-c3ccc4c5c6oc7ccccc7c6ccc5n(-c5ccccc5)c4c32)cc1]
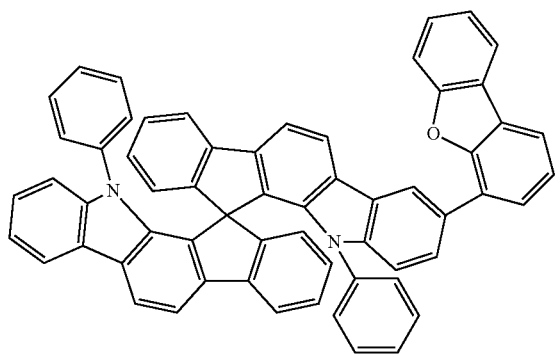 [SMILES: c1ccc(-n2c3ccccc3c3ccc4c(c32)C2(c3ccccc3-4)c3ccccc3-c3ccc4c5cc(-c6cccc7c6oc6ccccc67)ccc5n(-c5ccccc5)c4c32)cc1]
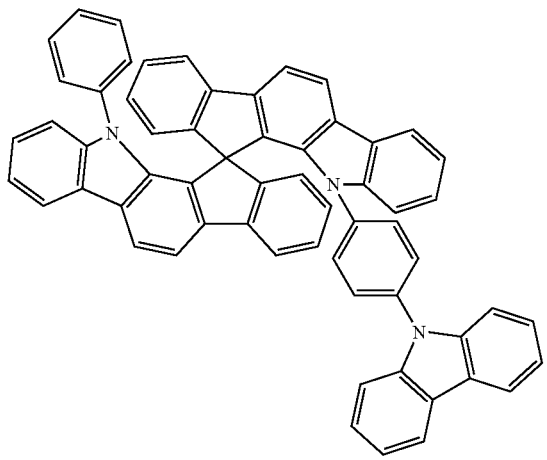 [SMILES: c1ccc(-n2c3ccccc3c3ccc4c(c32)C2(c3ccccc3-4)c3ccccc3-c3ccc4c5ccccc5n(-c5ccc(-n6c7ccccc7c7ccccc76)cc5)c4c32)cc1]

-continued
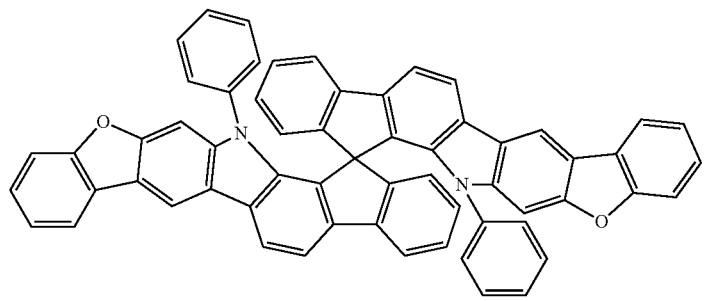 [SMILES: c1ccc(-n2c3cc4oc5ccccc5c4cc3c3ccc4c(c32)C2(c3ccccc3-4)c3ccccc3-c3ccc4c5cc6c(cc5n(-c5ccccc5)c4c32)oc2ccccc26)cc1]
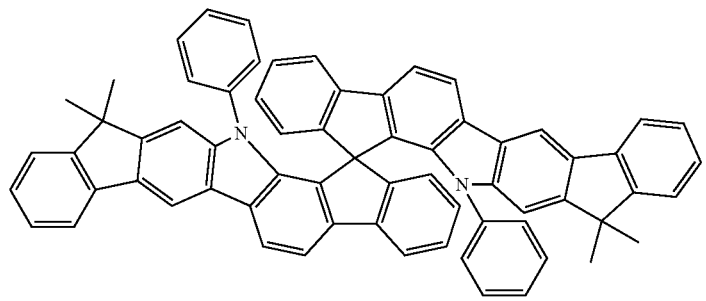 [SMILES: CC1(C)c2ccccc2-c2cc3c4ccc5c(c4n(-c4ccccc4)c3cc21)C1(c2ccccc2-5)c2ccccc2-c2ccc3c4cc5c(cc4n(-c4ccccc4)c3c21)C(C)(C)c1ccccc1-5]
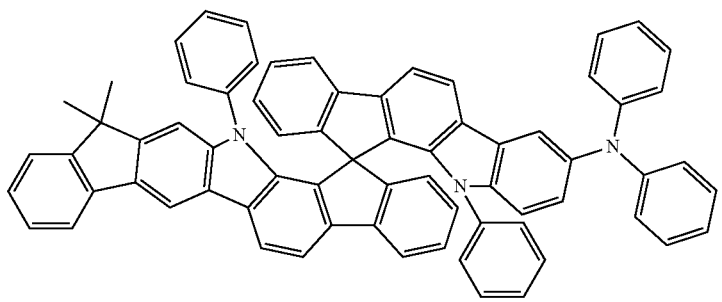 [SMILES: CC1(C)c2ccccc2-c2cc3c4ccc5c(c4n(-c4ccccc4)c3cc21)C1(c2ccccc2-c2ccc3c4cc(N(c6ccccc6)c6ccccc6)ccc4n(-c4ccccc4)c3c21)c1ccccc1-5]
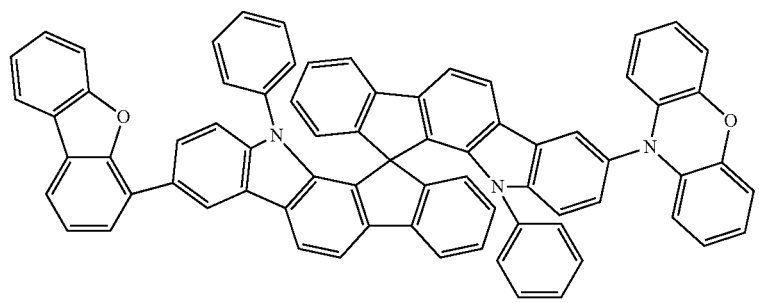 [SMILES: c1ccc(-n2c3ccc(-c4cccc5c4oc4ccccc45)cc3c3ccc4c(c32)C2(c3ccccc3-4)c3ccccc3-c3ccc4c5cc(N6c7ccccc7Oc7ccccc76)ccc5n(-c5ccccc5)c4c32)cc1]
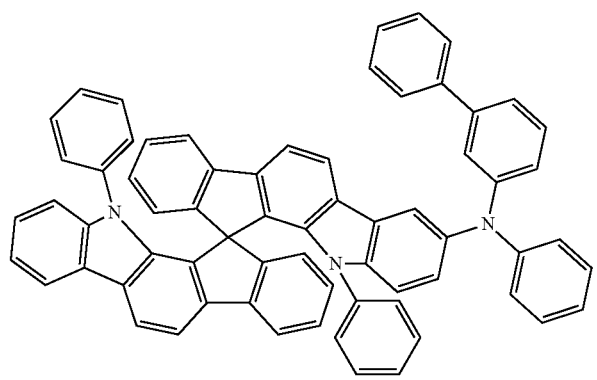 [SMILES: c1ccc(-c2cccc(N(c3ccccc3)c3ccc4c(c3)c3ccc5c(c3n4-c3ccccc3)C3(c4ccccc4-c4ccc6c7ccccc7n(-c7ccccc7)c6c43)c3ccccc3-5)c2)cc1]

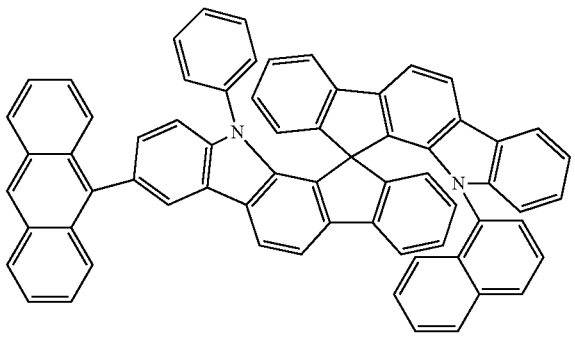 [SMILES: c1ccc(-n2c3ccc(-c4c5ccccc5cc5ccccc45)cc3c3ccc4c(c32)C2(c3ccccc3-4)c3ccccc3-c3ccc4c5ccccc5n(-c5cccc6ccccc56)c4c32)cc1]

The inventive compounds of the formula (1) can be prepared by the route outlined in scheme 1.

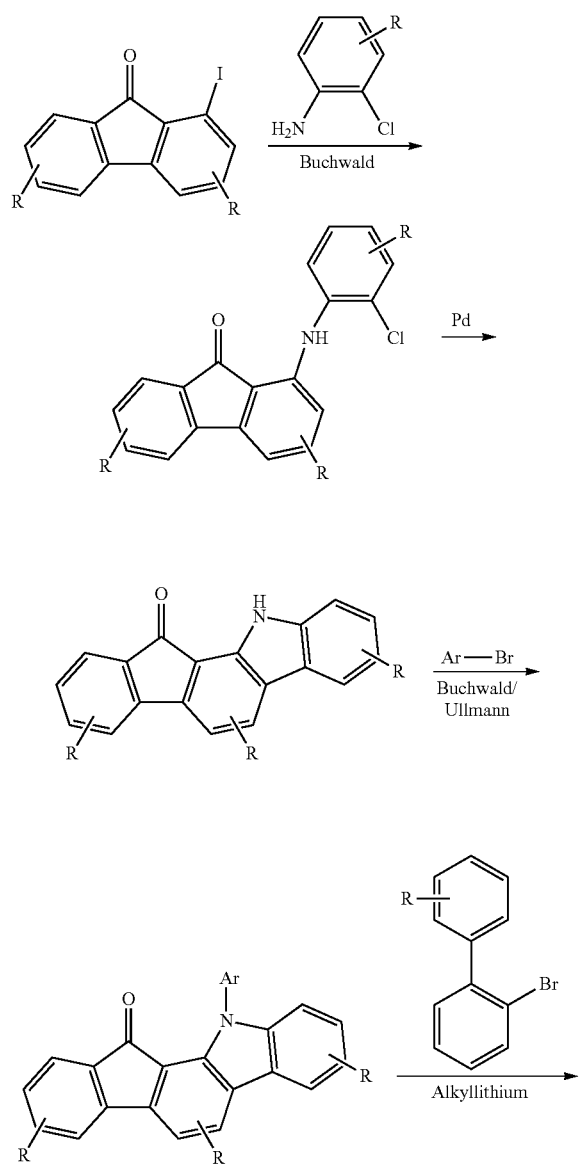

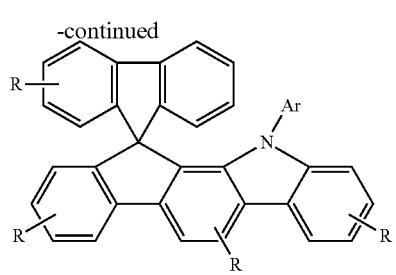

This synthesis can be conducted proceeding from an optionally substituted 1-halofluorenone, where the halogen is preferably Br or I. This is reacted with an optionally substituted ortho-haloaminobenzene in a C—N coupling reaction, for example under Pd or Cu catalysis, where the halogen is preferably Cl, Br or I. In an entirely analogous manner, it is possible, for example, to use a fluorene, dibenzofuran, dibenzothiophene or naphthalene derivative, which leads to compounds containing groups of the formula (4) or (5). The ring closure to give the corresponding carbazole derivative is effected by an intramolecular Pd-catalyzed coupling reaction.

This carbazole derivative may be substituted on the nitrogen by the Ar group via a Buchwald or Ullmann coupling reaction. In the last step, the ring closure reaction to give the spirobifluorene derivative is then effected by reaction with a lithiated biphenyl derivative, followed by acidic cyclization.

The synthesis of compounds of the formula (3) is shown in scheme 2 and can be effected proceeding from indolo-fluorenone, which can be synthesized according to scheme 1. In this case, the spiro compound is formed using a 2,2'-dibromobiphenyl derivative, and so the spiro compound obtained has a bromine atom in the 4' position. Proceeding from this, analogously to scheme 1, it is possible to synthesize the fused-on indolo group.

Scheme 2

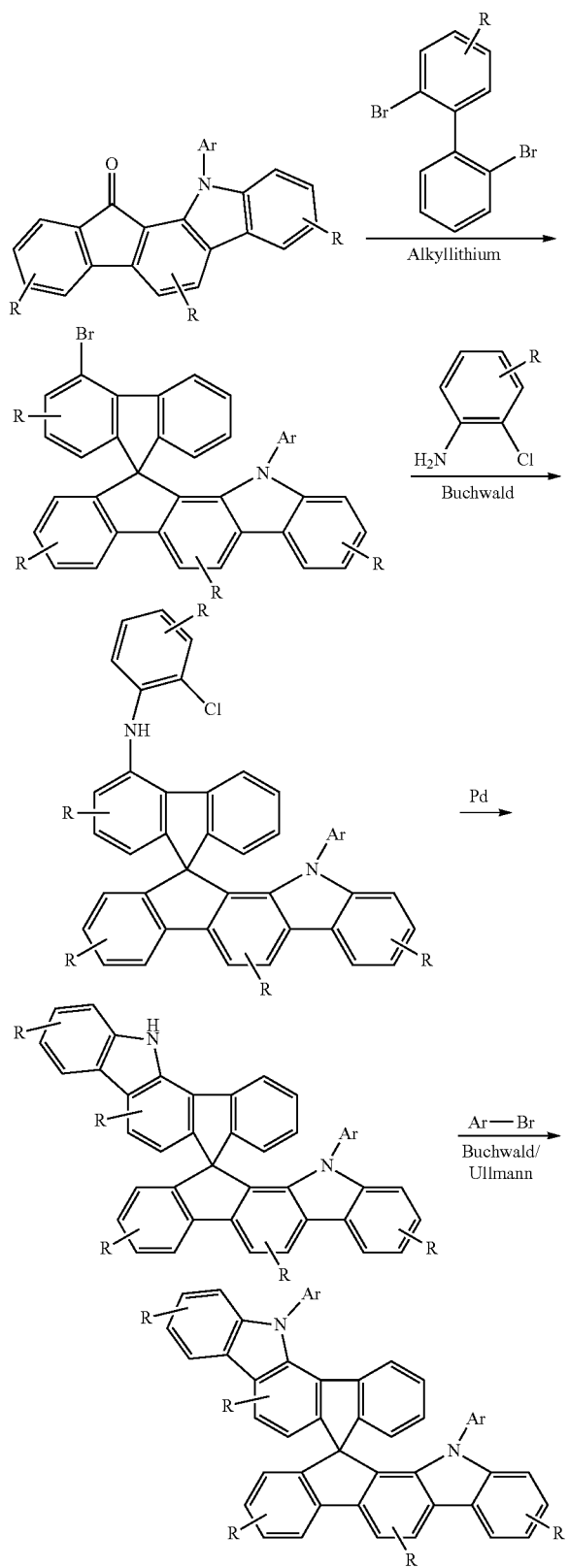

The synthesis of compounds of the formula (2) can be effected analogously.

The above-described compounds of the invention, especially compounds substituted by reactive leaving groups, such as bromine, iodine, chlorine, boronic acid or boronic ester, or by reactive polymerizable groups such as olefins, styrenes, acrylates or oxetanes, may find use as monomers for production of corresponding oligomers, dendrimers or polymers. The oligomerization or polymerization is preferably effected via the halogen functionality or the boronic acid functionality or via the polymerizable group. It is additionally possible to crosslink the polymers via groups of this kind. The compounds of the invention and polymers may be used in the form of a crosslinked or uncrosslinked layer.

The invention therefore further provides oligomers, polymers or dendrimers containing one or more of the above-detailed compounds of the invention, wherein one or more bonds of the compound of the invention to the polymer, oligomer or dendrimer are present in place of substituents at one or more positions. According to the linkage of the compound of the invention, it forms a side chain of the oligomer or polymer or is incorporated in the main chain or forms the core of a dendrimer. The polymers, oligomers or dendrimers may be conjugated, partly conjugated or non-conjugated. The oligomers or polymers may be linear, branched or dendritic. For the repeat units of the compounds of the invention in oligomers, dendrimers and polymers, the same preferences apply as described above.

For preparation of the oligomers or polymers, the monomers of the invention are homopolymerized or copolymerized with further monomers. Preference is given to homopolymers or copolymers wherein the units of formula (1) or (2) or (3) or the above-recited preferred embodiments are present to an extent of 0.01 to 99.9 mol %, preferably 5 to 90 mol %, more preferably 20 to 80 mol %. Suitable and preferred comonomers which form the polymer base skeleton are chosen from fluorenes (for example according to EP 842208 or WO 2000/22026), spirobifluorenes (for example according to EP 707020, EP 894107 or WO 2006/061181), para-phenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units. In addition, the polymers may contain triplet emitters either in copolymerized form or mixed in as a blend. Specifically the combination of the oligomers, polymers or dendrimers of the invention with triplet emitters leads to particularly good results.

For the processing of the compounds of the invention from the liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention therefore further provides a formulation comprising a compound of the invention and at least one further compound. The further compound may, for example, be a solvent, especially one of the abovementioned solvents or a mixture of these solvents. The further compound may alternatively be at least one further organic or inorganic compound which is likewise used in the electronic device, for example an emitting compound and/or a further matrix material. Suitable emitting compounds and further matrix materials are listed at the back in connection with the organic electroluminescent device. This further compound may also be polymeric.

The compounds of the invention are suitable for use in an electronic device, especially in an organic electroluminescent device.

The present invention therefore further provides for the use of a compound of the invention in an electronic device, especially in an organic electroluminescent device.

The present invention still further provides an electronic device comprising at least one compound of the invention.

An electronic device in the context of the present invention is a device comprising at least one layer comprising at least one organic compound. This component may also comprise inorganic materials or else layers formed entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), dye-sensitized organic solar cells (DSSCs), organic optical detectors, organic photoreceptors, organic field-quench devices (O-FQDs), light-emitting electrochemical cells (LECs), organic laser diodes (O-lasers) and organic plasmon emitting devices, but preferably organic electroluminescent devices (OLEDs), more preferably phosphorescent OLEDs.

The organic electroluminescent device comprises cathode, anode and at least one emitting layer. Apart from these layers, it may comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are systems having three emitting layers, where the three layers show blue, green and orange or red emission (for the basic construction see, for example, WO 2005/011013). The organic electroluminescent device of the invention may also be a tandem OLED, especially also for white-emitting OLEDs.

The compound of the invention according to the above-detailed embodiments may be used in different layers, according to the exact structure. Preference is given to an organic electroluminescent device containing a compound of formula (1) or formula (2) or formula (3) or the preferred embodiments set out above as matrix material for phosphorescent or fluorescent emitters, especially for phosphorescent emitters, and/or in an electron-blocking or exciton-blocking layer and/or in a hole transport layer and/or in a hole blocker layer and/or in a hole blocker or electron transport layer, according to the exact substitution.

In a preferred embodiment of the invention, the compound of the invention is used as matrix material for a phosphorescent compound in an emitting layer. In this case, the organic electroluminescent device may contain an emitting layer, or it may contain a plurality of emitting layers, where at least one emitting layer contains at least one compound of the invention as matrix material.

When the compound of the invention is used as matrix material for a phosphorescent compound in an emitting layer, it is preferably used in combination with one or more phosphorescent materials (triplet emitters).

Phosphorescence in the context of this invention is understood to mean luminescence from an excited state having higher spin multiplicity, i.e. a spin state >1, especially from an excited triplet state. In the context of this application, all luminescent complexes with transition metals or lanthanides, especially all iridium, platinum and copper complexes, shall be regarded as phosphorescent compounds.

The mixture of the compound of the invention and the emitting compound contains between 99% and 1% by volume, preferably between 98% and 10% by volume, more preferably between 97% and 60% by volume and especially between 95% and 80% by volume of the compound of the invention, based on the overall mixture of emitter and matrix material. Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material.

A further preferred embodiment of the present invention is the use of the compound of the invention as matrix material for a phosphorescent emitter in combination with a further matrix material. Particularly suitable matrix materials which can be used in combination with the inventive compounds are aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527, WO 2008/086851 or WO 2013/041176, indolocarbazole derivatives, for example according to WO 2007/063754 or WO 2008/056746, indenocarbazole derivatives, for example according to WO 2010/136109, WO 2011/000455, WO 2013/041176 or WO 2013/056776, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2007/063754, WO 2008/056746, WO 2010/015306, WO 2011/057706, WO 2011/060859 or WO 2011/060877, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to WO 2011/042107, WO 2011/060867, WO 2011/088877 and WO 2012/143080, or triphenylene derivatives, for example according to WO 2012/048781. It is likewise possible for a further phosphorescent emitter having shorter-wavelength emission than the actual emitter to be present as co-host in the mixture, or a compound not involved in charge transport to a significant extent, if at all, as described, for example, in WO 2010/108579.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum.

Examples of the above-described emitters can be found in applications WO 00/70655, WO 2001/41512, WO 2002/02714, WO 2002/15645, EP 1191613, EP 1191612, EP 1191614, WO 2005/033244, WO 2005/019373, US 2005/0258742, WO 2010/086089, WO 2011/157339, WO 2012/007086, WO 2012/163471, WO 2013/000531 and WO 2013/020631, WO 2014/008982 and WO 2014/023377. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

The compounds of the invention are especially also suitable as matrix materials for phosphorescent emitters in organic electroluminescent devices, as described, for example, in US 2011/0248247 and US 2012/0223633. In these multicolor display components, an additional blue emission layer is applied by vapor deposition over the full area to all pixels, including those having a color other than blue. It has been found that, surprisingly, the compounds of the invention, when they are used as matrix materials for the red and/or green pixels, still lead to very good emission together with the blue emission layer applied by vapor deposition.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In a further embodiment of the invention, the compound of the invention is used in a hole transport layer or in an electron blocker layer or exciton blocker layer.

In yet a further preferred embodiment of the invention, the compound of the invention is used as electron transport material in an electron transport or electron injection layer. In this case, the emitting layer may be fluorescent or phosphorescent. When the compound is used as electron transport material, it may be preferable for it to be doped, for example with alkali metal complexes, for example LiQ (lithium hydroxyquinolinate).

In yet a further preferred embodiment of the invention, the compound of the invention is used in a hole blocker layer. A hole blocker layer is understood to be a layer which directly adjoins an emitting layer on the cathode side.

In the further layers of the organic electroluminescent device of the invention, it is possible to use any materials as typically used according to the prior art. The person skilled in the art will therefore be able, without exercising inventive skill, to use any materials known for organic electroluminescent devices in combination with the inventive compounds of formula (1) or formula (2) or formula (3) or the above-recited preferred embodiments.

Additionally preferred is an organic electroluminescent device, characterized in that one or more layers are coated by a sublimation process. In this case, the materials are applied by vapor deposition in vacuum sublimation systems at an initial pressure of less than $10^{-5}$ mbar, preferably less than $10^{-6}$ mbar. It is also possible that the initial pressure is even lower, for example less than $10^{-7}$ mbar.

Preference is likewise given to an organic electroluminescent device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured (for example, M. S. Arnold et al., *Appl. Phys. Lett.* 2008, 92, 053301).

Preference is additionally given to an organic electroluminescent device, characterized in that one or more layers are produced from solution, for example by spin-coating, or by any printing method, for example screen printing, flexographic printing, offset printing, LITI (light-induced thermal imaging, thermal transfer printing), inkjet printing or nozzle printing. For this purpose, soluble compounds are needed, which are obtained, for example, through suitable substitution.

In addition, hybrid methods are possible, in which, for example, one or more layers are applied from solution and one or more further layers are applied by vapor deposition.

These methods are known in general terms to those skilled in the art and can be applied by those skilled in the art without exercising inventive skill to organic electroluminescent devices comprising the compounds of the invention.

The compounds of the invention and the organic electroluminescent devices of the invention are notable for one or more of the following surprising advantages over the prior art:

1. The compounds of the invention, used as matrix material for fluorescent or phosphorescent emitters, lead to long lifetimes. This is especially true when the compounds are used as matrix material for a phosphorescent emitter.
2. The compounds of the invention lead to very low operating voltages. This is especially true when the compounds are used as matrix material for a phosphorescent emitter.

These abovementioned advantages are not accompanied by a deterioration in the further electronic properties.

The invention is illustrated in detail by the examples which follow, without any intention of restricting it thereby. The person skilled in the art will be able to use the information given to execute the invention over the entire scope disclosed and to prepare further compounds of the invention without exercising inventive skill and to use them in electronic devices or to employ the process of the invention.

EXAMPLES

The syntheses which follow, unless stated otherwise, are conducted under a protective gas atmosphere in dried solvents. The solvents and reagents can be purchased from ALDRICH or ABCR. The numbers given for the reactants that are not commercially available are the corresponding CAS numbers.

Synthesis Examples

Example 1a: 1-(2-Chlorophenylamino)fluoren-9-one

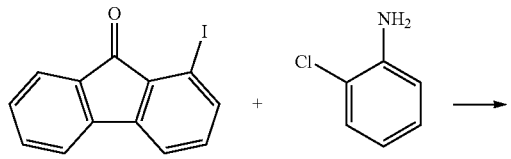

-continued

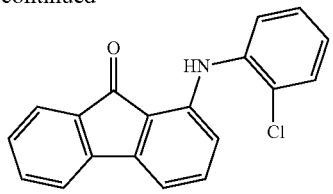

In a 1 L four-neck flask, 52 g (166 mmol) of 1-iodofluoren-9-one (CAS 52086-21-2), 19.0 mL (171 mmol) of 2-chloroaniline (CAS 95-51-2), 59.8 g (432 mmol) of potassium carbonate, 3.85 g (6.6 mmol) of XantPhos and 746 mg (3.3 mmol) of palladium diacetate were dissolved in 390 mL of toluene and heated under reflux for 13 h until conversion was complete. After cooling to room temperature, the organic phase is extended with 200 mL of toluene and hydrolyzed with 500 mL of water. The organic phase is washed once with 300 mL of water and twice with 200 mL each time of 3M HCl solution. The organic phase is filtered through $Al_2O_3$. After the removal of the solvents under reduced pressure, the product is obtained as an orange solid. The yield is 48.0 g (157 mmol, corresponding to 95%).

In an analogous manner, it is possible to prepare the following compounds:

| | Reactant 1 | Reactant 2 | Product | Yield |
|---|---|---|---|---|
| 1b | (structure: 1-iodofluoren-9-one) | (structure: 3-chloro-biphenyl-4-amine, 7285-66-7) | (structure: product) | 83% |

-continued
| | Reactant 1 | Reactant 2 | Product | Yield |
|---|---|---|---|---|
| 1c | 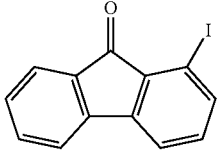 [SMILES: O=C1c2ccccc2-c2cccc(I)c21] | 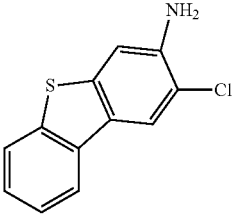 [SMILES: Nc1cc2sc3ccccc3c2cc1Cl]  858426-71-8 | 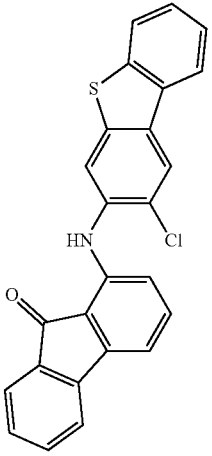 [SMILES: O=C1c2ccccc2-c2cccc(Nc3cc4sc5ccccc5c4cc3Cl)c21] | 78% |
| 1d | 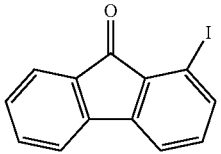 [SMILES: O=C1c2ccccc2-c2cccc(I)c21] | 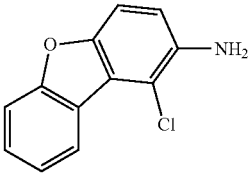 [SMILES: Nc1ccc2oc3ccccc3c2c1Cl]  133617-97-7 | 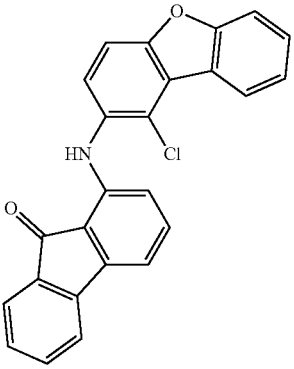 [SMILES: O=C1c2ccccc2-c2cccc(Nc3ccc4oc5ccccc5c4c3Cl)c21] | 67% |
| 1e | 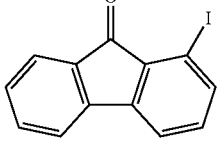 | 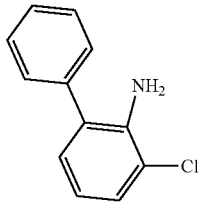 [SMILES: Nc1c(Cl)cccc1-c1ccccc1]  76838-82-9 | 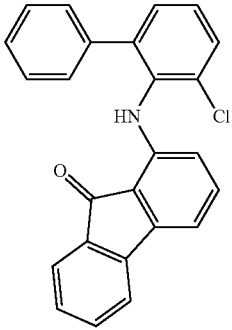 [SMILES: O=C1c2ccccc2-c2cccc(Nc3c(Cl)cccc3-c3ccccc3)c21] | 53% |
| 1f | 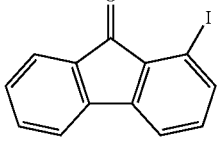 | 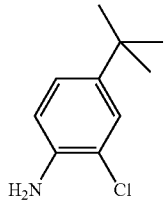  42265-67-8 | 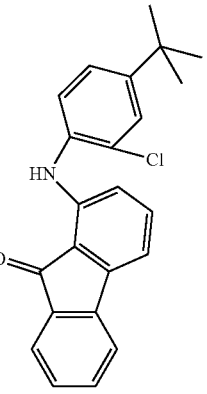 | 73% |

-continued
| Reactant 1 | Reactant 2 | Product | Yield |
|---|---|---|---|
| 1g 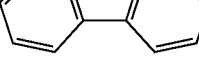 | 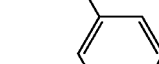 57013-94-2 | 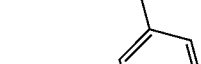 | 68% |
| 1h 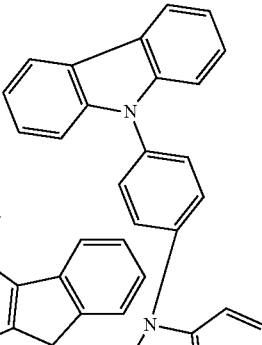 from Ex. 7q | 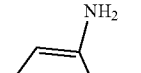 95/−51 | 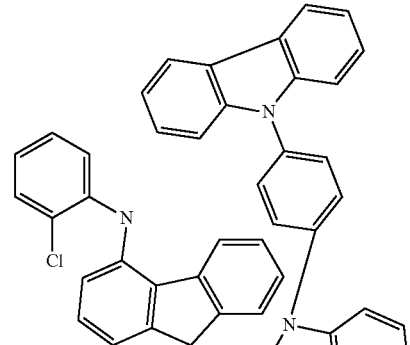 | 70% |
| 1i 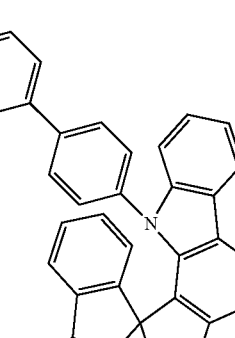 from Ex. 7p | 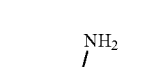 95-51-2 | 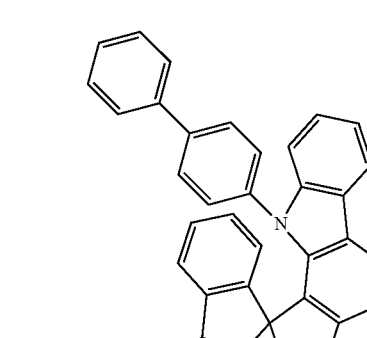 | 72% |

Example 2a:
11H-11-Azaindeno[2,1-a]fluoren-12-one

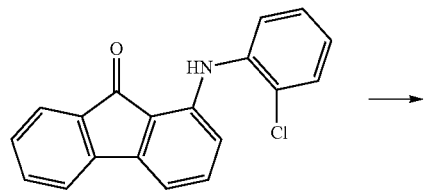

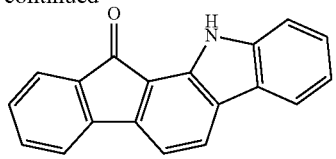

A 500 mL four-neck flask is initially charged with 24 g (78 mmol) of 1a, 28.2 g (204 mmol) of potassium carbonate, 35 mg (1.5 mmol) of palladium diacetate, 1.2 g (3.0 mmol) of tricyclohexylphosphine tetrafluoroborate in 250 mL of DMAc, and the mixture is stirred at 145° C. for three days. On completion of conversion, the mixture is cooled down to room temperature and hydrolyzed with 200 mL of water. The precipitated solid is filtered and washed with water (2×300 mL). After extraction by stirring twice with ethanol at 60° C., the product is obtained as an ochre solid. The yield is 18.3 g (68 mmol, corresponding to 87% of theory).

In an analogous manner, it is possible to prepare the following compounds:

| | Reactant | Product | Yield |
|---|---|---|---|
| 2b | | | 72% |

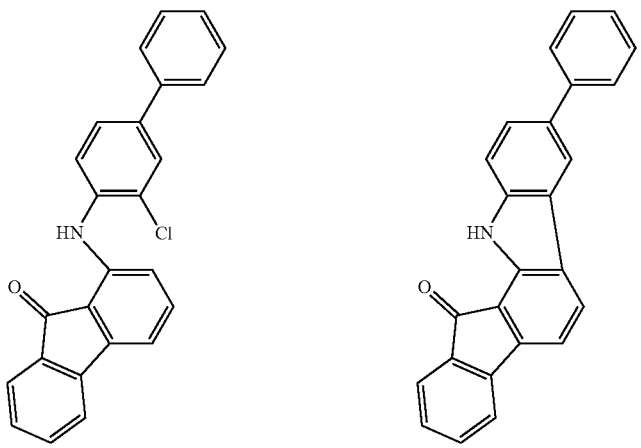

| | Reactant | Product | Yield |
|---|---|---|---|
| 2c | | | 73% |

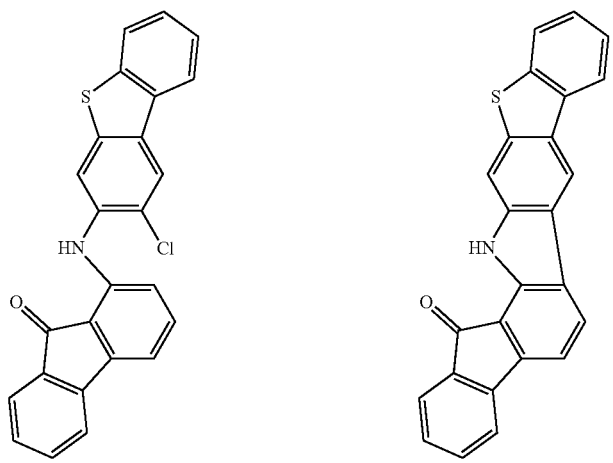

-continued
| | Reactant | Product | Yield |
|---|---|---|---|
| 2d | 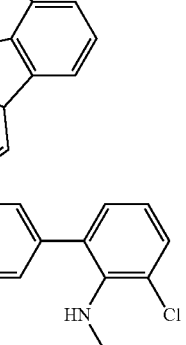 | 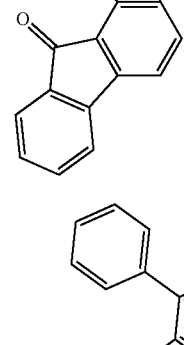 | 67% |
| 2e | 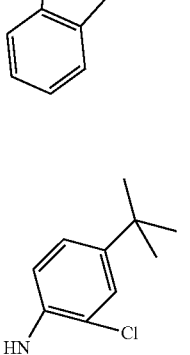 | 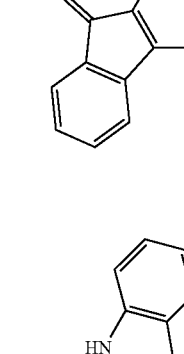 | 56% |
| 2f | 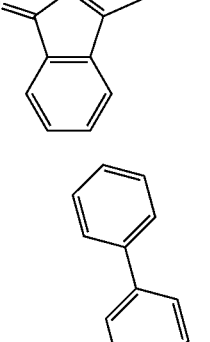 | 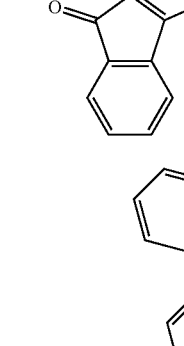 | 71% |
| 2g | 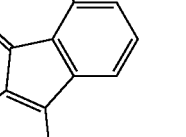 | 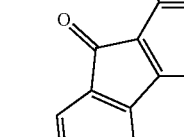 | 67% |

| Reactant | Product | Yield |
|---|---|---|
| 2h 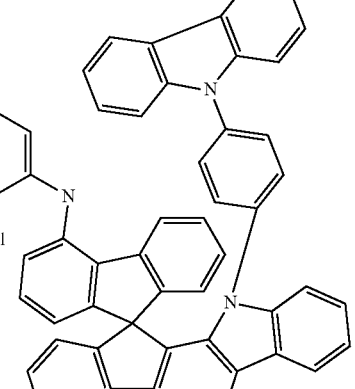 | 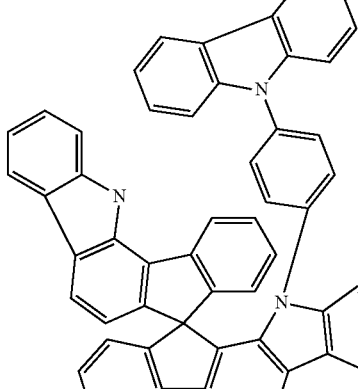 | 65% |
| 2i 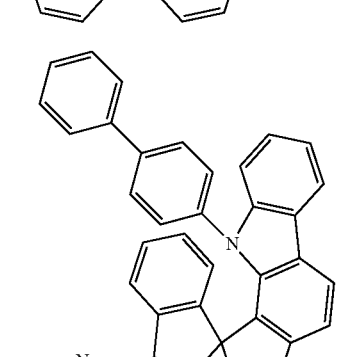 | 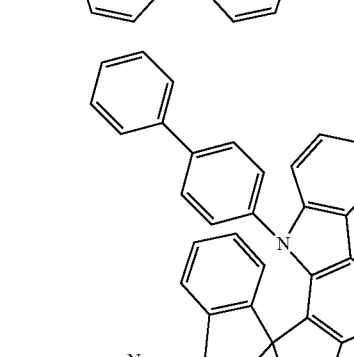 | 68% |

Example 3a: 11-Biphenyl-4-yl-11H-11-azaindeno[2,1-a]fluoren-12-one

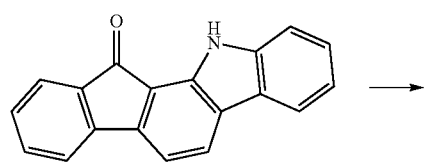

→

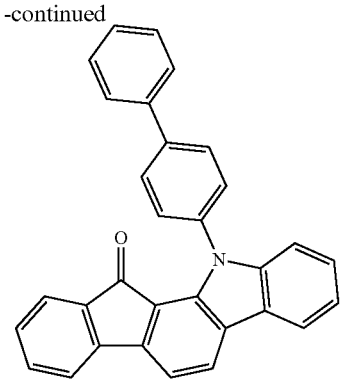

A 1 L four-neck flask is initially charged with 16 g (59 mmol) of 2a, 29.6 mL (119 mmol) of 4-bromobiphenyl and 30.5 g of NaOtBu (32 mmol) in p-xylene. To this suspension are added 0.33 g (1.5 mmol) of Pd(OAc)$_2$ and 2.9 mL of a 1 M tri-tert-butylphosphine solution in toluene. The reaction mixture is heated under reflux for 16 h. After cooling, the organic phase is removed, washed three times with 200 mL each time of water and then concentrated to dryness. The residue is subjected to hot extraction with toluene and recrystallized from toluene. The yield is 22.3 g (53 mmol, corresponding to 90%).

In an analogous manner it is possible to prepare the following compounds:

| | Reactant 1 | Reactant 2 | Product | Yield |
|---|---|---|---|---|
| 3b | | [36809-26-4] | | 83% |
| 3c | | [499128-71-1] | | 83% |

| Reactant 1 | Reactant 2 | Product | Yield |
|---|---|---|---|
| 3d 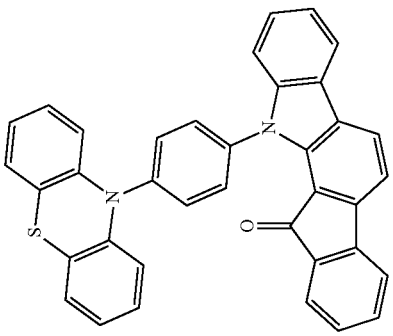 | 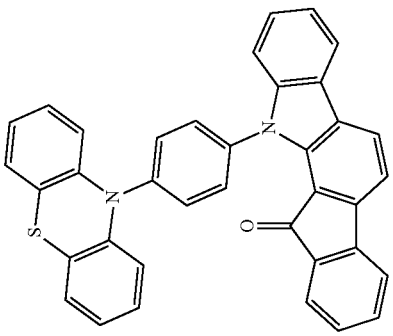 [57102-42-8] | 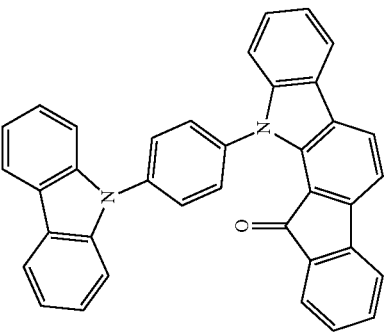 | 82% |
| 3e 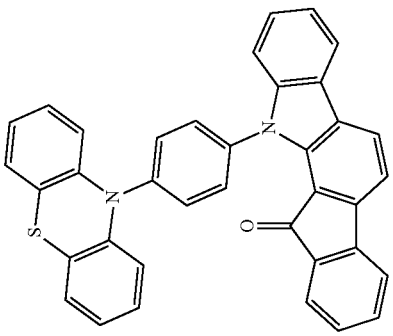 | 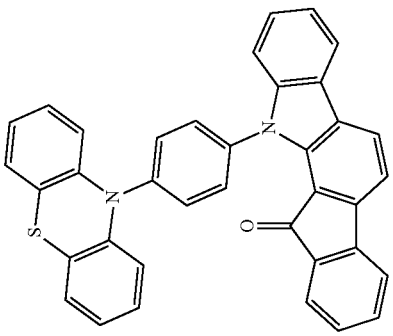 [63524-03-8] | 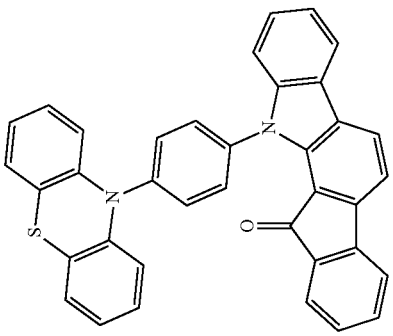 | 77% |

| | Reactant 1 | Reactant 2 | Product | Yield |
|---|---|---|---|---|
| 3f | | [94994-62-4] | | 90% |
| 3g | | [36809-26-4] | | 78% |

| | Reactant 1 | Reactant 2 | Product | Yield |
|---|---|---|---|---|
| 3h | | [89827-45-2] | | 88% |
| 3i | | | | 83% |

| | Reactant 1 | Reactant 2 | Product | Yield |
|---|---|---|---|---|
| 3j | 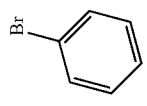 | 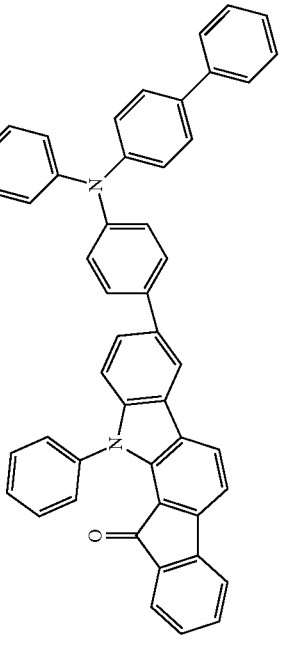 | 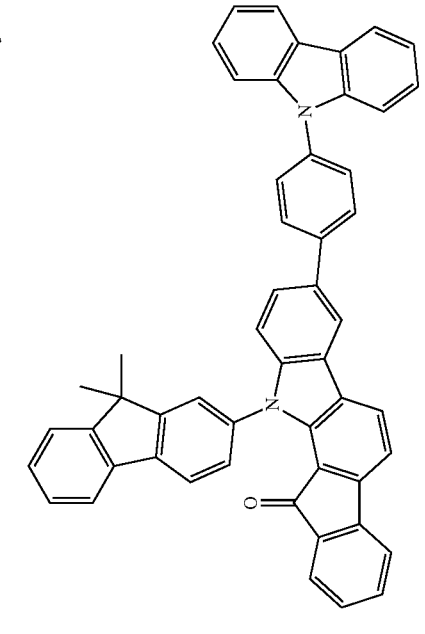 | 84% |
| 3k | 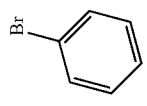 | 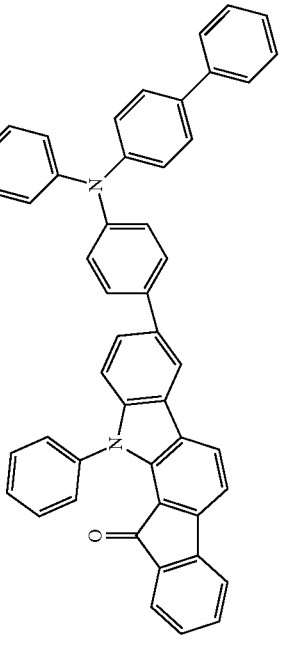 28320-31-2 | 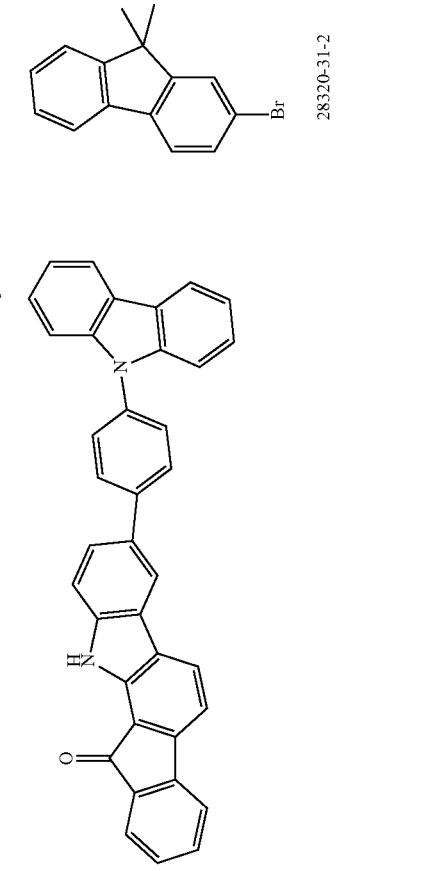 | 81% |

-continued

| | Reactant 1 | Reactant 2 | Product | Yield |
|---|---|---|---|---|
| 3l | (structure) | (structure) 92-66-0 | (structure) | 86% |
| 3m | (structure) | Br–(phenyl) | (structure) | 78% |

| | Reactant 1 | Reactant 2 | Product | Yield |
|---|---|---|---|---|
| 3n | | Br-Ph | | 76% |
| 3o | | Br-Ph | | 91% |

-continued
| | Reactant 1 | Reactant 2 | Product | Yield |
|---|---|---|---|---|
| 3p | 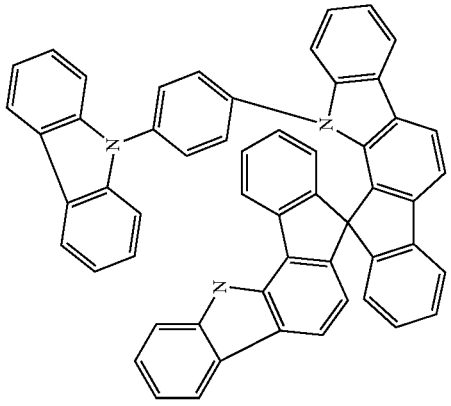 | 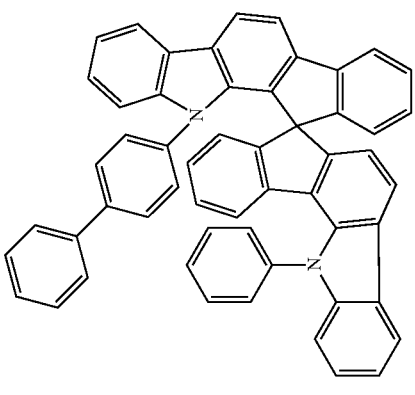 | 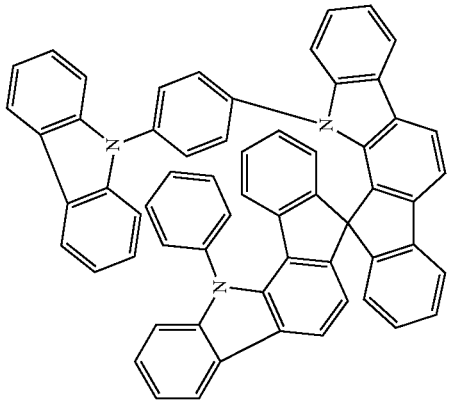 | 21%* |
| 3q | 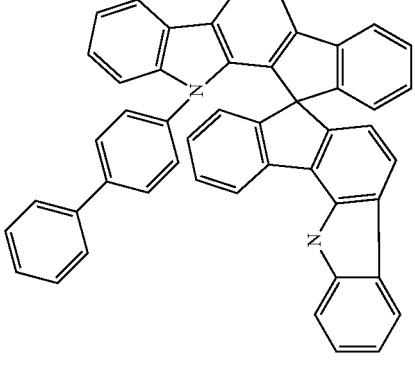 | 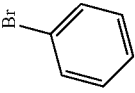 | 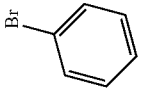 | 38%* |
*Further purification by means of recrystallization from toluene/heptane and zone sublimation (340° C., 10⁻⁵ bar) up to an HPLC purity of >99.9%.

Example 4a: Bromination

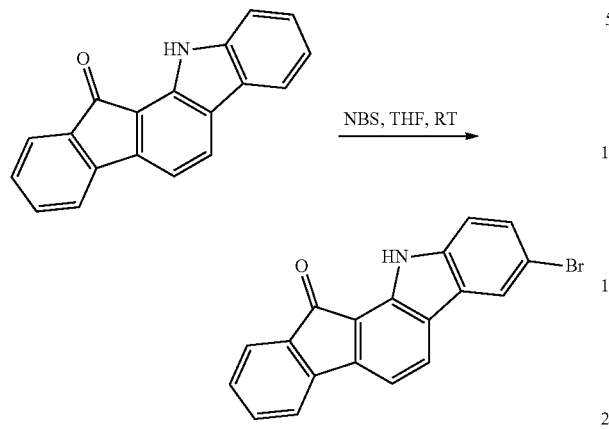

In a 1000 mL four-neck flask, 19.5 g (72.5 mmol) of 11H-11-azaindeno[2,1-a]fluoren-12-one and 13.5 g (75 mmol) of NBS are dissolved in 700 mL of THF and stirred at room temperature for 48 h until conversion is complete. This is followed by hydrolysis with 50 mL of water and removal of the organic solvents under reduced pressure. The solid obtained is extracted once by stirring with 300 mL of hot ethanol. After cooling to room temperature, the solids are filtered off. After drying under reduced pressure, the product is obtained as a colorless solid. The yield is 22.6 g (65 mmol, corresponding to 90% of theory).

Example 5a: Borylation

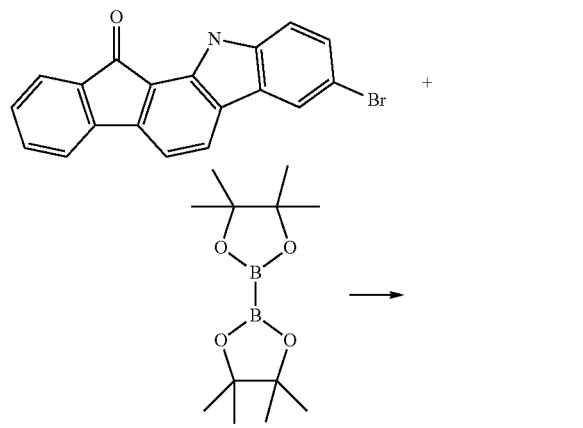

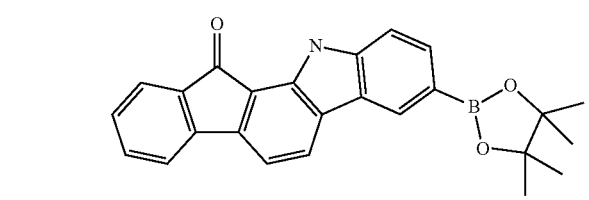

In a 2 L four-neck flask, 24.7 g (71 mmol) of 8-bromo-11H-11-azaindeno[2,1-a]fluoren-12-one, 21.9 g (86 mmol) of bispinacolatodiborane (73183-34-3), 21.7 g (221 mmol) of potassium acetate and 1.7 g (2.1 mmol) of 1,1-bis(diphenylphosphino)ferrocenedichloropalladium(II) complex with DCM were heated under reflux in 1000 mL of anhydrous dioxane for 16 h until conversion was complete. After cooling down to room temperature, the organic phase is extended with ethyl acetate, washed three times with 300 mL of water and dried over sodium sulfate. The combined organic phases are concentrated to dryness by rotary evaporation. After recrystallization from heptane, the product is obtained in solid form. The yield is 21.3 g (54 mmol; 61%).

Example 6a

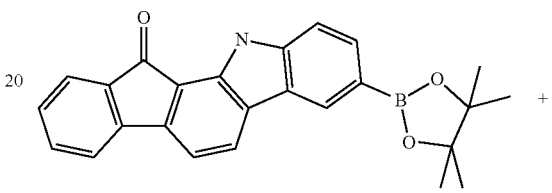

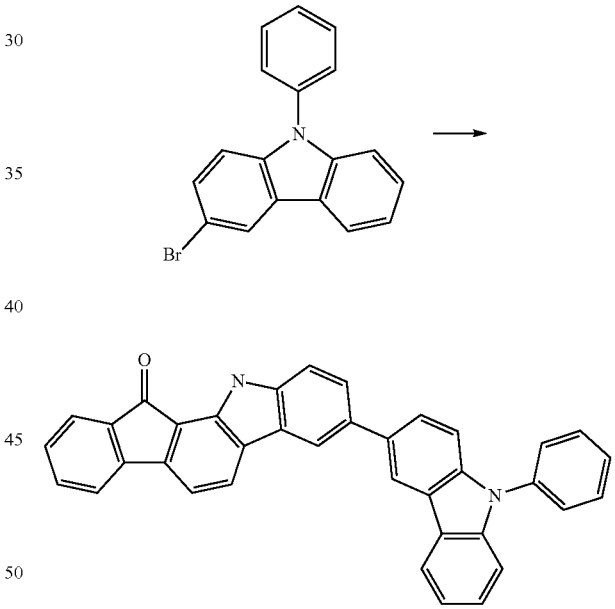

12.6 g (32 mmol) of 8-(4,4,5,5-tetramethyl-[1,3,2]dioxaborolan-2-yl)-1H-11-azaindeno[2,1-a]fluoren-12-one, 10.3 g (32 mmol) of 3-bromo-9-phenyl-9H-carbazole [1153-85-1] and 31 ml (63 mmol) of $Na_2CO_3$ (2 M solution) are suspended in 120 mL of toluene and 120 mL of ethanol. 0.73 g (0.63 mmol) of $Pd(PPh_3)_4$ is added to this suspension, and the reaction mixture is heated under reflux for 16 h. After cooling, the organic phase is removed, filtered through silica gel, washed three times with 200 mL of water and then concentrated to dryness. The residue is recrystallized from toluene. The yield is 14.8 g (29 mmol), corresponding to 91% of theory.

In an analogous manner, it is possible to prepare the following compounds:

| | Reactant 1 | Reactant 2 | Product | Yield |
|---|---|---|---|---|
| 6b | | [36809-26-4] | | 83% |
| 6c | | [499128-71-1] | | 83% |
| 6d | | [57102-42-8] | | 82% |
| 6e | | [63524-03-8] | | 77% |

-continued
| Reactant 1 | Reactant 2 | Product | Yield |
|---|---|---|---|
| 6f | [94994-62-4] | | 90% |
| 6g | [89827-45-2] | | 78% |
Example 7a: 12'-Biphenyl-4-ylspiro[9H-fluoren-9,11(12H)-indeno[2,1a]carbazole]
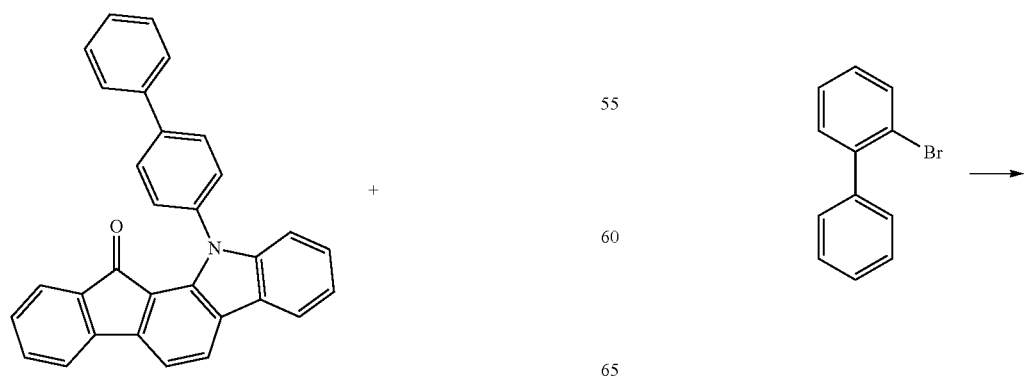

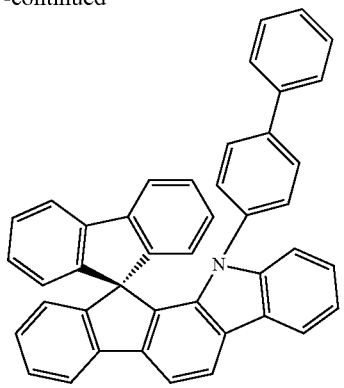

A 1 L four-neck flask is initially charged with 23 g (99 mol) of 2-bromobiphenyl in 100 mL of THF and cooled to −78° C. By means of a dropping funnel, 41.0 mL (103 mmol) of n-butyllithium (2.5 M in n-hexane) are added dropwise at this temperature and the mixture is stirred for 1 h. Subsequently, 20.6 g (49 mmol) of 11-biphenyl-4-yl-11H-11-azaindeno[2,1-a]fluoren-12-one, dissolved in 300 mL of THF, are added by means of a dropping funnel and the mixture is warmed to room temperature within 3 h. This is followed by hydrolysis with 500 mL of water and removal of the organic solvents on a rotary evaporator. The solid that precipitates out is filtered, suspended in 400 mL of glacial acetic acid and, after addition of 150 mL of concentrated hydrochloric acid, stirred at 100° C. for 2 h. After cooling to room temperature, hydrolysis is effected with 400 mL of water, and the precipitated solids are filtered off and washed with 200 mL of water, ethanol (200 mL) and finally with 200 mL of n-heptane. The solids are subjected to hot extraction and recrystallization with n-heptane/toluene over alumina. 20.1 g (42.0 mmol, corresponding to 85%) of the product are obtained as a white solid. Further purification is effected by means of recrystallization from toluene/heptane and zone sublimation (265° C., $10^{-5}$ bar). The yield is 8.4 g (15 mmol, corresponding to 32%, HPLC purity >99.9%).

In an analogous manner, it is possible to prepare the following compounds:

| | Reactant 1 | Reactant 2 | Product | Yield |
|---|---|---|---|---|
| 7b | | 2052-07-5 | | 31% |
| 7c | | 2052-07-5 | | 27% |

| | Reactant 1 | Reactant 2 | Product | Yield |
|---|---|---|---|---|
| 7d | | 2052-07-5 | | 36% |
| 7e | | 2052-07-5 | | 35% |

| | Reactant 1 | Reactant 2 | Product | Yield |
|---|---|---|---|---|
| 7f | | 2052-07-5 | | 38% |
| 7g | | 2052-07-5 | | 39% |

| | Reactant 1 | Reactant 2 | Product | Yield |
|---|---|---|---|---|
| 7h | (structure) | Br-biphenyl, 2052-07-5 | (structure) | 36% |
| 7i | (structure) | Br-biphenyl, 2052-07-5 | (structure) | 33% |

| | Reactant 1 | Reactant 2 | Product | Yield |
|---|---|---|---|---|
| 7j | | Br-biphenyl 2052-07-5 | | 35% |
| 7k | | Br-biphenyl 2052-07-5 | | 27% |
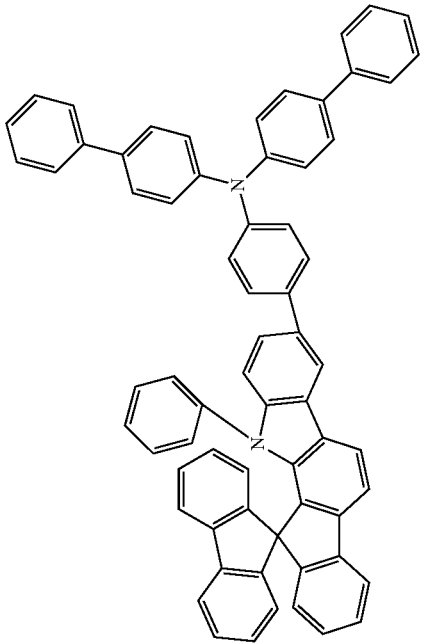

| | Reactant 1 | Reactant 2 | Product | Yield |
|---|---|---|---|---|
| 7l | | 2052-07-5 | | 29% |
| 7m | | 2052-07-5 | | 36% |

-continued

| | Reactant 1 | Reactant 2 | Product | Yield |
|---|---|---|---|---|
| 7n | | 2052-07-5 | | 37% |
| 7o comp. | | 2052-07-5 | | 38% |

| | Reactant 1 | Reactant 2 | Product | Yield |
|---|---|---|---|---|
| 7p | 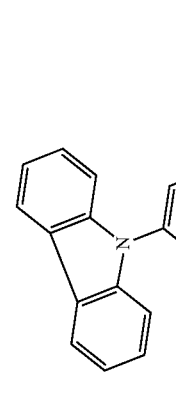 | 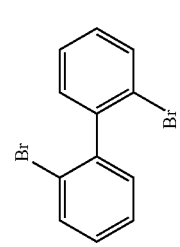 13029-09-9 | 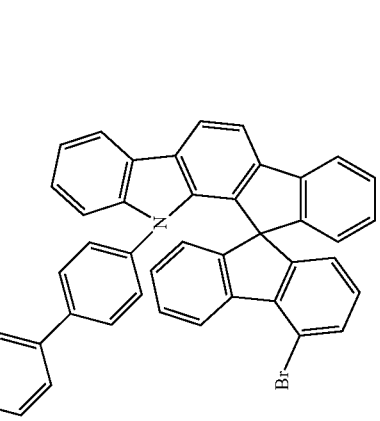 | 64% (without sublimation) |
| 7q | 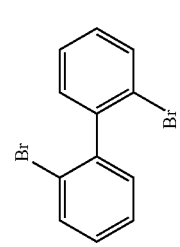 | 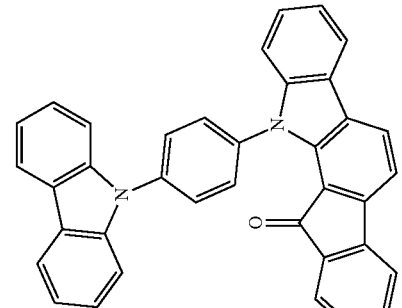 13029-09-9 | 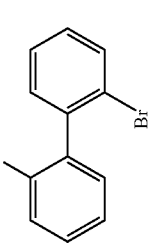 | 65% (without sublimation) |

Production of the OLEDs

In examples C1 to I16 which follow (see tables 1 and 2), the data of various OLEDs are presented.

Pretreatment for Examples C1-I16

Glass plates coated with structured ITO (indium tin oxide) of thickness 50 nm, for improved processing, are coated with 20 nm of PEDOT:PSS (poly(3,4-ethylenedioxythiophene) poly(styrenesulfonate), purchased as CLEVIOS™ P VP AI 4083 from Heraeus Precious Metals GmbH Deutschland, spun on from aqueous solution). These coated glass plates form the substrates to which the OLEDs are applied.

The OLEDs basically have the following layer structure: substrate/hole transport layer (HTL)/optional interlayer (IL)/electron blocker layer (EBL)/emission layer (EML)/optional hole blocker layer (HBL)/electron transport layer (ETL)/optional electron injection layer (EIL) and finally a cathode. The cathode is formed by an aluminum layer of thickness 100 nm. The exact structure of the OLEDs can be found in Table 1. A reference such as "7a" means the compound of example 7a. The further materials used for production of the OLEDs are shown in Table 3.

All materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as IC1:IC3:TEG1 (55%:35%:10%) mean here that the material IC1 is present in the layer in a proportion by volume of 55%, IC3 in a proportion of 35% and TEG1 in a proportion of 10%. Analogously, the electron transport layer may also consist of a mixture of two materials.

The OLEDs are characterized in a standard manner. For this purpose, the electroluminescence spectra, the current efficiency (measured in cd/A), the power efficiency (measured in lm/W) and the external quantum efficiency (EQE, measured in percent) are, as a function of luminance, calculated from current-voltage-luminance characteristics (IUL characteristics) assuming Lambertian radiation characteristics. The electroluminescence spectra are determined at a luminance of 1000 cd/m$^2$, and the CIE 1931 x and y color coordinates are calculated therefrom. The parameter U1000 in Table 2 refers to the voltage which is required for a luminance of 1000 cd/m$^2$. CE1000 and PE1000 respectively refer to the current and power efficiencies which are achieved at 1000 cd/m$^2$. Finally, EQE1000 refers to the external quantum efficiency at an operating luminance of 1000 cd/m$^2$.

The data for the various OLEDs are collated in Table 2. Example C1 is a comparative example according to the prior art; examples I11-I16 show data of OLEDs of the invention.

Some of the examples are elucidated in detail hereinafter, in order to illustrate the advantages of the OLEDs of the invention.

Use of Mixtures of the Invention in the Emission Layer of Phosphorescent OLEDs The materials of the invention, when used as matrix materials in phosphorescent OLEDs, show improvements in power efficiency compared to the prior art. By using the compound 7a of the invention in combination with the green-emitting dopant TEG1 and the matrix ST1, it is possible to achieve a rise in power efficiency by about 15% compared to the prior art 70 (examples C1, I1).

TABLE 1

Structure of the OLEDs

| Ex. | HTL thickness | IL thickness | EBL thickness | EML thickness | HBL thickness | ETL thickness | EIL thickness |
|---|---|---|---|---|---|---|---|
| C1 | SpA1 70 nm | HATCN 5 nm | SpMA1 90 nm | ST1:7o:TEG1 (30%:58%:12%) 30 nm | IC1 10 nm | ST2:LiQ (50%:50%) 30 nm | — |
| I1 | SpA1 70 nm | HATCN 5 nm | SpMA1 90 nm | ST1:7a:TEG1 (30%:58%:12%) 30 nm | IC1 10 nm | ST2:LiQ (50%:50%) 30 nm | — |
| I2 | SpA1 70 nm | HATCN 5 nm | SpMA1 90 nm | ST1:7b:TEG1 (44%:44%:12%) 30 nm | IC1 10 nm | ST2:LiQ (50%:50%) 30 nm | — |
| I3 | SpA1 70 nm | HATCN 5 nm | SpMA1 90 nm | ST1:7c:TEG1 (58%:30%:12%) 30 nm | IC1 10 nm | ST2:LiQ (50%:50%) 30 nm | — |
| I4 | SpA1 70 nm | HATCN 5 nm | SpMA1 90 nm | ST1:7d:TEG1 (32%:56%:12%) 30 nm | IC1 10 nm | ST2:LiQ (50%:50%) 30 nm | — |
| I5 | SpA1 90 nm | HATCN 5 nm | SpMA1 130 nm | IC2:7e:TER1 (30%:60%:10%) 40 nm | — | ST2:LiQ (50%:50%) 40 nm | — |
| I6 | SpA1 70 nm | HATCN 5 nm | SpMA1 90 nm | ST1:7f:TEG1 (32%:56%:12%) 30 nm | IC1 10 nm | ST2:LiQ (50%:50%) 30 nm | — |
| I7 | SpA1 70 nm | HATCN 5 nm | SpMA1 90 nm | ST1:7g:TEG1 (44%:44%:12%) 30 nm | IC1 10 nm | ST2:LiQ (50%:50%) 30 nm | — |
| I8 | SpA1 70 nm | HATCN 5 nm | SpMA1 90 nm | ST1:7h:TEG1 (30%:58%:12%) 30 nm | IC1 10 nm | ST2:LiQ (50%:50%) 30 nm | — |
| I9 | SpA1 70 nm | HATCN 5 nm | SpMA1 90 nm | ST1:7i:TEG1 (44%:44%:12%) 30 nm | IC1 10 nm | ST2:LiQ (50%:50%) 30 nm | — |
| I10 | SpA1 70 nm | HATCN 5 nm | SpMA1 90 nm | ST1:7j:TEG1 (56%:32%:12%) 30 nm | IC1 10 nm | ST2:LiQ (50%:50%) 30 nm | — |
| I11 | SpA1 70 nm | HATCN 5 nm | SpMA1 90 nm | ST1:7k:TEG1 (34%:54%:12%) 30 nm | IC1 10 nm | ST2:LiQ (50%:50%) 30 nm | — |
| I12 | SpA1 90 nm | HATCN 5 nm | SpMA1 130 nm | IC2:7l:TER1 (30%:60%:10%) 40 nm | — | ST2:LiQ (50%:50%) 40 nm | — |
| I13 | SpA1 90 nm | HATCN 5 nm | SpMA1 130 nm | IC2:7m:TER1 (45%:45%:10%) 40 nm | — | ST2:LiQ (50%:50%) 40 nm | — |
| I14 | SpA1 90 nm | HATCN 5 nm | SpMA1 130 nm | IC2:7n:TER1 (30%:60%:10%) 40 nm | — | ST2:LiQ (50%:50%) 40 nm | — |

TABLE 1-continued

Structure of the OLEDs

| Ex. | HTL thickness | IL thickness | EBL thickness | EML thickness | HBL thickness | ETL thickness | EIL thickness |
|---|---|---|---|---|---|---|---|
| I15 | SpA1 70 nm | HATCN 5 nm | SpMA1 90 nm | ST1:3p:TEG1 (32%:56%:12%) 30 nm | IC1 10 nm | ST2:LiQ (50%:50%) 30 nm | — |
| I16 | SpA1 70 nm | HATCN 5 nm | SpMA1 90 nm | ST1:3q:TEG1 (32%:56%:12%) 30 nm | IC1 10 nm | ST2:LiQ (50%:50%) 30 nm | — |

TABLE 2

| Ex. | U1000 (V) | CE1000 (cd/A) | PE1000 (lm/W) | EQE 1000 | CIE x/y at 1000 cd/m$^2$ |
|---|---|---|---|---|---|
| C1 | 3.4 | 58 | 54 | 15.6% | 0.33/0.62 |
| I1 | 3.2 | 64 | 62 | 17.2% | 0.34/0.63 |
| I2 | 3.4 | 68 | 63 | 18.4% | 0.34/0.62 |
| I3 | 3.3 | 67 | 64 | 18.1% | 0.34/0.63 |
| I4 | 3.1 | 63 | 64 | 16.9% | 0.33/0.62 |
| I5 | 4.3 | 11 | 8 | 12.1% | 0.67/0.33 |
| I6 | 3.3 | 61 | 58 | 16.5% | 0.33/0.62 |
| I7 | 3.5 | 67 | 60 | 17.9% | 0.34/0.62 |
| I8 | 3.4 | 65 | 60 | 17.6% | 0.33/0.63 |
| I9 | 3.6 | 70 | 61 | 18.7% | 0.34/0.62 |
| I10 | 3.4 | 68 | 63 | 18.2% | 0.33/0.62 |
| I11 | 3.2 | 62 | 61 | 16.6% | 0.33/0.63 |
| I12 | 4.1 | 13 | 10 | 12.4% | 0.66/0.34 |
| I13 | 4.2 | 14 | 10 | 13.3% | 0.67/0.33 |
| I14 | 4.3 | 14 | 10 | 12.8% | 0.66/0.34 |
| I15 | 3.4 | 63 | 58 | 16.8% | 0.33/0.62 |
| I16 | 3.5 | 65 | 58 | 17.5% | 0.34/0.63 |

TABLE 3

Structural formulae of the materials for the OLEDs

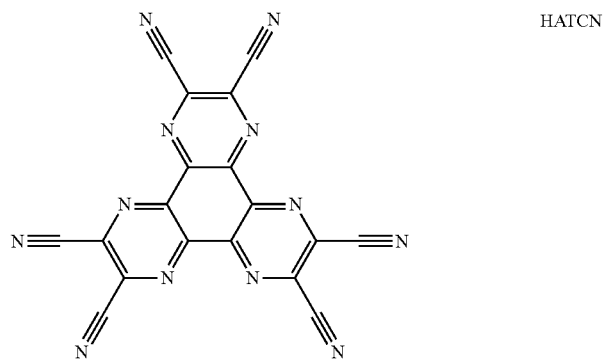

HATCN

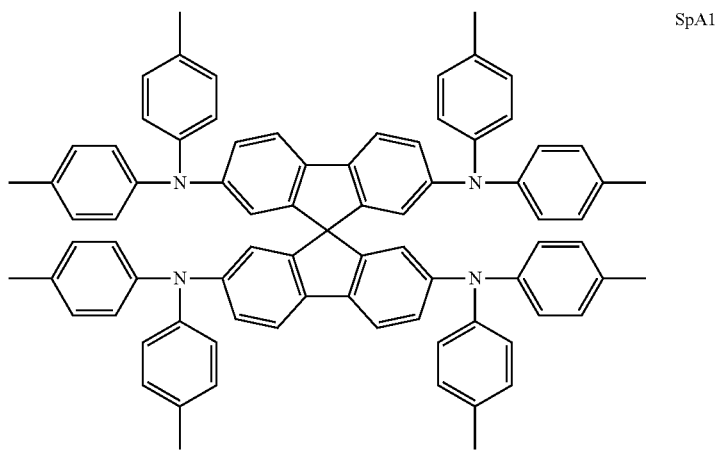

SpA1

TABLE 3-continued
Structural formulae of the materials for the OLEDs
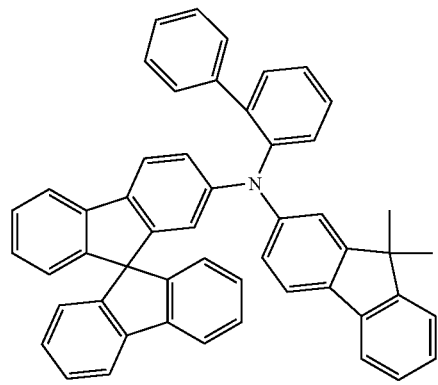 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
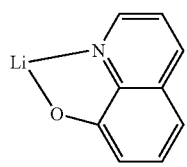
LiQ
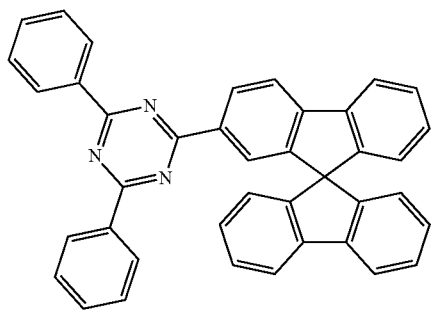 [SMILES: c1ccc(-c2nc(-c3ccccc3)nc(-c3ccc4c(c3)C3(c5ccccc5-c5ccccc53)c3ccccc3-4)n2)cc1]
ST1
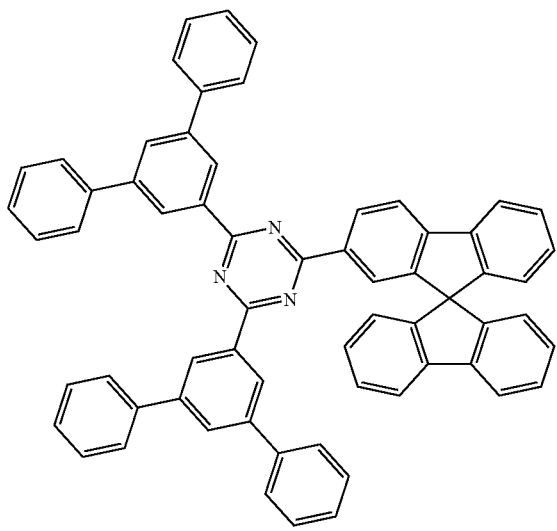 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST2

TABLE 3-continued
Structural formulae of the materials for the OLEDs
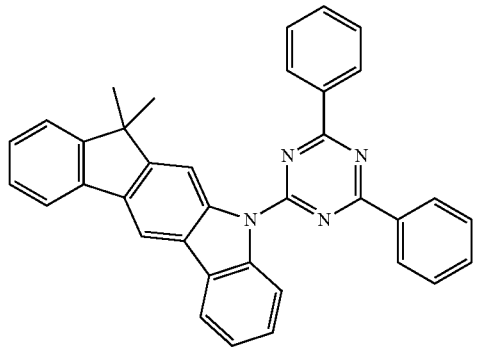 [SMILES: CC1(C)c2ccccc2-c2cc3c4ccccc4n(-c4nc(-c5ccccc5)nc(-c5ccccc5)n4)c3cc21]
IC1
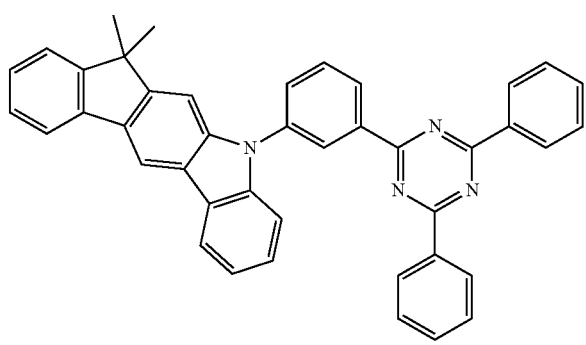 [SMILES: CC1(C)c2ccccc2-c2cc3c4ccccc4n(-c4cccc(-c5nc(-c6ccccc6)nc(-c6ccccc6)n5)c4)c3cc21]
IC2
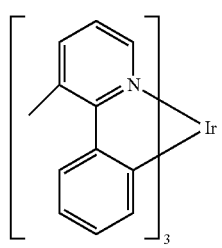
TEG1
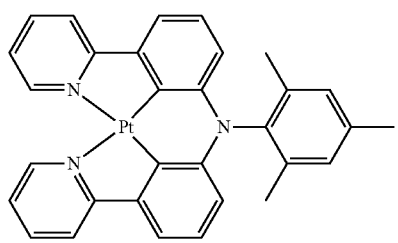
TER1

The invention claimed is:
1. A compound of formula (3)

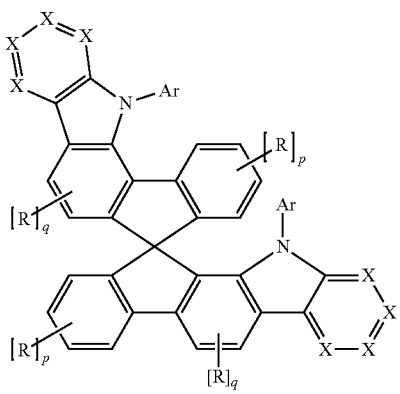

Formula (3)

where the symbols and indices used are as follows:
X is the same or different at each instance and is $CR^1$ or N; or two adjacent Xs are a group of the following formula (4), (5) or (6):

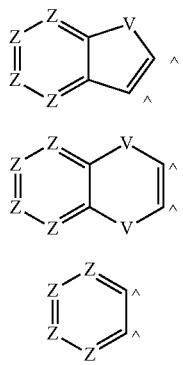

Formula (4)

Formula (5)

Formula (6)

where ^ indicates the corresponding adjacent X groups in the formula (2) or (3);
V is the same or different at each instance and is $C(R^1)_2$, $NR^1$, O, S, $BR^1$, $Si(R^1)_2$ or C=O;
Z is the same or different at each instance and is $CR^1$ or N;
Ar is the same or different at each instance and is an aromatic ring system which has 6 to 40 aromatic ring atoms and may be substituted by one or more $R^2$ radicals, or a heteroaromatic ring system which has 5 to 40 aromatic ring atoms, does not contain any electron-deficient heteroaryl groups and may be substituted by one or more $R^2$ radicals;
R, $R^1$ is the same or different at each instance and is selected from the group consisting of H, D, F, Cl, Br, I, CN, $NO_2$, $N(Ar^1)_2$, $N(R^3)_2$, $C(=O)Ar^1$, $C(=O)R^3$, $P(=O)(Ar^1)_2$, $P(Ar^1)_2$, $B(Ar^1)_2$, $Si(Ar^1)_3$, $Si(R^3)_3$, a straight-chain alkyl, alkoxy or thioalkyl group having 1 to 20 carbon atoms or a branched or cyclic alkyl, alkoxy or thioalkyl group having 3 to 20 carbon atoms or an alkenyl group having 2 to 20 carbon atoms, each of which may be substituted by one or more $R^3$ radicals, where one or more nonadjacent $CH_2$ groups may be replaced by $R^3C=CR^3$, $Si(R^3)_2$, C=O, C=S, C=$NR^3$, P(=O)($R^3$), SO, $SO_2$, $NR^3$, O, S or $CONR^3$ and where one or more hydrogen atoms may be replaced by D, F, Cl, Br, I, CN or $NO_2$, an aromatic or heteroaromatic ring system which has 5 to 40 aromatic ring atoms and may be substituted in each case by one or more $R^3$ radicals, an aryloxy or heteroaryloxy group which has 5 to 40 aromatic ring atoms and may be substituted by one or more $R^3$ radicals, or an aralkyl or heteroaralkyl group which has 5 to 40 aromatic ring atoms and may be substituted by one or more $R^3$ radicals; at the same time, it is optionally possible for two $R^1$ substituents bonded to the same carbon atom to form a monocyclic or polycyclic, aliphatic, aromatic or heteroaromatic ring system which may be substituted by one or more $R^3$ radicals;
$R^2$ is the same or different at each instance and is selected from the group consisting of H, D, F, Cl, Br, I, CN, $NO_2$, $N(Ar^1)_2$, $N(R^3)_2$, $C(=O)Ar^1$, $C(=O)R^3$, $P(=O)(Ar^1)_2$, $P(Ar^1)_2$, $B(Ar^1)_2$, $Si(Ar^1)_3$, $Si(R^3)_3$, a straight-chain alkyl, alkoxy or thioalkyl group having 1 to 20 carbon atoms or a branched or cyclic alkyl, alkoxy or thioalkyl group having 3 to 20 carbon atoms or an alkenyl group having 2 to 20 carbon atoms, each of which may be substituted by one or more $R^3$ radicals, where one or more nonadjacent $CH_2$ groups may be replaced by $R^3C=CR^3$, $Si(R^3)_2$, C=O, C=S, C=$NR^3$, P(=O)($R^3$), SO, $SO_2$, $NR^3$, O, S or $CONR^3$ and where one or more hydrogen atoms may be replaced by D, F, Cl, Br, I, CN or $NO_2$, an aromatic or heteroaromatic ring system which has 5 to 40 aromatic ring atoms, does not contain any electron-deficient heteroaryl groups and may be substituted in each case by one or more $R^3$ radicals, an aryloxy or heteroaryloxy group which has 5 to 40 aromatic ring atoms, does not contain any electron-deficient heteroaryl groups and may be substituted by one or more $R^3$ radicals, or an aralkyl or heteroaralkyl group which has 5 to 40 aromatic ring atoms, does not contain any electron-deficient heteroaryl groups and may be substituted by one or more $R^3$ radicals; at the same time, it is possible for two or more adjacent $R^3$ substituents together to form a mono- or polycyclic aliphatic ring system;
$Ar^1$ is the same or different at each instance and is an aromatic or heteroaromatic ring system which has 5-30 aromatic ring atoms and may be substituted by one or more nonaromatic $R^3$ radicals; at the same time, two $Ar^1$ radicals bonded to the same nitrogen atom, phosphorus atom or boron atom may also be bridged to one another by a single bond or a bridge selected from $N(R^3)$, $C(R^3)_2$, O and S;
$R^3$ is the same or different at each instance and is selected from the group consisting of H, D, F, CN, an aliphatic hydrocarbyl radical having 1 to 20 carbon atoms and an aromatic or heteroaromatic ring system having 5 to 30 aromatic ring atoms in which one or more hydrogen atoms may be replaced by D, F, Cl, Br, I or CN, where two or more adjacent $R^3$ substituents together may form a mono- or polycyclic, aliphatic ring system;
p is the same or different at each instance and is 0, 1, 2, 3 or 4;
q is 0, 1 or 2.

2. The compound as claimed in claim 1, wherein X is the same or different at each instance and is $CR^1$ or N, where not more than one X group per cycle is N, or in that two adjacent X groups are a group of the formula (4), where Z is the same or different at each instance and is $CR^1$ and V is the same or different at each instance and is NR$^1$, C(R$^1$)$_2$, O or S, and the rest of the X groups in the cycle are CR$^1$.

3. The compound as claimed in claim 1, wherein the compound is selected from the compounds of the formula (15)

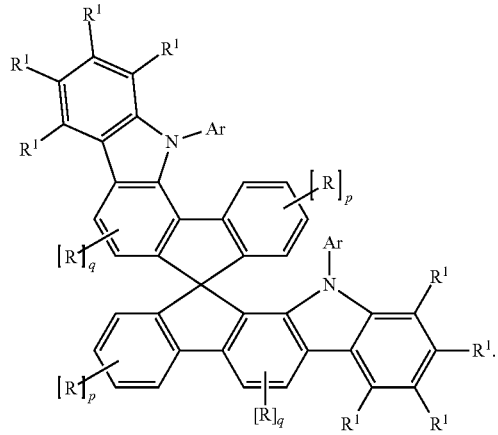

Formula (15)

4. The compound as claimed in claim 1, wherein the compound is selected from the compounds of the formula (15a)

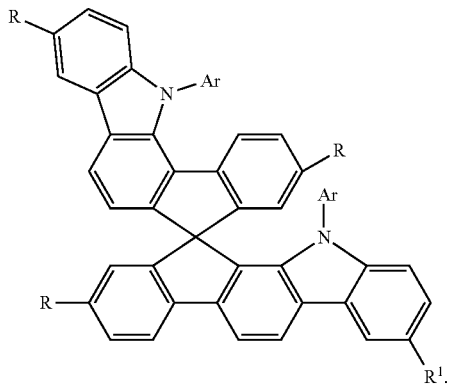

Formula (15a)

5. The compound as claimed in claim 1, wherein R is the same or different at each instance and is selected from the group consisting of H, F, CN, N(Ar$^1$)$_2$, a straight-chain alkyl group having 1 to 10 carbon atoms and a branched or cyclic alkyl group having 3 to 10 carbon atoms and an aromatic ring system which has 6 to 30 aromatic ring atoms and may be substituted by one or more nonaromatic R$^3$ radicals.

6. The compound as claimed in claim 1, wherein the compound is selected from the compounds of the formula (15b)

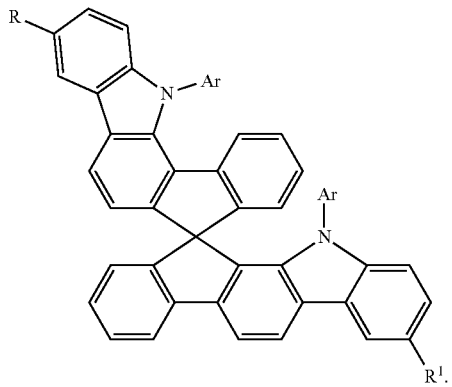

Formula (15b)

7. The compound as claimed in claim 1, wherein the compounds of formula (3) contains a total of at least 12 aromatic ring atoms in the Ar, R$^1$ and R$^2$ substituents.

8. The compound as claimed in claim 1, wherein Ar is selected from the groups of the formulae Ar-1 to Ar-58

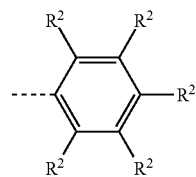

Ar-1

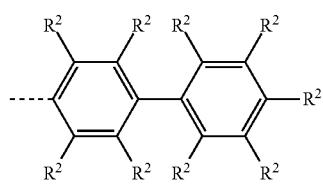

Ar-2

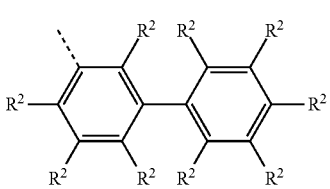

Ar-3

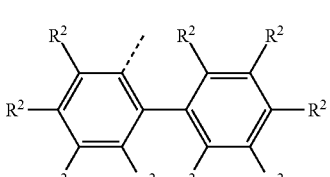

Ar-4

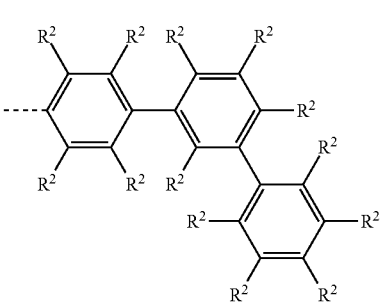

Ar-5

-continued
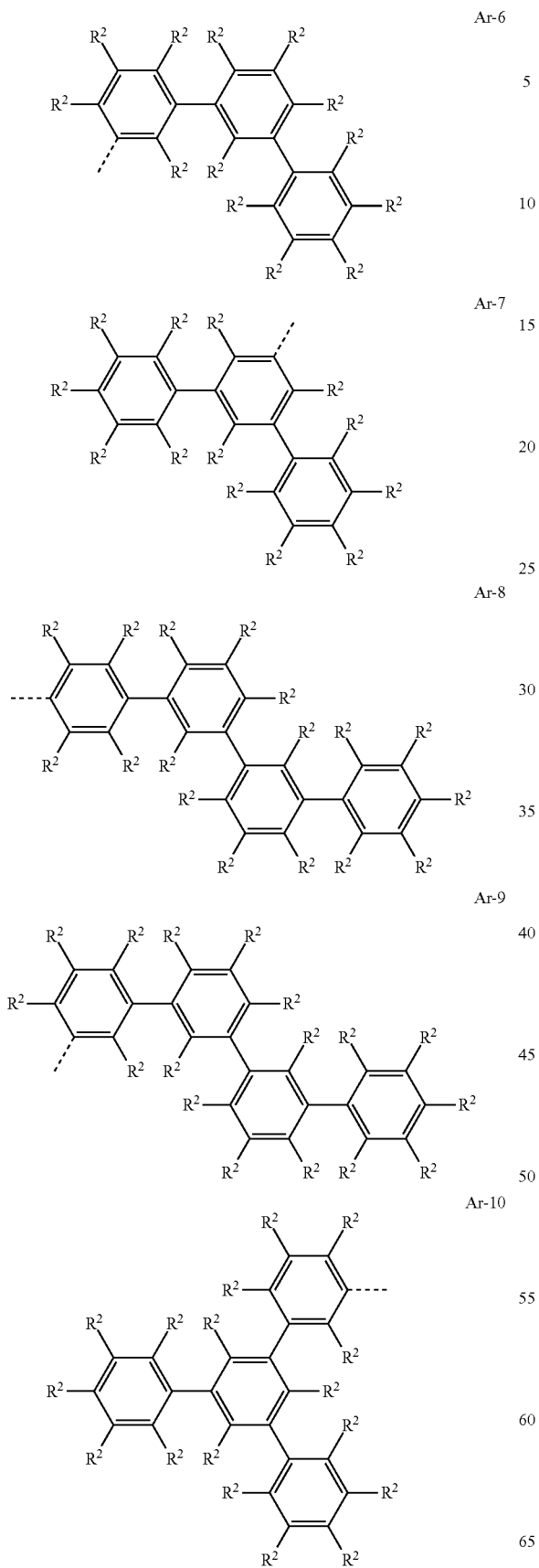
Ar-6
Ar-7
Ar-8
Ar-9
Ar-10
-continued
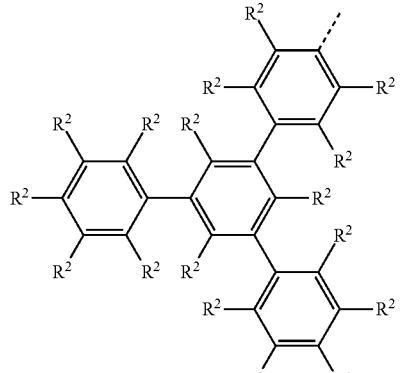
Ar-11
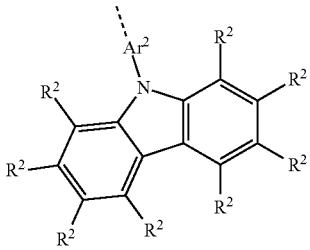
Ar-12
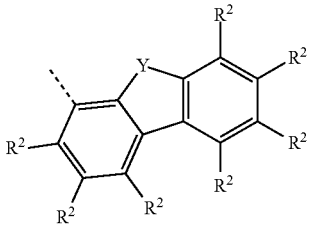
Ar-13
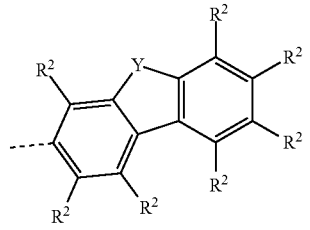
Ar-14
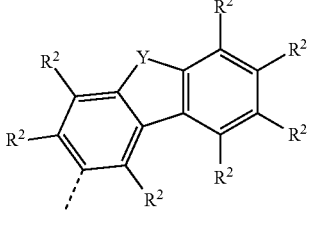
Ar-15
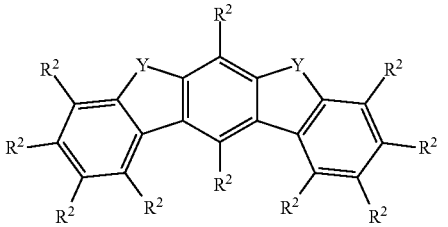
Ar-16

Ar-17 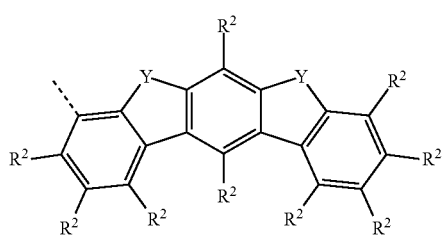
Ar-18 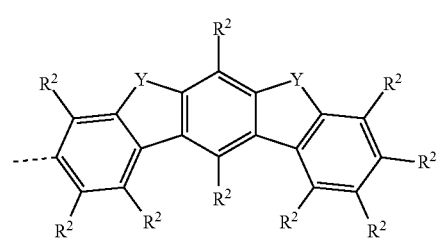
Ar-19 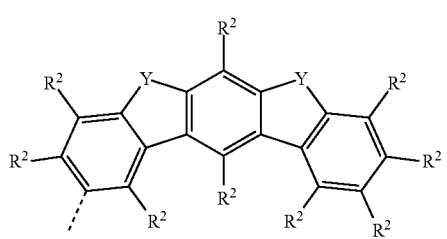
Ar-20 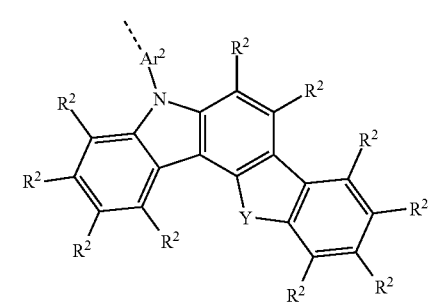
Ar-21 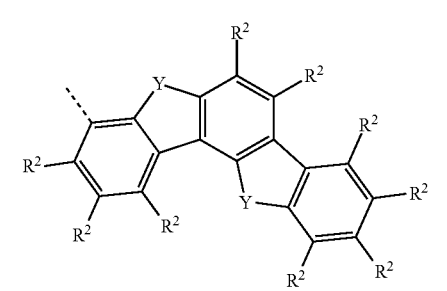
Ar-22 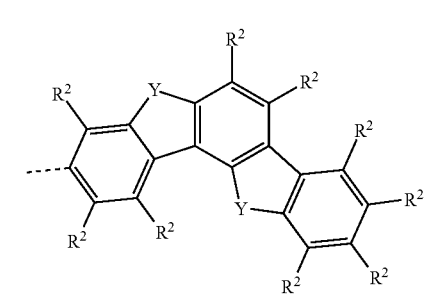
Ar-23 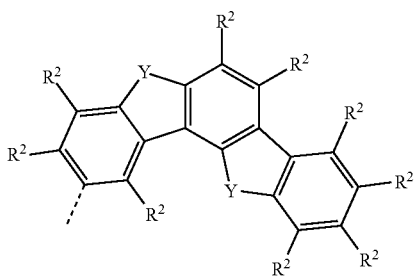
Ar-24 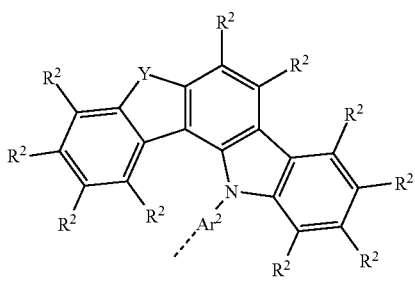
Ar-25 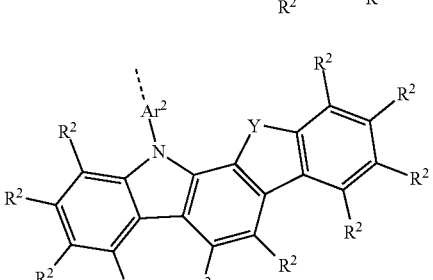
Ar-26 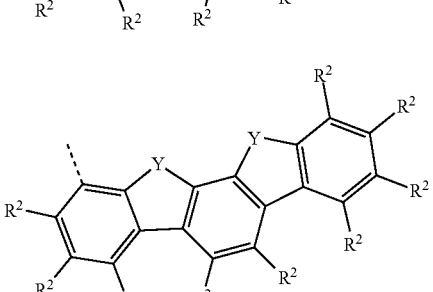
Ar-27 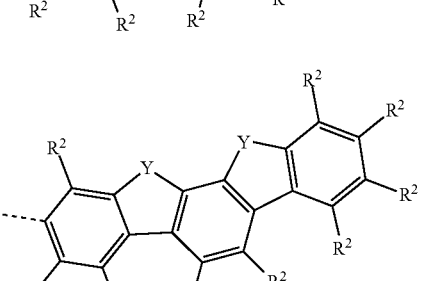
Ar-28 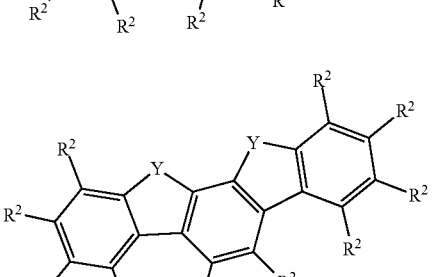

-continued
Ar-29
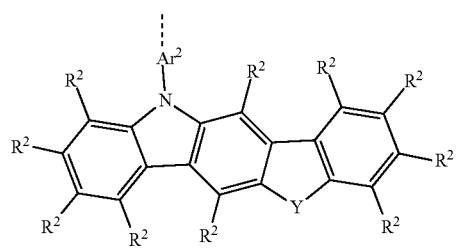
Ar-30
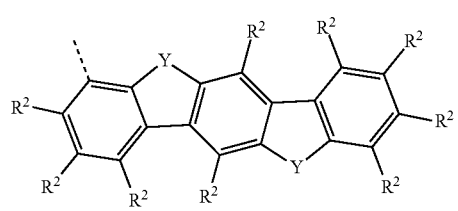
Ar-31
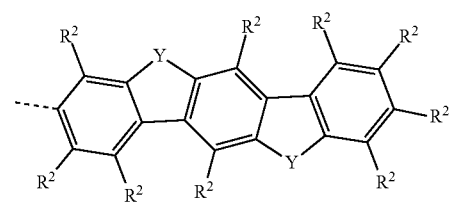
Ar-32
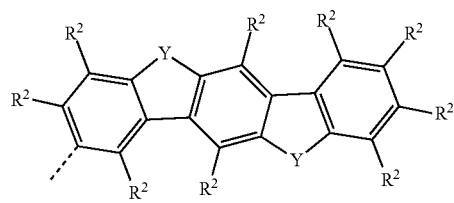
Ar-33
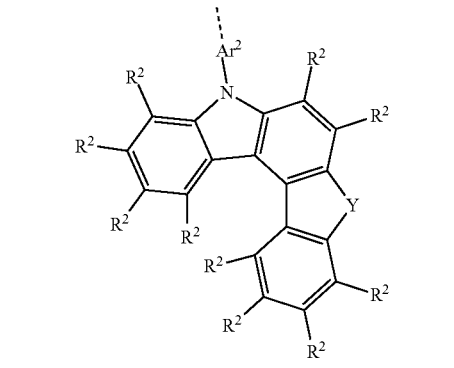
Ar-34
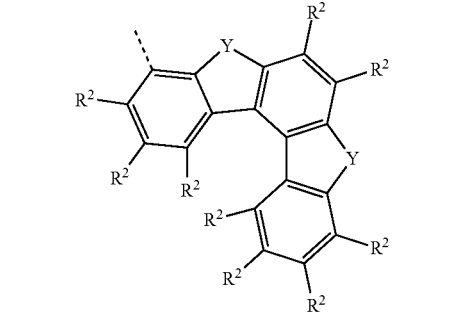
-continued
Ar-35
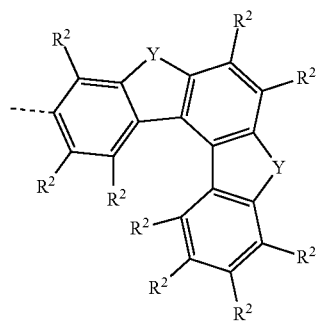
Ar-36
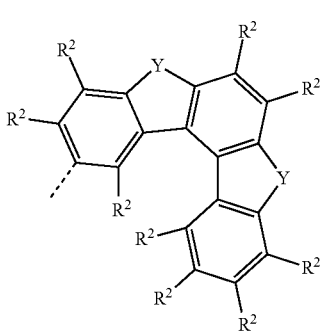
Ar-37
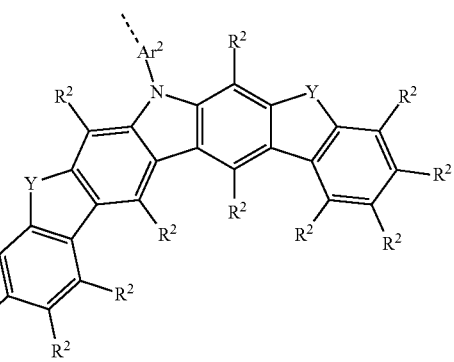
Ar-38
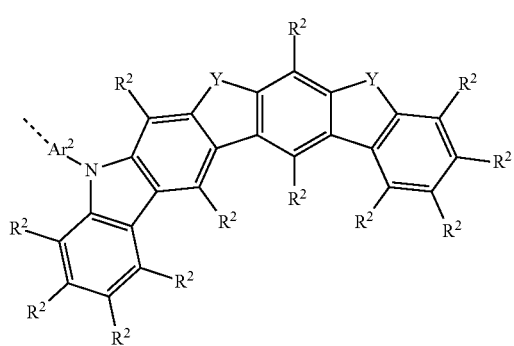

-continued
Ar-39
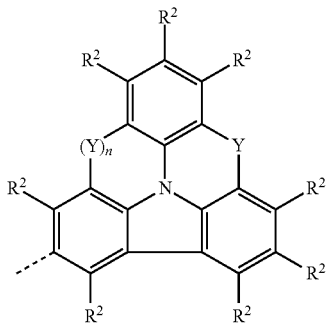
Ar-40
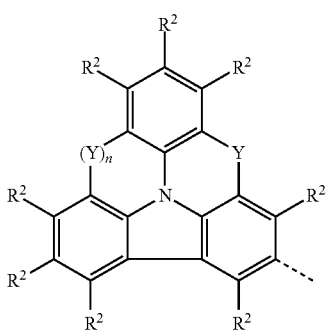
Ar-41
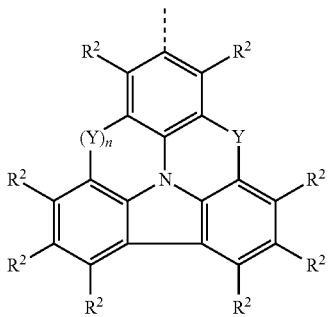
Ar-42
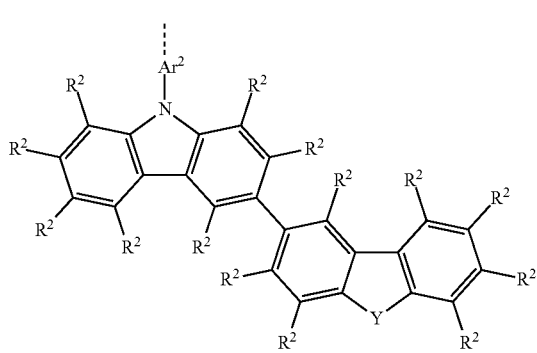
Ar-43
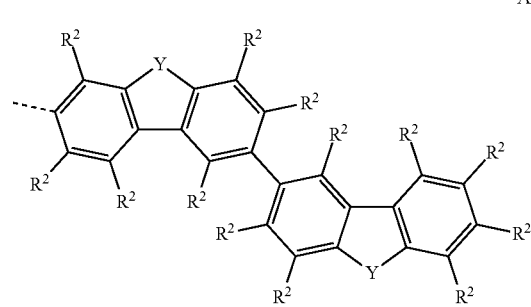
-continued
Ar-44
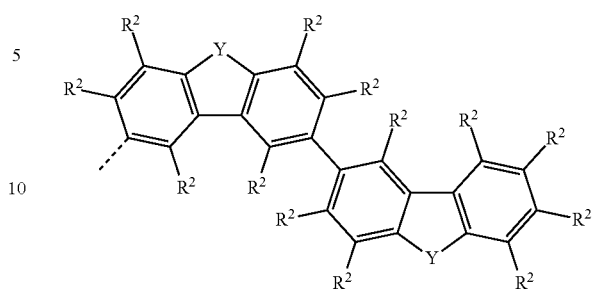
Ar-47
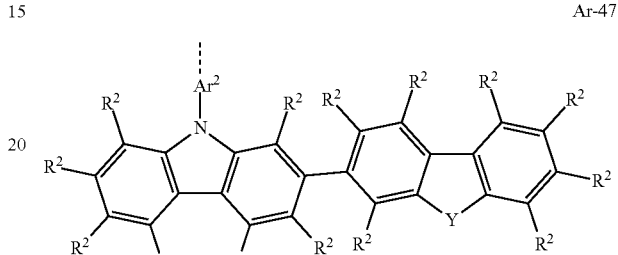
Ar-48
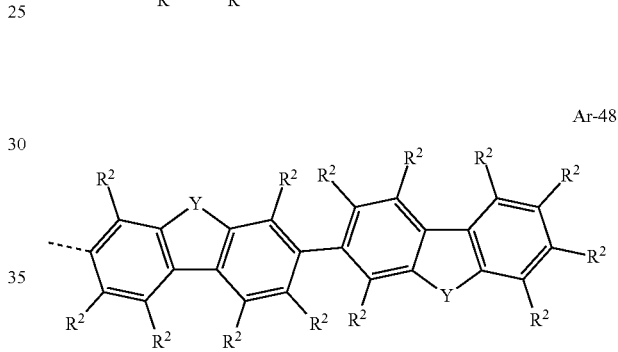
Ar-49
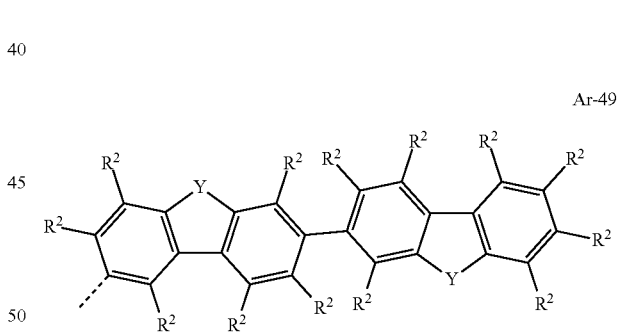
Ar-50
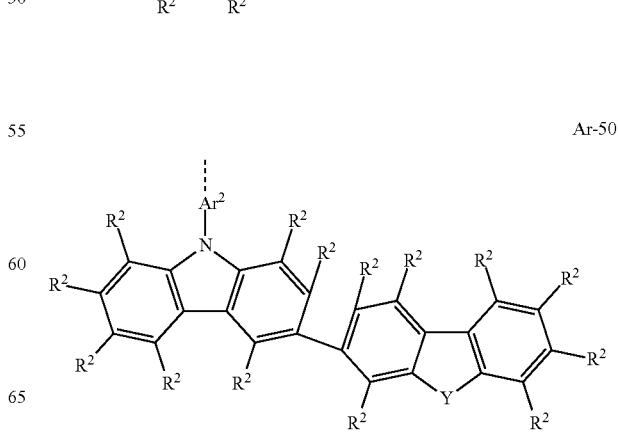

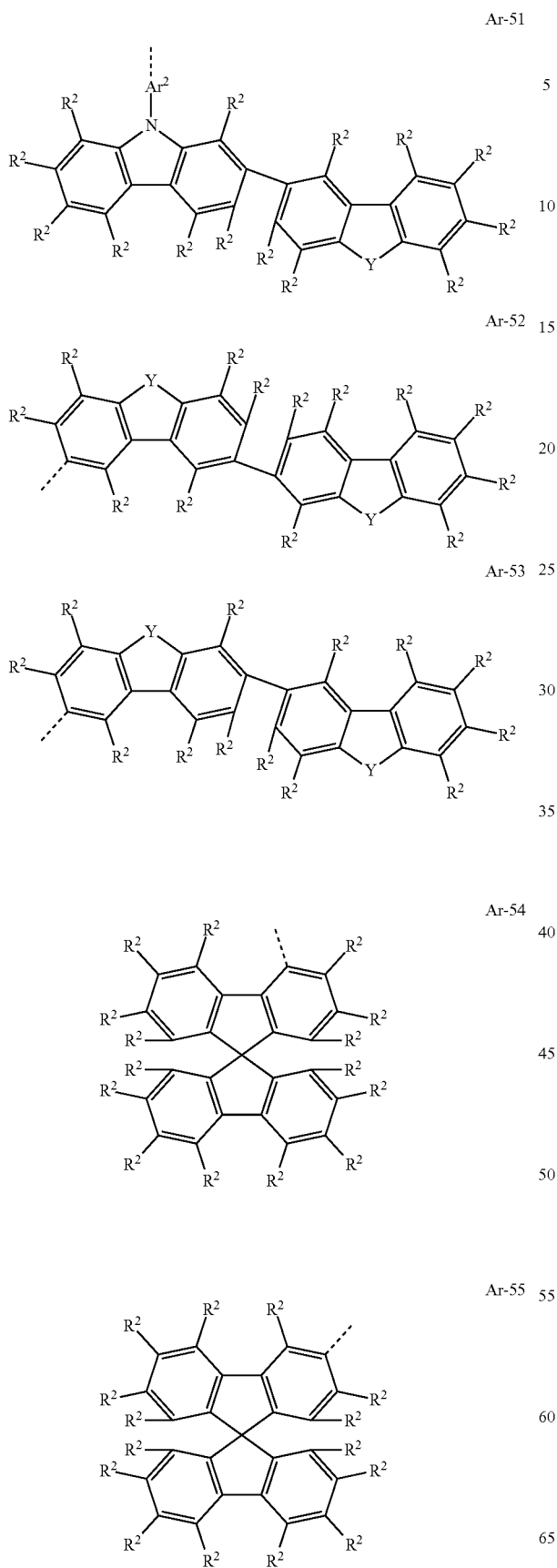

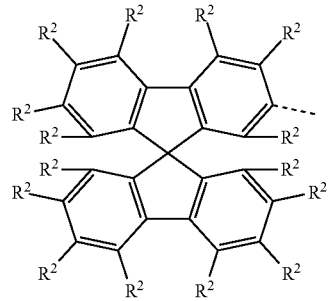

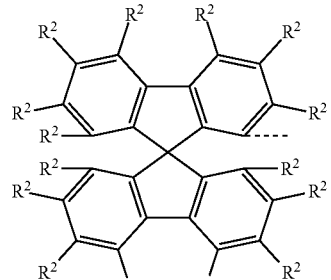

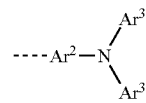

where R* has the definitions given in claim 1, the dotted bond represents the bond to the group of the formula (3) and, in addition:

Ar² is the same or different at each instance and is a bivalent aromatic or heteroaromatic ring system which has 6 to 18 aromatic ring atoms, does not contain any electron-deficient heteroaryl groups and may be substituted in each case by one or more R² radicals;

Ar³ is the same or different at each instance and is an aromatic or heteroaromatic ring system which has 6 to 18 aromatic ring atoms, does not contain any electron-deficient heteroaryl groups and may be substituted in each case by one or more R² radicals;

Y is the same or different at each instance and is C(R²)₂, NR², O or S;

n is 0 or 1, where n=0 means that no Y group is bonded at this position and R² radicals thereof are bonded to the corresponding carbon atoms instead;

where the Ar-1 to Ar-57 groups can also bind via a bridging group to the nitrogen atom in formula (3).

9. The compound as claimed in claim 1, wherein R¹ is the same or different at each instance and is selected from the group consisting of H, D, N(Ar¹)₂, a straight-chain alkyl group having 1 to 10 carbon atoms or a branched or cyclic alkyl group having 3 to 10 carbon atoms, each of which may be substituted by one or more R³ radicals, where one or more hydrogen atoms may be replaced by D or F, or an aromatic or heteroaromatic ring system which has 5 to 30 aromatic ring atoms and may be substituted in each case by one or more R³ radicals.

10. The compound as claimed in claim 1, wherein R¹, when it is an aromatic or heteroaromatic ring system, is selected from the groups R¹-1 to R¹-43

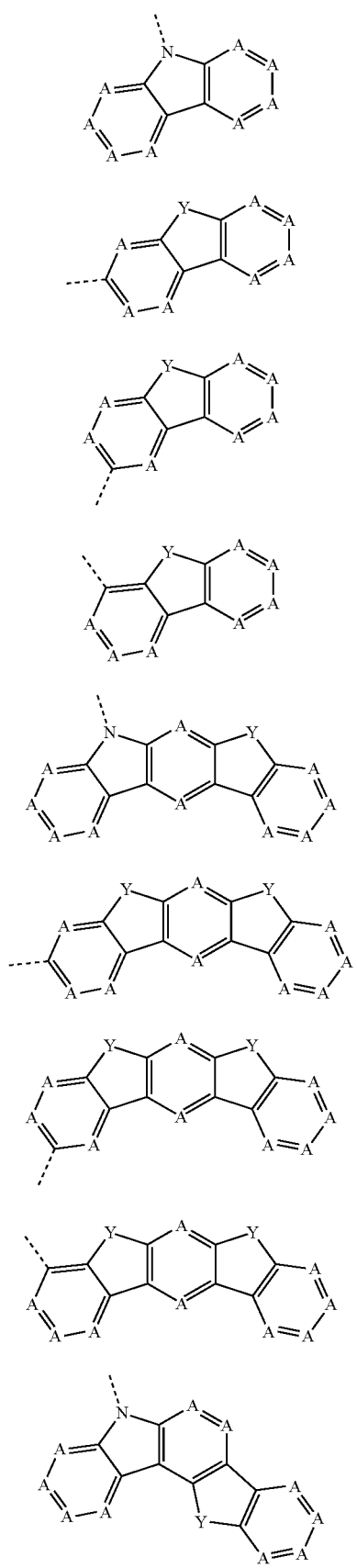
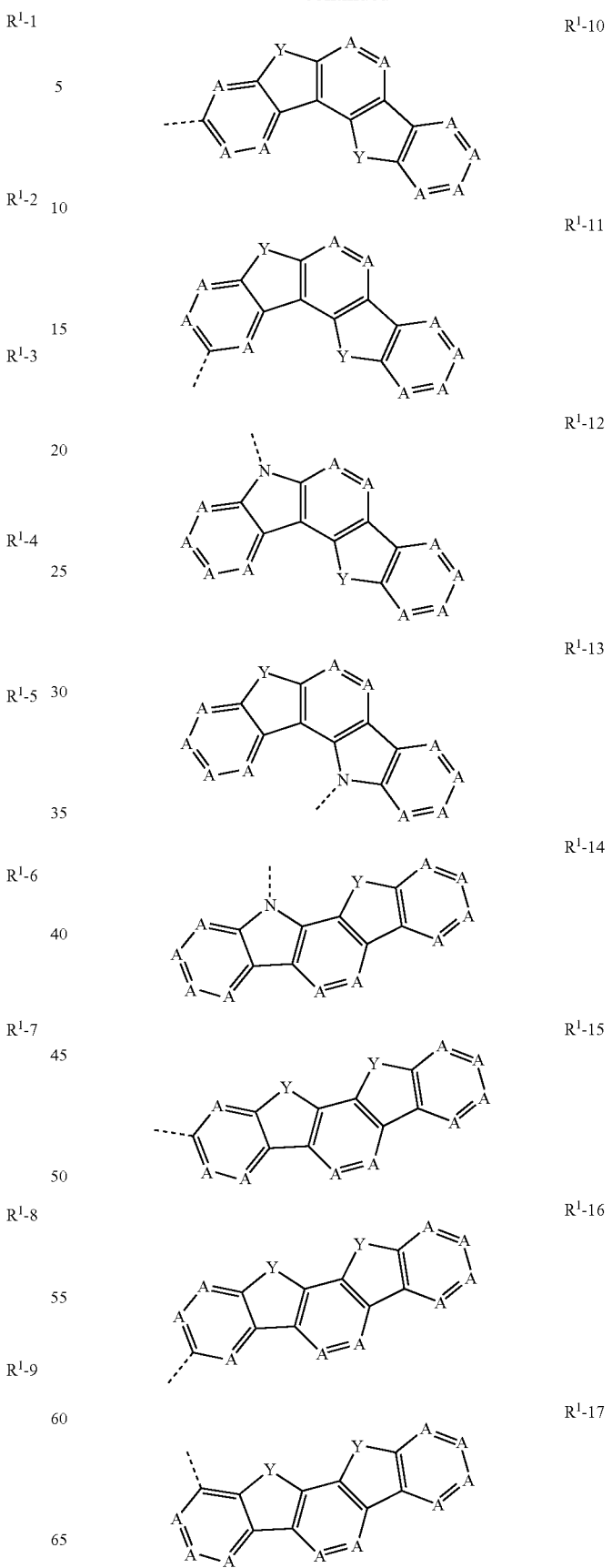

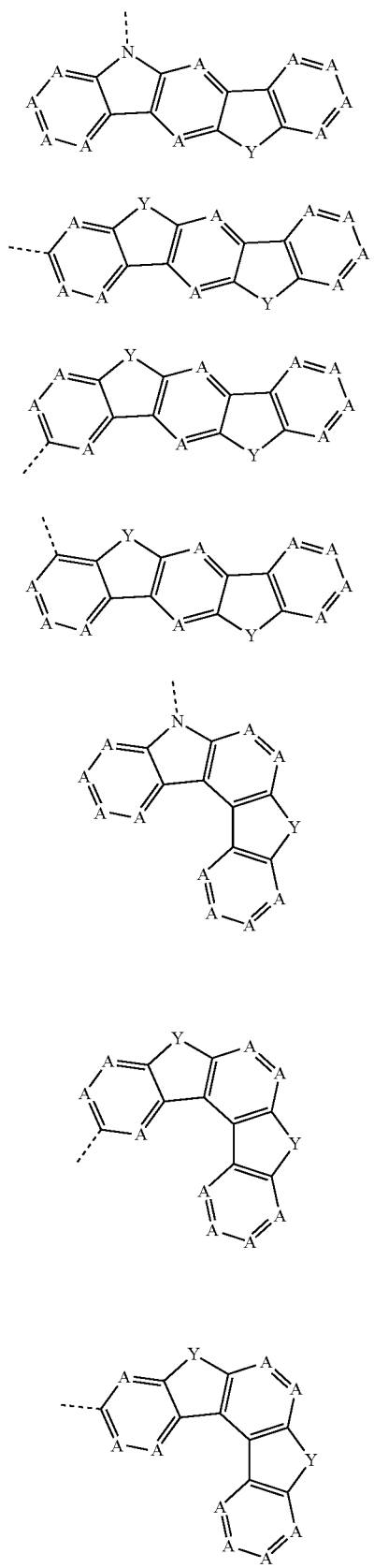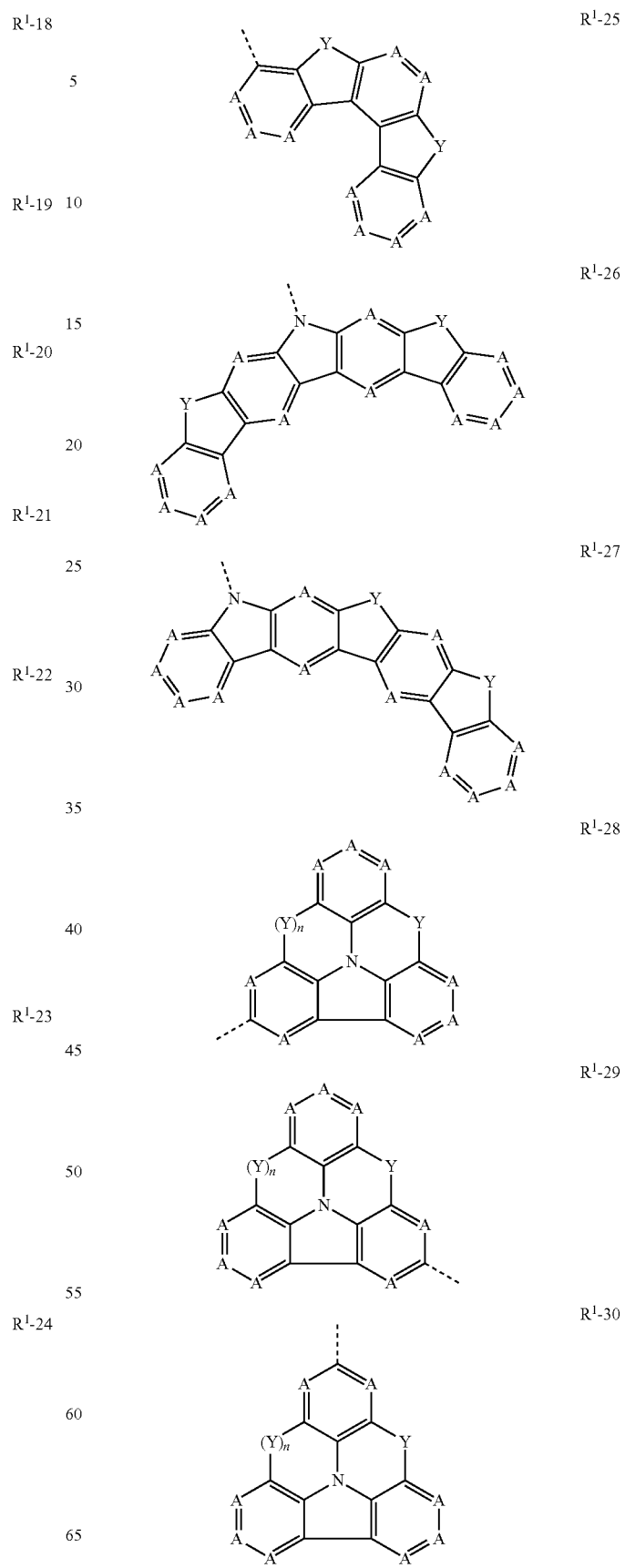

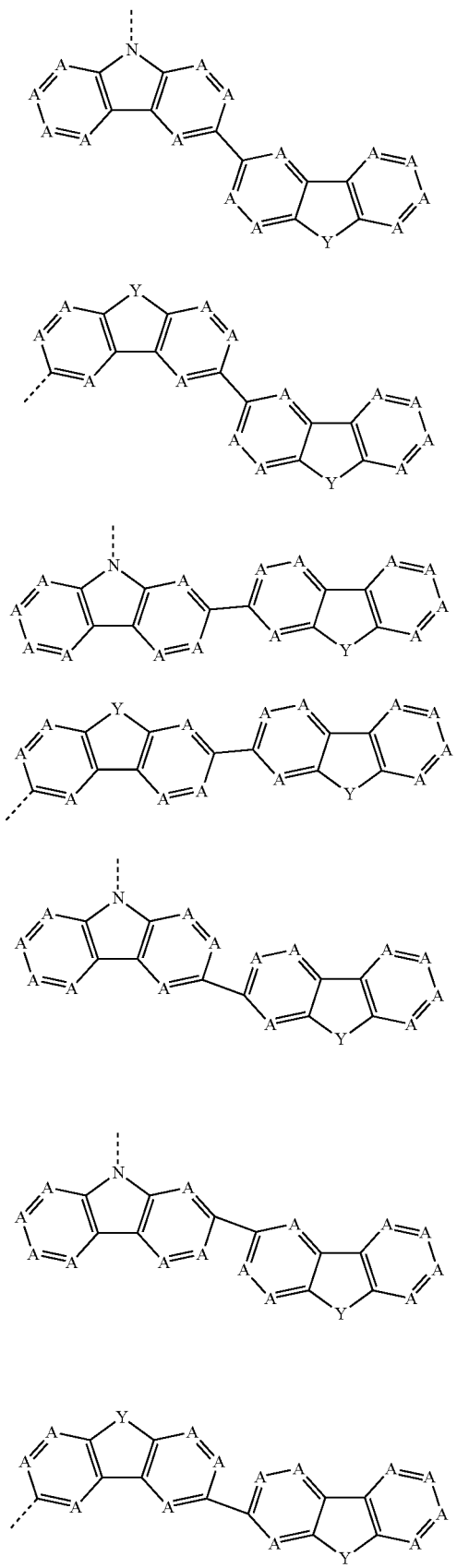
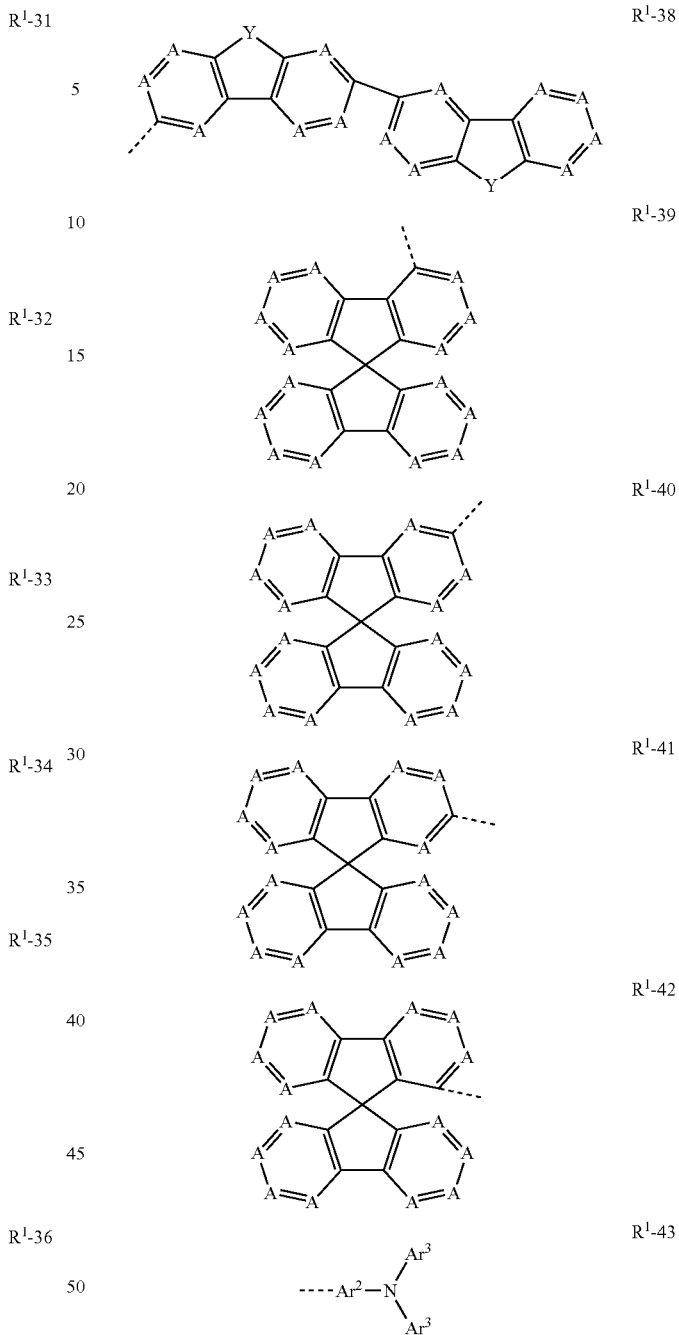

where $R^3$ has the definitions given in claim 1, the dotted bond represents the bond to the group of the formula (3) and, in addition:

A is the same or different at each instance and is $CR^3$ or N, where not more than 3 X symbols per cycle are N;

Y is the same or different at each instance and is $C(R^3)_2$, $NR^3$, O or S;

$Ar^2$, $Ar^3$ is the same or different at each instance and is an aromatic or heteroaromatic ring system which has 5 to 18 aromatic ring atoms, each of which may be substituted in each case by one or more $R^3$ radicals;

n is 0 or 1, where n=0 means that no Y group is bonded at this position and $R^3$ radicals thereof are bonded to the corresponding carbon atoms instead;

where the $R^1$-1 to $R^1$-42 groups can also bind via a bridging group to the nitrogen atom in formula (3).

11. An oligomer, polymer or dendrimer containing one or more compounds as claimed in claim 1, wherein one or more bonds of the compound to the polymer, oligomer or dendrimer are present in place of substituents at one or more positions.

12. A formulation comprising at least one compound as claimed in claim 1 and at least one further compound.

13. A formulation comprising at least one oligomer, polymer or dendrimer as claimed in claim 11 and at least one solvent.

14. An electronic device comprising the compound as claimed in claim 1.

15. An electronic device comprising the oligomer, polymer or dendrimer as claimed in claim 11.

16. The electronic device as claimed in claim 14, wherein the device is selected from the group consisting of organic electroluminescent devices, organic integrated circuits, organic field-effect transistors, organic thin-film transistors, organic light-emitting transistors, organic solar cells, dye-sensitized organic solar cells, organic optical detectors, organic photoreceptors, organic field-quench devices, light-emitting electrochemical cells, organic laser diodes and organic plasmon-emitting devices.

17. An organic electroluminescent device which comprises the compound as claimed in claim 1 is used as matrix material for phosphorescent or fluorescent emitters and/or in an electron-blocking or exciton-blocking layer and/or in a hole transport layer and/or in a hole blocker layer and/or in a hole blocker or electron transport layer.

18. A formulation comprising at least one compound as claimed in claim 1 and at least a solvent.

* * * * *